(12) United States Patent
Van Der Ploeg et al.

(10) Patent No.: US 7,321,074 B1
(45) Date of Patent: Jan. 22, 2008

(54) MELANOCORTIN-3 RECEPTOR DEFICIENT CELLS, NON-HUMAN TRANSGENIC ANIMALS AND METHODS OF SELECTING COMPOUNDS WHICH REGULATE BODY WEIGHT

(75) Inventors: Leonardus H. T. Van Der Ploeg, Scotch Plains, NJ (US); Howard Y. Chen, Westfield, NJ (US); Airu S. Chen, Westfield, NJ (US)

(73) Assignee: Merck & Co., Inc., Rahway, NJ (US)

( * ) Notice: Subject to any disclaimer, the term of this patent is extended or adjusted under 35 U.S.C. 154(b) by 543 days.

(21) Appl. No.: 10/129,599

(22) PCT Filed: Nov. 9, 2000

(86) PCT No.: PCT/US00/30746

§ 371 (c)(1),
(2), (4) Date: May 8, 2002

(87) PCT Pub. No.: WO01/33954

PCT Pub. Date: May 17, 2001

Related U.S. Application Data

(60) Provisional application No. 60/220,713, filed on Jul. 26, 2000, provisional application No. 60/165,141, filed on Nov. 12, 1999, provisional application No. 60/165,074, filed on Nov. 12, 1999.

(51) Int. Cl.
*A01K 67/027* (2006.01)
*C12N 5/00* (2006.01)
*C12N 5/06* (2006.01)
*C12N 5/10* (2006.01)

(52) U.S. Cl. .................. 800/18; 435/325; 435/352; 435/354

(58) Field of Classification Search ............... 435/325, 435/354, 352; 800/13, 14, 18
See application file for complete search history.

(56) References Cited

U.S. PATENT DOCUMENTS

| 5,622,860 A | 4/1997 | Yamada et al. |
| 5,703,220 A | 12/1997 | Yamada et al. |
| 5,837,521 A | 11/1998 | Cone et al. |
| 5,908,609 A | 6/1999 | Lee et al. |
| 5,932,779 A | 8/1999 | Lee et al. |

FOREIGN PATENT DOCUMENTS

WO    WO 02/03793    1/2002

OTHER PUBLICATIONS

Desarnaud et al. (1994) Molecular cloning, functional expression and pharmacological characterization of a mouse melanocortin receptor gene. Biochem. J. 299: 367-373.*
Bradley et al. (1992) Modifying the mouse: Design and desire. Bio/Technology 10: 534-539.*
Campbell and Wilmut (1997) Totipotency or multipotentiality of cultured cells: Applications and progress. Theriogenology 47: 63-72.*
Donehower et al. (1995) Effects of genetic background on tumorigenesis in p53-deficient mice. Molecular Carcinogenesis 14: 16-22.*
Jacks et al. (1992) Effects of an Rb mutation in the mouse. Nature 359: 295-300.*
Jaenisch et al. (1988) Transgenic Animals. Science 240: 1468-1474.*
Kuehn et al. (1987) A potential animal model for Lesch-Nyhan syndrome through introduction of HPRT mutations into mice. Nature 326: 295-298.*
Moens et al. (1993) Defects in heart and lung Development in compound heterozygotes for two different targeted mutations at the N-myc locus. Development 119: 485-499.*
Mullins et al. (1996) Transgenesis in the rat and larger mammals. J. Clin. Invest. 97(7): 1557-1560.*
Sigmund, CD (2000) Viewpoint: Are studies in genetically altered mice out of control? Arterioscler. Thromb. Vasc. Biol. 20: 1425-1429.*
Bert, C., et al., Molecular and Cellular Endocrinology, "Production of recombinant rat proopiomelanocortin 1-74 and characterization of its mitogenic action on pituitary lactotrophs", vol. 154, pp. 111-122, 1999.
Boston, Bruce A., et al., Science, "Independent and additive effects of central POMC and leptin pathways on murine obesity", vol. 278, pp. 1641-1644, 1997.
Butler, Andrew A., et al., Endocrinology, "A unique metabolic syndrome causes obesity in the melanocortin-3 receptor-deficient mouse", vol. 141, No. 9, pp. 3518-3521, 2000.
Capecchi, Mario R., et al., Trends in Genetics, "The new mouse genetics: altering the genome by gene targeting", vol. 5, No. 3, pp. 70-76, 1989.
Chen, Wenbiao, et al., Analytical Biochemistry, "A colorimetric assay for measuring activation of G - and G - Coupled Signaling Pathways", vol. 226, pp. 349-354, 1995.

(Continued)

*Primary Examiner*—Anne-Marie Falk
(74) *Attorney, Agent, or Firm*—Baerbel R. Brown; Laura M. Ginkel; Catherine D. Fitch

(57) ABSTRACT

Cells and non-human transgenic animals have been engineered to be deficient in the gene encoding the melcanocortin-3 receptor protein (MC-3R). MC-3R deficient transgenic animals have increased fatmass and reduced lean body mass, showing that the MC-3R protein is involved in the regulation of body fat and muscle mass. These MC-3R deficient transgenic animals can be used to select for and test potential modulators of MC-3R. This data allows for methods of screening for MC-3R modulators which effect body weight and associated methods of treating various disorders associated with inappropriate regulation of body weight. The disclosure also relates to a MC-3R/MC-4R double knockout mouse which can be used to select for and test potential modulators (e.g., agonists or antagonists) of MC-3R and/or MC-4R. It is shown that MC-3R serves a non-redundant role, when compared to MC-4R, in the regulation of energy homeostasis.

3 Claims, 29 Drawing Sheets

OTHER PUBLICATIONS

Chen, Wenbiao, et al., Cell, "Exocrine gland dysfunction in MC5-R-deficient mice: evidence for coordinated regulation of exocrine gland function by melanocortin peptides", vol. 91, pp. 789-798, 1997.

Chen, Peilin, et al., Endocrinology, "Altered expression of agouti-related protein and its colocalization with neuropeptide Y in the arcuate nucleus of the hypothalamus during lactation", vol. 140, No. 6, 1999.

Cunningham, Matthew J., et al., Biology of Reproduction, "Leptin's actions on the reproductive axis: perspectives and mechanisms", vol. 60, pp. 216-222, 1999.

Chen, Airu S., et al, Nature Genetics, "Inactivation of the mouse melanocortin-3 receptor results in increased fat mass and reduced lean body mass", vol. 26, pp. 97-102, 2000.

Cone, Roger D., et al., Recent Progress in Hormone Research, "The melanocortin receptors: agonists, antagonists, and the hormonal control of pigmentation", vol. 51, pp. 287-318, 1996.

Dinulescu, Daniela M., et al., Proc. Natl. Acad. Sci., "*Mahogany (mg)* stimulates feeding and increases basal metabolic rate independent of its supression of agouti", vol. 95, pp. 12707-12712, 1998.

Elias, Carole F., et al., Neuron, "Leptin activates hypothalamic CART neurons projecting to the spinal cord", vol. 21, pp. 1375-1385, 1998.

Fan, Wei, et al., Letters to Nature, "Role of melanocortinergic neurons in feeding and the agouti obesity syndrome", vol. 385, pp. 165-168, 1997.

Finn, Patricia D., et al., Endocrinology, "The stimulatory effect of leptin on the neuroedocrine reproductive axis of the monkey", vol. 139, pp. 4652-4662, 1998.

Fong, Tung Ming, et al., Biochemical and Biophysical Research Communications, "ART (Protein product of agouti-related transcript) as an antagonist of MC-3 and MC-4 receptors", vol. 237, pp. 629-631, 1997.

Gantz, Ira, et al., The Journal of Biological Chemistry, "Molecular cloning of a novel melanocortin receptor", vol. 268, Nol. 11, pp. 8246-8250, 1993.

Giros, Bruno, et al., Nature, "Hyperlocomotion and indifference to cocaine and amphetamine in mice lacking the dopamine transporter", vol. 379, pp. 606-612, 1996.

Guan, Xio-Ming, et al., Molecular Brain Research 59, "Evidence of altered hypothalamic pro-opiomelanocortin/neuropeptide Y mRNA expression in tubby mice", vol. 59, pp. 273-279, 1998.

Gunn, Teresa M., et al., Letters to Nature, "The mouse *mahogany* locus encodes a transmembrane form of human attractin", vol. 398, pp. 152-156, 1999.

Hadley, Mac E., et al., Pharmaceutical Biotechnology, "Discovery and development of novel melanogenic drugs", pp. 575-595, 1998.

Hahn,Tina M., et al, Nature Neuroscience, "Coexpression of Agrp and NPY in fasting-activated hypothalamic neurons", vol. 1, No. 4, pp. 271-272, 1998.

Haynes, William G., et al., Hypertension, "Interactions Between the melanocortin system and leptin in control of sympathetic nerve traffic", vol. 33, pp. 542-547, 1999.

Huszar, Dennis et al., Cell, "Targeted disruption of the melanocortin-4 receptor results in obesity in mice", vol. 88, pp. 131-11, 1997.

Kalra, Satya P., et al., Endocrine Reviews, "Interacting appetite-regulating pathways in the hypothalamic regulation of body weight", vol. 20, No. 1, pp. 68-100, 1999.

Kask, Ants, et al., Endocrinology, "Discovery of a novel superpotent and selective melanocortin-4 receptor antagonist (HS024): evaluation in Vitro and in Vivo", vol. 139, No. 12, 1998.

Life Science Dictionary, Hemizygous Definition, 2002.

Lu, Dongsi, et al., Letters to Nature, "Agouti protein is an antagonist of the melanocyte-stimulating-hormone receptor", vol. 371, pp. 799-802, 1994.

Marsh, Donald J., et al., Nature Genetics, "Responsse of melanocortin-4-deficient mice to anorectic and orexigenic peptides", vol. 21, pp. 119-122, 1999.

Miltenberger, Rosalynn J., et al., J. Nutr., "The role of the agouti gene in the yellow obese syndrome", vol. 127, pp. 1902S-1907S, 1997.

Mountjoy, Kathleen G., et al., Molecular Endocrinology, "Localization of the melanocortin-4 receptor (MC4-R) in neuroendocrine and autonmic control circuits in the brain", vol. 8, pp. 1298-1308, 1994.

Mountjoy, Kathleen G., et al., Molecular and Cellular Endocrinology, "Obesity, diabetes and functions for proopiomelanocortin-derived peptides", vol. 128, pp. 171-177, 1997.

Nagle, Deborah L., et al., Letters to Nature, "The *mahogany* protein is a receptor involved in suppression of obesity", vol. 398, pp. 148-152, 1999.

Roselli-Rehfuss, Linda, et al., Proc. Natl. Acad. Sci., "Identification of a receptor fo y melanotropin and other proopiomelanocortin peptides in the hypothalamus and limbic system", vol.. 90, pp. 8856-8860, 1993.

Roberts, Susan B., et al., Nutrition Reviews, "The new obesity genes", vol. 54, No. 2, pp. 41-49, 1996.

Schioth, Helgi B., et al., Biochemical and Biophysical Research Communications, "Evidence indicating that the TM4, EL2, and TM5 of the melanocortin 3 receptor do not participate in ligand binding", vol. 229, pp. 687-692, 1996.

Shutter, John R., et al., Genes & Development, "Hypothalamic expression of ART, a novel gene related to agouti, is up-regulated in *Obese* and *Diabetic* mutant mice", vol. 11, pp. 593-602, 1997.

Tybulewicz, Victor L., et al., Cell, "Neonatal lethality and lymphopenia in mice with a homozygous disruption of the c-abl proto-oncogene", vol. 65, pp. 1153-1163, 1991.

Von Koch, C.S., et al., Neurobiology of Aging, "Generation of APLP2 KO mice and early postnatal lethality in APLP2/APP double KO mice", vol. 18, No. 6, pp. 661-669, 1997.

Yang, Ying-Kui, et al., Molecular Endocrinology, "Characterization of agouti-related protein binding to melanocortin receptors", vol. 13, pp. 148-155, 1999.

Yen, Terence T., et al., FASEB, "Obesity, diabetes, and neoplasia in yello A /- mice; ectopic expression of the agouti gene", vol. 8, pp. 479-488, 1994.

\* cited by examiner

```
TCTAGACTGG ACAGCATCCA CAAGAGAAGC ACCTAGAAGG AGAATTTTCC CCAGCAGCTT
GCTCAGGACC CTGCAGGAGC CGCAGCTGGG ACTGGACCTG CTGTTAACCA TGAACTCTTC
CTGCTGCCTG TCTTCTGTTT CTCCGATGCT GCCTAACCTC TCTGAGCACC CTGCAGCCCC
TCCTGCCAGC AACCGGAGCG GCAGTGGGTT CTGTGAGCAG GTCTTCATCA AGCCGGAGGT
CTTCCTGGCT CTGGGCATCG TCAGTCTGAT GGAAAACATC CTGGTGATCC TGGCTGTGGT
CAGGAATGGC AACCTGCACT CTCCCATGTA CTTCTTCCTG TGCAGCCTGG CTGCAGCCGA
CATGCTGGTG AGCCTGTCCA ACTCCCTGGA GACCATCATG ATCGCCGTGA TCAACAGCGA
CTCCCTGACC TTGGAGGACC AGTTTATCCA GCACATGGAT AATATCTTCG ACTCTATGAT
TTGCATCTCC CTGGTGGCCT CCATCTGCAA CCTCCTGGCC ATTGCCATCG ACAGGTACGT
CACCATCTTC TATGCCCTTC GGTACCACAG CATCATGACA GTTAGGAAAG CCCTCACCTT
GATCGGGGTC ATCTGGGTCT GCTGCGGCAT CTGCGGCGTG ATGTTCATCA TCTACTCCGA
GAGCAAGATG GTCATCGTGT GTCTCATCAC CATGTTCTTC GCCATGGTGC TCCTCATGGG
CACCCTATAT ATCCACATGT TCCTCTTCGC CAGGCTCCAC GTCCAGCGCA TCGCAGTGCT
GCCCCCTGCT GGCGTGGTGG CCCCACAGCA GCACTCCTGC ATGAAGGGGG CTGTCACCAT
CACTATCCTG CTGGGTGTTT TCATCTTCTG CTGGGCGCCT TTCTTCCTCC ACCTGGTCCT
CATCATCACC TGCCCCACCA ATCCCTACTG CATCTGCTAC ACGGCCCATT TCAACACCTA
CCTGGTTCTC ATCATGTGCA ACTCCGTCAT CGACCCCCTC ATCTACGCCT TCCGCAGCCT
GGAGCTGCGC AACACGTTCA AGGAGATTCT CTGCGGCTGC AACAGCATGA ACTTGGGCTA
GGATGCCCGT GGAGGTGTTC CACATCCAGC CAAGAGACAA AAACAACGCT CAGACGGGAC
GTAAAAGGGT GTTAGGAGCT GGAACTGTGC TTGGCTTCGT CTGTAAGCTC GTGGCCCTTT
GCAGACGGGA CACGGCGTAG GATGGGCTGT CTGTGAGGAT CTGTGTGTGG GTAAGTCAGT
TTGATCTAGC ACATAGCCTG GAAGAATCAG GCAAAGCAGC CCTGAGTGTC ATCTGTGTTC
ATTGCTAGGC ACCCAGGGTT TGTGGCCCCT GCCTGCTTAT TGGCTTTGTA CCAGTAACTG
TGCTTCAAGC CAACCAGACC GGAGGGCTCT CGTGAGCAGA AAGAGTGCTT AGACTTCCGG
CAAGCATCCT GGCTCACAGC GGCCACCTCC TGACCACTAC CGGGAGAGCT TTGCACATAT
TCTGTGGGAG ATTGAGTGAA GCCCTGAAAA CAATGTGATA TTTGCTGCTC CCTTCCAGAA
CTTACATCTG TGCCAGCCTC CCCGAACCCC TGCACAGAGA CATGACCCCC TTCTCCCTGT
GCCGTTGTCA TGGTTGTTAT TATTGTTGGA GTTTTGTTCG TTAAAATCTA AGCTT (SEQ ID NO:1)
```

FIG.1

```
MNSSCCLSSV SPMLPNLSEH PAAPPASNRS GSGFCEQVFI KPEVFLALGI VSLMENILVI
LAVVRNGNLH SPMYFFLCSL AAADMLVSLS NSLETIMIAV INSDSLTLED QFIQHMDNIF
DSMICISLVA SICNLLAIAI DRYVTIFYAL RYHSIMTVRK ALTLIGVIWV CCGICGVMFI
IYSESKMVIV CLITMFFAMV LLMGTLYIHM FLFARLHVQR IAVLPPAGVV APQQHSCMKG
AVTITILLGV FIFCWAPFFL HLVLIITCPT NPYCICYTAH FNTYLVLIMC NSVIDPLIYA
FRSLELRNTF KEILCGCNSM NLG (SEQ ID NO:2)
```

FIG.2

ATGAGCATCC AAAAGAAGTA TCTGGAGGGA GATTTTGTCT TTCCTGTGAG CAGCAGCAGC
TTCCTACGGA CCCTGCTGGA GCCCCAGCTC GGATCAGCCC TTCTGACAGC AATGAATGCT
TCGTGCTGCC TGCCCTCTGT TCAGCCAACA CTGCCTAATG GCTCGGAGCA CCTCCAAGCC
CCTTTCTTCA GCAACCAGAG CAGCAGCGCC TTCTGTGAGC AGGTCTTCAT CAAGCCCGAG
ATTTTCCTGT CTCTGGGCAT CGTCAGTCTG CTGGAAAACA TCCTGGTTAT CCTGGCCGTG
GTCAGGAACG GCAACCTGCA CTCCCCGATG TACTTCTTTC TGCAGCCT GGCGGTGGCC
GACATGCTGG TAAGTGTGTC CAATGCCCTG GAGACCATCA TGATCGCCAT CGTCCACAGC
GACTACCTGA CCTTCGAGGA CCAGTTTATC CAGCACATGG ACAACATCTT CGACTCCATG
ATCTGCATCT CCCTGGTGGC CTCCATCTGC AACCTCCTGG CCATCGCCGT CGACAGGTAC
GTCACCATCT TTTACGCGCT CCGCTACCAC AGCATCATGA CCGTGAGGAA GGCCCTCACC
TTGATCGTGG CCATCTGGGT CTGCTGCGGC GTCTGTGGCG TGGTGTTCAT CGTCTACTCG
GAGAGCAAAA TGGTCATTGT GTGCCTCATC ACCATGTTCT TCGCCATGAT GCTCCTCATG
GGCACCCTCT ACGTGCACAT GTTCCTCTTT GCGCGGCTGC ACGTCAAGCG CATAGCAGCA
CTGCCACCTG CCGACGGGGT GGCCCCACAG CAACACTCAT GCATGAAGGG GGCAGTCACC
ATCACCATTC TCCTGGGCGT GTTCATCTTC TGCTGGGCCC CCTTCTTCCT CCACCTGGTC
CTCATCATCA CCTGCCCCAC CAACCCCTAC TGCATCTGCT ACACTGCCCA CTTCAACACC
TACCTGGTCC TCATCATGTG CAACTCCGTC ATCGACCCAC TCATCTACGC TTTCCGGAGC
CTGGAATTGC GCAACACCTT TAGGGAGATT CTCTGTGGCT GCAACGGCAT GAACTTGGGA (SEQ ID
NO:3)

FIG.3

MSIQKKYLEG DFVFPVSSSS FLRTLLEPQL GSALLTAMNA SCCLPSVQPT LPNGSEHLQA
PFFSNQSSSA FCEQVFIKPE IFLSLGIVSL LENILVILAV VRNGNLHSPM YFFLCSLAVA
DMLVSVSNAL ETIMIAIVHS DYLTFEDQFI QHMDNIFDSM ICISLVASIC NLLAIAVDRY
VTIFYALRYH SIMTVRKALT LIVAIWVCCG VCGVVFIVYS ESKMVIVCLI TMFFAMMLLM
GTLYVHMFLF ARLHVKRIAA LPPADGVAPQ QHSCMKGAVT ITILLGVFIF CWAPFFLHLV
LIITCPTNPY CICYTAHFNT YLVLIMCNSV IDPLIYAFRS LELRNTFREI LCGCNGMNLG (SEQ ID
NO:4)

FIG.4

Southern blot analysis

PCR analysis

MELANOCORTIN-3 RECEPTOR DEFICIENT CELLS, NON-HUMAN TRANSGENIC ANIMALS AND METHODS OF SELECTING COMPOUNDS WHICH REGULATE BODY WEIGHT

CROSS-REFERENCE TO RELATED APPLICATIONS

This application is the §371 National Stage prosecution of PCT International Application serial no. PCT/US00/30746, having an international filing date of Nov. 9, 2000, which claims benefit under 35 U.S.C. §119(e) to U.S. Provisional Application Ser. No. 60/220,713, filed Jul. 26, 2000, U.S. Provisional Application Ser. No. 60/165,141, filed Nov. 12, 1999, and U.S. Provisional Application Ser. No. 60/165,074, filed Nov. 12, 1999, now expired.

STATEMENT REGARDING FEDERALLY-SPONSORED R&D

Not Applicable

REFERENCE TO MICROFICHE APPENDIX

Not applicable.

FIELD OF THE INVENTION

The present invention relates to cells and non-human transgenic animals that have been engineered to be deficient in the gene encoding the melcanocortin-3 receptor protein (MC-3R). It is shown herein that MC-3R deficient transgenic animals have increased fat mass and reduced lean body mass, showing that the MC-3R protein is involved in the regulation of body fat and lean body mass. The MC-3R deficient transgenic animals of the present invention, including a MC-3R/MC-4R double knockout mouse, can be used to select for and test potential modulators (e.g., agonists or antagonists) of MC-3R, as well as dual modulators of MC-3R and MC4R. It is shown herein that MC-3R serves a non redundant role, when compared to MC4R, in the regulation of energy homeostasis. To this end, the present invention also relates to methods of screening for MC-3R modulators which effect body weight and associated methods of treating various disorders or diseases responsive to the action of one or more of the melanocortin receptors, including but not limited to obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immunomodulation, rheumatoid arthritis, learning memory, modulation of cytokine release, skin tanning, acne and other skin disorders, neuroregeneration and neuroprotective and cognitive and memory enhancement including the treatment of Alzheimer's disease.

BACKGROUND OF THE INVENTION

Melanocortin receptors belong to the rhodopsin sub-family of G-protein coupled receptors (GPCR's). Five different subtypes are known. These melanocortin receptors bind and are activated by peptides such as $\alpha$-, $\beta$, or $\gamma$-melanocyte stimulating hormones ($\alpha$-, $\beta$-, $\gamma$-MSH) derived from the pro-opiomelanocortin (POMC) gene. A wide range of physiological functions are believed to be mediated by melanocortin peptides and their receptors.

Desarnaud et al. (1994, *Biochem J.* 299 (2): 367-372) disclose a cDNA clone encoding mouse MC-3R.

Roselli-Rehfuss et al. (1993, *Proc. Natl. Acad. Sci.* 90: 8856-8860) disclose a cDNA clone encoding rat MC-3R cDNA.

U.S. Pat. No. 5,622,860 (issued Apr. 22, 1997) and U.S. Pat. No. 5,703,220 (issued Dec. 30, 1997) to Yamada and Gantz, disclose DNA molecules which encode human MC-3R and human MC-4R, respectively (see also Gantz, et al., 1993, *J. Biol. Chem.* 268(11): 8246-8250).

The agouti mouse represents a naturally occurring obese rodent, with a late life onset of obesity which is not corticosterone dependent. The obesity in this model results from the ectopic expression of the 131 amino acid agouti protein. Agouti is normally only expressed in the skin where it controls hair color. The protein is a paracrine antagonist of the melanocortin-1 receptor (MC-1R), a G-protein coupled receptor of the hair follicle. MC-1R agonism, through its natural ligand, $\alpha$-MSH raises cAMP and the expression of the enzyme tyrosinase. Low levels of tyrosinase, which result from agouti antagonism of MC-1R, result in reduced conversion of the hair color pigment pheomelanin to eumelanin. As a result a light (agouti) rather than black hair color results. The obese phenotype of the agouti mouse was ascribed to the expression of agouti in the brain, where it antagonizes MC-3R and MC-4R receptors. This conclusion was corroborated by the generation of an MC-4R knockout mouse which recapitulates the obese phenotype of the agouti mutant mouse (see U.S. Pat. No. 5,932,779, issued Aug. 3, 1999 to Lee et al.) In rodents, MC-4R has been implicated as a key regulator of feeding behavior which regulates body weight through studies with peptide agonists and antagonists (Fan et al., 1997, *Nature* 385: 165-168) and with a MC-4R knock-out mouse (Huszar et al., 1997, *Cell* 88: 131-141, see also U.S. Pat. No. 5,932,779, issued Aug. 3, 1999 to Lee et al).

It is desirable to discover new drugs for the treatment of body weight disorders which selectively modulate a melanocortin receptor within the host.

It is also desirable to identify additional receptor targets which are involved in regulating body weight.

The present invention also addresses and meets these needs by disclosing MC-3R-deficient animal cells and/or MC-3R/MC-4R deficient animal cells, related non-human transgenic embryos, non-human transgenic animals and non-human transgenic littermates which are also MC-3R-deficient or MC-3R/MC-4R deficient.

The present invention addresses and meets these needs by disclosing methods of screening for compounds which effect body weight comprising the screening and selection of compounds which modulate the MC-3R.

SUMMARY OF THE INVENTION

The present invention relates to animal cells which are homozygous for an MC-3R deficiency due to a disruption in the gene(s) encoding MC-3R. To this end, the present invention also relates to non-human transgenic embryos, non-human transgenic animals and non-human transgenic littermates which are MC-3R deficient (MC-3R null) due to a disruption in the gene(s) encoding MC-3R.

The present invention further relates to animal cells, non-human transgenic embryos, non-human transgenic animals and non-human transgenic littermates which are heterozygous for a functional MC-3R gene native to that animal.

The present invention also relates in part to animal cells, non-human transgenic embryos and non-human transgenic littermates having a non-native gene encoding a MC-3R protein expressed either in the presence or absence of the native (wild type) MC-3R. Preferably, the non-native MC-3R gene is the human MC-3R gene.

The present invention also relates to transgenic embryos, non-human transgenic embryos, non-human transgenic animals and non-human transgenic littermates which are either homozygous, heterozygous or hemizygous for deletion of at least a portion of the MC-3R gene in combination with a homozygous, heterozygous or hemizygous deletion at separate alleles which in their wild type form encode at least one additional melanocortin receptor, especially a melanocortin receptor shown to be involved in body weight regulation, such as MC-4R. Therefore, aspects of the invention relate to transgenic embryos, non-human transgenic embryos, non-human transgenic animals and non-human transgenic littermates which are $MC-3R^{-/+}/MC-4R^{-/-}$; $MC-3R^{-/+}/MC-4R^{-/+}$; $MC-3R^{-/-MC}-4R^{-/+}$, as well as hemizygous alternatives in reference to the two separate alleles. An especially preferred aspect of the present invention relates to $MC-3R^{-/+}/MC-4^{-/-}$ double knockout mice and related transgenic embryos, non-human transgenic embryos, non-human transgenic animals and non-human transgenic littermates.

The transgenic cells and animals of the present invention are useful in the study of the effect of modulators on the activity of the MC-3R gene and/or protein or the expression of the MC-3R gene and/or protein as concerning the regulation of body weight, including but not limited to disorders such as obesity, diabetes, cardiovascular disease, anorexia, cachexia, cancer, male and female sexual dysfunction, pain, memory, neuronal regeneration and neuropathy.

The present invention also relates to MC-3R-based assays to select for modulators of this receptor protein which affect regulation of body weight through the various known disorders associated with regulation of body weight, as described herein. For example, a MC-3R modulator may be used to treat these body weight disorders, such as a MC-3R agonist to treat obesity or a MC-3R antagonist to treat anorexia and related disorders. These assays may be cell-based assays or may utilize membrane preparations which comprise the MC-3R. Modulation of the MC-3R may also be used to treat growth disorders relating to reduced GH, IGF1 function, treatment of reduced lean body mass as it occurs in the frail elderly, other states that are characterized as resulting from GH deficiency, cancer cachexia, disorders associated with depression and anxiety, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immunemodulation, rheumatoid arthritis, learning memory, modulation of cytokine release, skin tanning, acne and other skin disorders, neuroregeneration and neuroprotective and cognitive and memory enhancement including the treatment of Alzheimer's disease.

As used herein, the term "functional" is used to describe a gene or protein that, when present in a cell or in vitro system, performs normally as if in a native or unaltered condition or environment. Therefore, a gene which is not functional (i.e., "non-functional", "disrupted", "altered", or the like) will encode a protein which does not function as a wild type, native or non-altered protein, or encodes no protein at all. Such a non-functional gene, such as a non-functional MC-3R gene, may be the product of a homologous recombination event as described herein, where a non-functional gene is targeted specifically to the region of the target chromosome which contains a functional form of the gene, resulting in a "knock-out" of the wild type or native gene.

As used herein, a "modulator" is a compound that causes a change in the expression or activity of MC-3R, or causes a change in the effect of the interaction of MC-3R with its ligand(s), or other protein(s), such as an agonist or antagonist.

As used herein in reference to transgenic animals of this invention, we refer to "transgenes" and "genes". As used herein, a transgene is a genetic construct including a gene. The transgene is integrated into one or more chromosomes in the cells in an animal by methods known in the art. Once integrated, the transgene is carried in at least one place in the chromosomes of a transgenic animal. A gene is a nucleotide sequence that encodes a protein, or structural RNA. The gene and/or transgene may also include genetic regulatory elements and/or structural elements known in the art.

As used herein, the term "animal" is used herein to include all mammals, except that when referring to transgenic animals, the use of this term excludes humans. It also includes an individual animal in all stages of development, including embryonic and fetal stages. A "transgenic animal" is an animal containing one or more cells bearing genetic information received, directly or indirectly, by deliberate genetic manipulation at a subcellular level, such as by microinjection or infection with recombinant virus. This introduced DNA molecule can be integrated within a chromosome, or it can be extra-chromosomally replicating DNA. Unless otherwise noted or understood from the context of the description of an animal, the term "transgenic animal" as used herein refers to a transgenic animal in which the genetic information was introduced into a germ line cell, thereby conferring the ability to transfer the information to offspring. If offspring in fact possess some or all of the genetic information, then they, too, are transgenic animals. The genetic information is typically provided in the form of a transgene carried by the transgenic animal.

As used herein, a "targeted gene" or "knock out" (KO) is a DNA sequence introduced into the germline of a non-human animal by way of human intervention, including but not limited to, the methods described herein. The targeted genes of the invention include nucleic acid sequences which are designed to specifically alter cognate endogenous alleles, especially endogenous alleles which encode MC-3R, or alternatively, both MC-3R and MC-4R. The "knock out" can be the result of an altered, or preferably, completely deleted MC-3R gene, but also includes but is not limited to MC-3R (and MC-4R) gene deletions, gene modifications and or gene insertions which render the native gene nonfunctional or at least substantially nonfunctional, producing a "knock out" transgenic animal, or can lead to a MC-3R (or MC-3R and MC4R) receptor with altered expression or activity. As noted above, a non-human transgenic animal without an activated MC-3R gene can be used to evaluate the role of MC-3R in obesity and other associated disorders, while a MC-3R/MC4R knock out can be used to evaluate the role of MC-3R/MC-4R dual modulators in obesity and other disorders described herein.

As used herein, "MC-1R" refers to the melanocortin-1 receptor.

As used herein, "MC-3R" refers to the melanocortin-3 receptor.

As used herein, "MC-4R" refers to the melanocortin-4 receptor.

BRIEF DESCRIPTION OF THE FIGURES

FIG. 2 shows the amino acid sequence of the murine MC-3R (SEQ ID NO:2).

FIG. 3 shows the nucleotide sequence which encodes the human MC-3R (SEQ ID NO:3).

FIG. 4 shows the amino acid sequence of the human MC-3R (SEQ ID NO:4).

DETAILED DESCRIPTION OF THE INVENTION

Figure 5:
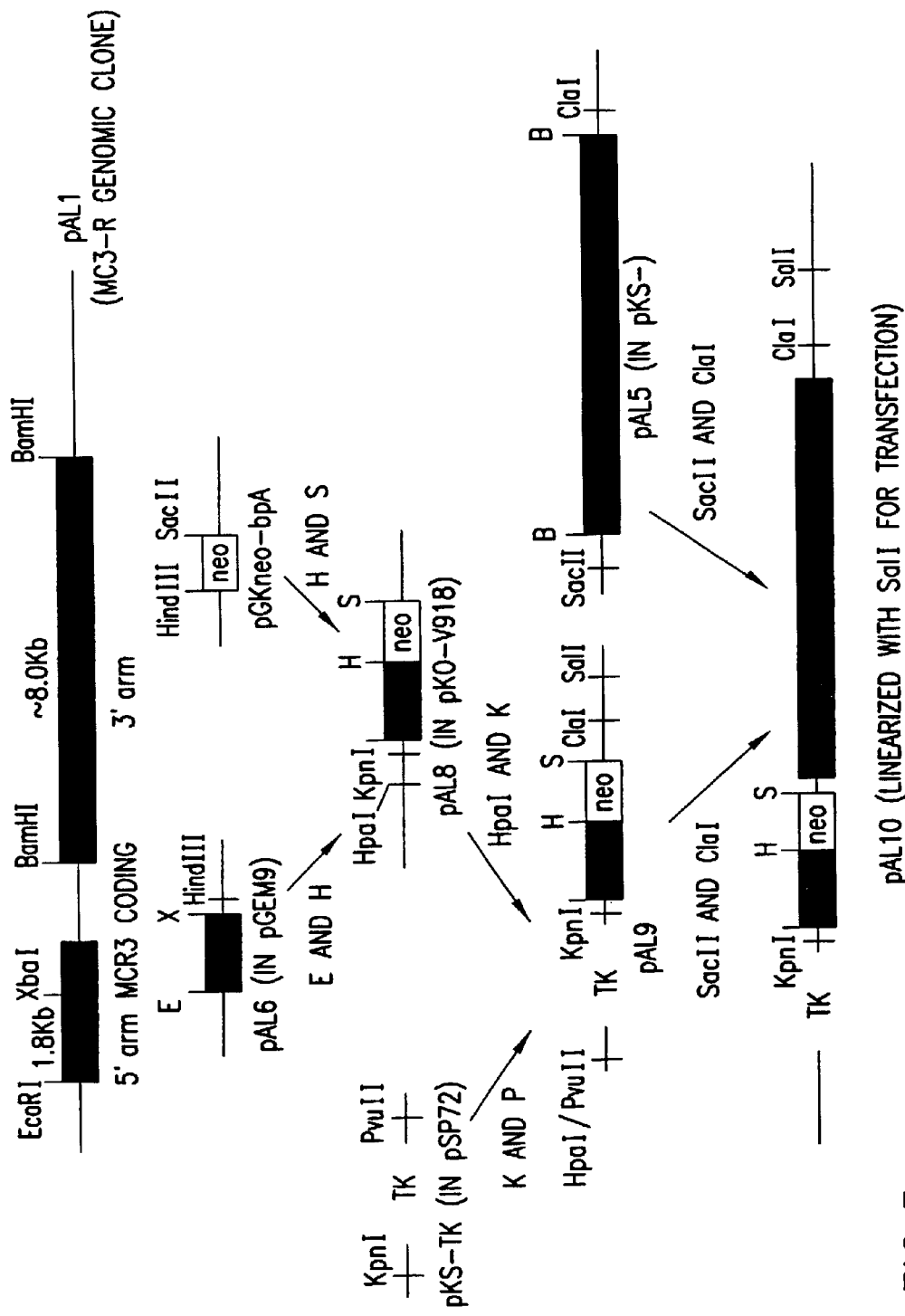
FIG. 5 shows a schematic diagram of the construction of the targeting gene vector, pAL10.

The present invention relates to a transgenic non-human animal lacking native MC-3R protein (MC-3R null; MC-3R$^{-/-}$), heterozygous transgenic non-human animals and to transgenic animals having a non-native MC-3R protein expressed either in the presence or absence of the native MC-3R, as well as MC-3R deficient transgenic animals. To this end, the present invention relates to animal cells which are homozygous for an MC-3R deficiency due to a disruption in the gene(s) encoding MC-3R, as well as to non-human transgenic embryos, non-human transgenic animals and non-human transgenic littermates which are MC-3R deficient (MC-3R null) due to a disruption in the gene(s) encoding MC-3R. The present invention also extends to animal cells, non-human transgenic embryos, non-human transgenic animals and non-human transgenic littermates which are heterozygous for a functional MC-3R gene native to that animal. In addition, the present invention relates to animal cells, non-human transgenic embryos and non-human transgenic littermates having a non-native gene encoding a MC-3R protein expressed either in the presence or absence of the native (wild type) MC-3R. Preferably, the non-native MC-3R gene is the human MC-3R gene.

The present invention also relates to transgenic embryos, non-human transgenic embryos, non-human transgenic animals and non-human transgenic littermates which are either homozygous, heterozygous or hemizygous for deletion of at least a portion of the MC-3R gene in combination with a homozygous, heterozygous or hemizygous deletion at separate alleles which in their wild type form encode at least one additional melanocortin receptor, especially a melanocortin receptor shown to be involved in body weight regulation, such as MC-4R. Therefore, aspects of the invention relate to transgenic embryos, non-human transgenic embryos, non-human transgenic animals and non-human transgenic littermates which are MC-3R$^{-/+}$/MC4R$^{-/-}$; MC-3R$^{-/+}$/MC-4R$^{-/+}$; MC-3R$^{-/-}$/MC4R$^{-/+}$, as well as hemizygous alternatives in reference to the two separate alleles. An especially preferred aspect of the present invention relates to MC-3R$^{-/-}$/MC-4$^{-/-}$ double knockout mice and related transgenic embryos, non-human transgenic embryos, non-human transgenic animals and non-human transgenic littermates.

The transgenic animal of the invention can be used in the study of the effect of modulators on the expression and activity of the MC-3R gene and/or protein in the regulation of body weight and muscle mass as defined by lean body mass, including but not limited to disorders such as obesity, diabetes, anorexia, cachexia, cancer, male and female sexual dysfunction, pain, memory, neuronal regeneration and neuropathy, growth disorders relating to reduced GH, IGF1 function, treatment of reduced lean body mass as it occurs in the frail elderly, and other states that are characterized as resulting from GH deficiency, cancer cachexia, disorders associated with depression and anxiety. The transgenic non-human animals of the present invention can also be used to study behavioral disorders such as depression and anxiety as well as addictive behavior, such as addictive behavior associated with the chronic use of drugs such as morphine and cocaine. Therefore, the transgenic animal of the present invention may be utilized to determine the effect of certain modulators on the on the expression and activity of MC-3R, direct modulators of the activity of the MC-3R gene or protein, and aspects of disorders involving regulation of body weight.

The generation of MC-3R deficient transgenic non-human animals, including mice, aids in defining the in vivo function(s) of MC-3R, especially as related to the interaction of the MC-3R in the regulation of body weight, as well as other indications listed herein, including but not limited to obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immunemodulation, rheumatoid arthritis, learning memory, modulation of cytokine release, skin tanning, acne and other skin disorders, neuroregeneration and neuroprotective and cognitive and memory enhancement including the treatment of Alzheimer's disease. Additionally, MC-3R null animals can be used as a strain for the insertion of human MC-3R genes, and provides an animal model useful in the design and assessment of various approaches to modulating MC-3R activity and expression. Such modified transgenic non-human animals can also be used as a source of cells for cell culture. These cells can be used for corresponding in vitro studies of MC-3R expression, activity and the modulation thereof.

An aspect of this invention is a method to obtain an animal in which the cells lack a functional MC-3R gene native to the animal. The method includes providing a gene for an altered form of the MC-3R gene native to the animal in the form of a transgene and targeting the transgene into a chromosome of the animal at the place of the native MC-3R gene or at another chromosomal location. The transgene can be introduced into the embryonic stem cells by a variety of methods known in the art, including electroporation, microinjection, and lipofection. Cells carrying the transgene can then be injected into blastocysts which are then implanted into pseudopregnant animals. In alternate embodiments, the transgene-targeted embryonic stem cells can be co-incubated with fertilized eggs or morulae followed by implantation into females. After gestation, the animals obtained are chimeric founder transgenic animals. The founder animals can be used in further embodiments to cross with wild-type animals to produce F1 animals heterozygous for the altered MC-3R gene. In further embodiments, these heterozygous animals can be interbred to obtain the viable transgenic embryos whose somatic and germ cells are homozygous for the altered MC-3R gene and thereby lack a functional MC-3R gene. In other embodiments, the heterozygous animals can be used to produce cells lines. In preferred embodiments, the animals are mice.

A further aspect of the present invention is a transgenic non-human animal which expresses a non-native MC-3R on a native MC-3R null background. In particular embodiments, the null background is generated by producing an animal with an altered native MC-3R gene that is non-functional, i.e. a knockout. The animal can be heterozygous (i.e., having a different allelic representation of a gene on each of a pair of chromosomes of a diploid genome), homozygous (i.e., having the same representation of a gene on each of a pair of chromosomes of a diploid genome) for the altered MC-3R gene, hemizygous (i.e., having a gene represented on only one of a pair of chromosomes of a diploid genome), or homozygous for the non-native MC-3R gene. In preferred embodiments, the animal is a mouse. In particular embodiments the non-native MC-3R gene can be a wild-type or mutant allele, preferably a wild-type or mutant human allele. In further embodiments the non-native MC-3R gene is operably linked to a promoter. As used herein, operably linked is used to denote a functional connection between two elements whose orientation relevant to one another can vary. In this particular case, it is understood in the art that a promoter can be operably linked to the coding sequence of a gene to direct the expression of the coding sequence while placed at various distances from the coding sequence in a genetic construct. Further embodiments are cell lines and cells derived from animals of this aspect of the invention.

An aspect of this invention are transgenic animals having a transgene including a non-native MC-3R gene on a native MC-3R null background. The method includes providing transgenic animals of this invention whose cells are heterozygous for a native gene encoding a functional MC-3R protein and an altered native MC-3R gene. These animals are crossed with transgenic animals of this invention that are hemizygous for a transgene including a non-native MC-3R gene to obtain animals that are both heterozygous for an altered native MC-3R gene and hemizygous for a non-native MC-3R gene. The latter animals are interbred to obtain animals that are homozygous or hemizygous for the non-native MC-3R and are homozygous or heterozygous for the altered native MC-3R gene. In particular embodiments, cell lines are produced and cells isolated from any of the animals produced in the steps of the method.

The transgenic animals and cells of this invention are useful in the determination of the in vivo function of a non-native MC-3R in regulation of body weight. The animals are also useful in determining the ability for various forms of wild-type and mutant alleles of a non-native MC-3R to rescue the native MC-3R null deficiency. The animals are also useful for identifying and studying the ability of a variety of compounds to act as modulators of the expression or activity of a non-native MC-3R in vivo, or by providing cells for culture, for in vitro studies.

The genetic information received by the animal can cause the native gene to become non-functional to produce a "knockout" animal. Alternatively, the genetic information received by the animal can be foreign to the species of animal to which the recipient belongs, or foreign only to the particular individual recipient. In the last case, the information can be altered or it can be expressed differently than the native gene.

The non-human transgenic animals of the present invention include non-human mammalian species, including but not limited to transgenic mice, transgenic rats, transgenic guinea pigs, transgenic rabbits, transgenic goats, transgenic non-human primates, such as chimpanzees, rhesus monkeys and green african monkeys, and transgenic cattle. Transgenic mice are preferred and exemplified herein.

The present invention especially relates to analysis of the complex function(s) of MC-3R as related to obesity and diabetes by generating knock-out transgenic mice and studying how various potential modulators interact within these manipulated animals. As described herein in more detail, the native wild type gene is selectively inactivated in totipotent ES cells (such as those described herein) and used to generate the transgenic mice of the present invention. Techniques are available to inactivate or alter any genetic region to any mutation desired by using targeted homologous recombination to insert specific changes into chromosomal alleles. It has not been known to date whether a mouse MC-3R knock out could be produced. Therefore, the present invention relates to diploid animal cells, non-human transgenic embryos, non-human transgenic animals and non-human transgenic littermates which are heterozygous or homozygous for a disrupted MC-3R gene resulting in deficient production of the MC-3R protein. The cells, embryos and non-human transgenic animals contain two chromosome alleles for MC-3R wherein at least one of the MC-3R alleles is mutated such that less than wild-type levels of MC-3R activity is produced. The diploid mouse cell, embryo or non-human transgenic mice homozygous for a disrupted MC-3R gene may show at least from about 50% to about 100% reduction in MC-3R activity compared to a wild type diploid cell. The diploid mouse cell, embryo or non-human transgenic mice heterozygous for a disrupted MC-3R gene may show at least from about 10% to about 100% reduction in MC-3R activity compared to a wild type diploid cell. It is within the purview of the artisan of ordinary skill to use known molecular biology techniques to measure the level of transcription, expression and/or functional MR-3R activity in mouse cell homozygous, heterozygous or hemizygous for a mutated MC-3R gene. Therefore, the present invention especially relates to analysis of the complex function(s) of MC-3R as related to obesity by generating homozygous, heterozygous or hemizygous transgenic mice and studying how various potential modulators interact within these manipulated animals. In a preferred embodiment, the assay is performed by providing an animal of the present invention, exposing the animal to the compound, and measuring the effect of said compound on body weight and other related biochemical and physiological responses. The measurement can be compared to these measurements in a genetically similar or identical animal that is not exposed to the compound. One way to facilitate such measurements would be to feed both MC-3R knock-out and wild-type mice a high fat diet to promote obesity (diet induced obesity [DIO]). After becoming obese, effects of potential MC-3R agonists may be measured for reduction of body fat in wild-type mice as opposed to no effect in MC-3R knock-out mice. Similar protocols may be useful in studying the effects of MC-3R modulators in other related disorders, such as diabetes. It will therefore be within the purview of the artisan to utilize the non-human transgenic animals of the present invention to study any number of complex events associated with modulation of the MC-3R. As additional examples, but in no way presented as limitations, the potential role of MC-3R in sexual dysfunction may be studied, in light of the fact that MC-3R is expressed in the lumbar and sacral spinal cord including lamina X, a key center for signaling to the penis. As noted herein, the MC-3R$^{-/-}$ "knock out" mice of the present invention may be used to study diseases and disorders such as the effect of modulators on the expression and activity of the MC-3R gene and/or protein in the regulation of body weight and muscle mass as defined by lean body mass, including but not limited to disorders such as obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/ sleep disorder, substance abuse, pain, male and female sexual dysfunction (including impotence, loss of libido and erectile dysfunction), fever, inflammation, immunemodulation, rheumatoid arthritis, learning memory, modulation of cytokine release, skin tanning, acne and other skin disorders, neuroregeneration and neuroprotective and cognitive and memory enhancement including the treatment of Alzheimer's disease, anorexia, cachexia, pain, memory, neuronal regeneration and neuropathy, growth disorders relating to reduced GH, IGF1 function, treatment of reduced lean body mass as it occurs in the frail elderly, and other states that are characterized as resulting from GH deficiency, cancer cachexia, disorders associated with depression and anxiety, and behavioral disorders such as depression and anxiety as well as addictive behavior, such as addictive behavior associated with the chronic use of drugs such as morphine and cocaine.

Figure 13A:
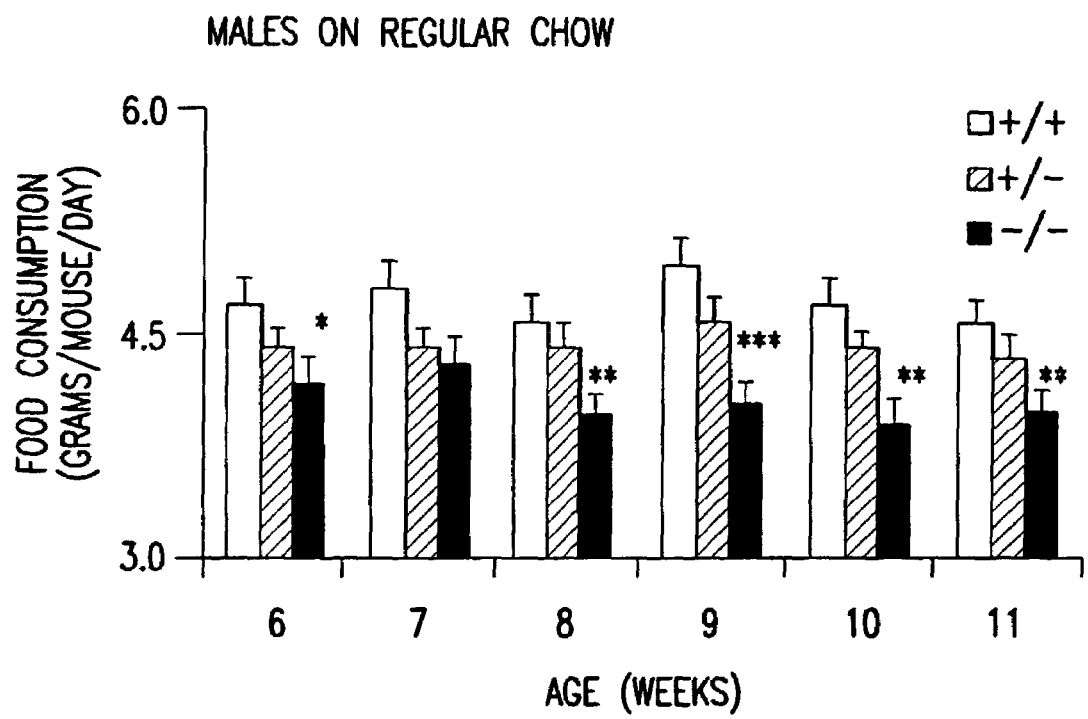
FIGS. 13A-F show food intake, weight gain, and feed efficiency of individually-housed male wild-type (+/+, n=11), heterozygous mutant [MC-3R$^{-/+}$] (+/-, n=20), and homozygous mutant [MC-3R$^{-/-}$] (-/-, n=16) littermate mice were maintained on a regular chow diet. Mice were separated into individual cages at ~1 month of age and food intake was measured weekly over a 8-week period. (A) Daily food intake calculated weekly. The average daily food intake for a 6-week period is shown in the inset in the top right corner. (B) Percent weight gain relative to the starting body weight. (C) Feed efficiency was calculated as biweekly weight gain divided by the corresponding biweekly food intake. Female wild-type (+/+, n=11), heterozygous mutant [MC-3R$^{-/+}$] (+/-, n=7), and homozygous mutant [MC-3R$^{-/-}$](-/-, n=10) littermate mice were separated into individual cages and placed on a high fat diet at ~1 month of age. (D) The average daily food intake for a 10-week period. (E) Percent weight gain relative to the starting body weight. (F) Feed efficiency was calculated as biweekly weight gain divided by biweekly food intake (-/- vs. +/+, P=0.001; at 7 weeks of age). All values are mean ±s.e.m. Statistics were performed with a two-tailed unpaired Student's t-test. All P-values are from comparison between MC-3R$^{-/-}$ and wild-type mice. * P<0.05,  P<0.01, *P<0.001.
Figures 1, 13A:
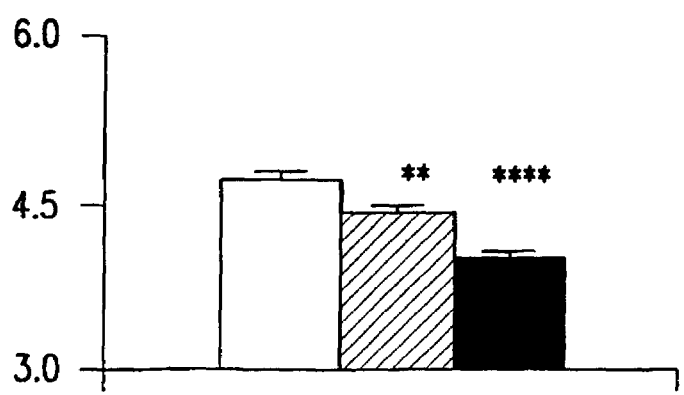
FIG. 1 shows the nucleotide sequence which encodes the murine MC-3R (SEQ ID NO:1).

The murine MC-3R gene (FIG. 1, SEQ ID NO:1, see Desarnaud, et al., 1994, Biochem. J. 299 (2): 367-373) comprises an open reading frame of 969 nucleotides (from nucleotide 110 to 1078, with a "TAG" termination codon from nucleotides 1079-1081) which expresses a protein 323 amino acids in length (FIG. 2, SEQ ID NO:). This DNA molecule relates to the open reading frame of the MC-3R gene associated with the preferred target host, *Mus musculus* (house mouse).

The nucleotide sequence comprising the murine MC-3R gene (FIG. 1, SEQ ID NO:1) is as follows:

```
                                              (SEQ ID NO:1)
TCTAGACTGG ACAGCATCCA CAAGAGAAGC ACCTAGAAGG

AGAATTTTCC CCAGCAGCTT GCTCAGGACC CTGCAGGAGC

CGCAGCTGGG ACTGGACCTG CTGTTAACCA TGAACTCTTC

CTGCTGCCTG TCTTCTGTTT CTCCGATGCT GCCTAACCTC

TCTGAGCACC CTGCAGCCCC TCCTGCCAGC AACCGGAGCG

GCAGTGGGTT CTGTGAGCAG GTCTTCATCA AGCCGGAGGT

CTTCCTGGCT CTGGGCATCG TCAGTCTGAT GGAAAACATC

CTGGTGATCC TGGCTGTGGT CAGGAATGGC AACCTGCACT

CTCCCATGTA CTTCTTCCTG TGCAGCCTGG CTGCAGCCGA

CATGCTGGTG AGCCTGTCCA ACTCCCTGGA GACCATCATG

ATCGCCGTGA TCAACAGCGA CTCCCTGACC TTGGAGGACC

AGTTTATCCA GCACATGGAT AATATCTTCG ACTCTATGAT

TTGCATCTCC CTGGTGGCCT CCATCTGCAA CCTCCTGGCC

ATTGCCATCG ACAGGTACGT CACCATCTTC TATGCCCTTC
```

```
                    -continued
GGTACCACAG CATCATGACA GTTAGGAAAG CCCTCACCTT

GATCGGGGTC ATCTGGGTCT GCTGCGGCAT CTGCGGCGTG

ATGTTCATCA TCTACTCCGA GAGCAAGATG GTCATCGTGT

GTCTCATCAC CATGTTCTTC GCCATGGTGC TCCTCATGGG

CACCCTATAT ATCCACATGT TCCTCTTCGC CAGGCTCCAC

GTCCAGCGCA TCGCAGTGCT GCCCCCTGCT GGCGTGGTGG

CCCCACAGCA GCACTCCTGC ATGAAGGGGG CTGTCACCAT

CACTATCCTG CTGGGTGTTT TCATCTTCTG CTGGGCGCCT

TTCTTCCTCC ACCTGGTCCT CATCATCACC TGCCCCACCA

ATCCCTACTG CATCTGCTAC ACGGCCCATT TCAACACCTA

CCTGGTTCTC ATCATGTGCA ACTCCGTCAT CGACCCCCTC

ATCTACGCCT TCCGCAGCCT GGAGCTGCGC AACACGTTCA

AGGAGATTCT CTGCGGCTGC AACAGCATGA ACTTGGGCTA

GGATGCCCGT GGAGGTGTTC CACATCCAGC CAAGAGACAA

AAACAACGCT CAGACGGGAC GTAAAAGGGT GTTAGGAGCT

GGAACTGTGC TTGGCTTCGT CTGTAAGCTC GTGGCCCTTT

GCAGACGGGA CACGGCGTAG GATGGGCTGT CTGTGAGGAT

CTGTGTGTGG GTAAGTCAGT TTGATCTAGC ACATAGCCTG

GAAGAATCAG GCAAAGCAGC CCTGAGTGTC ATCTGTGTTC

ATTGCTAGGC ACCCAGGGTT TGTGGCCCCT GCCTGCTTAT

TGGCTTTGTA CCAGTAACTG TGCTTCAAGC CAACCAGACC

GGAGGGCTCT CGTGAGCAGA AAGAGTGCTT AGACTTCCGG

CAAGCATCCT GGCTCACAGC GGCCACCTCC TGACCACTAC

CGGGAGAGCT TTGCACATAT TCTGTGGGAG ATTGAGTGAA

GCCCTGAAAA CAATGTGATA TTTGCTGCTC CCTTCCAGAA

CTTACATCTG TGCCAGCCTC CCCGAACCCC TGCACAGAGA

CATGACCCCC TTCTCCCTGT GCCGTTGTCA TGGTTGTTAT

TATTGTTGGA GTTTTGTTCG TTAAAATCTA AGCTT.
```

The amino acid sequence of the murine MC-3R is as follows:

```
                              (FIG. 2, SEQ ID NO:2)
MNSSCCLSSV SPMLPNLSEH PAAPPASNRS GSGFCEQVFI

KPEVFLALGI VSLMENILVI LAVVRNGNLH SPMYFFLCSL

AAADMLVSLS NSLETIMIAV INSDSLTLED QFIQHMDNIF

DSMICISLVA SICNLLAIAI DRYVTIFYAL RYHSIMTVRK

ALTLIGVIWV CCGICGVMFI IYSESKMVIV CLITMFFAMV

LLMGTLYIHM FLFARLHVQR IAVLPPAGVV APQQHSCMKG

AVTITILLGV FIFCWAPFFL HLVLIITCPT NPYCICYTAH

FNTYLVLIMC NSVIDPLIYA FRSLELRNTF KEILCGCNSM

NLG.
```

A MC-3R gene that naturally occurs in the animal is referred to as the native gene, and if it is not mutant, it can also be referred to as wild-type. An altered MC-3R gene should not fully encode the same MC-3R as native to the host animal, and its expression product can be altered to a minor or greater degree, or absent altogether. In cases where it is useful to express a non-native MC-3R gene in a transgenic animal in the absence of a native MC-3R gene we prefer that the altered MC-3R gene induce a null knockout phenotype in the animal. However a more modestly modified MC-3R gene can also be useful and is within the scope of the present invention. The MC-3R mutation may be a targeted deletion mutation, a targeted substitution mutation and/or a targeted insertion mutation. However, the preferred mutation is a deletion mutation, and especially preferred is a deletion mutation which results in a deletion of most if not all of the MC-3R gene. Transgenic animals are generated which have an altered, or preferably, completely deleted MC-3R gene. MC-3R gene deletions, gene modifications and or gene insertions can render the native gene nonfunctional, producing a "knockout" transgenic animal, or can lead to a MC-3R with altered expression or activity. As noted above, a non-human transgenic animal without an activated MC-3R gene can be used to evaluate the role of MC-3R in obesity and other associated disorders. The MC-3R protein is a G-protein coupled receptor comprising a ligand-binding extracellular domain, 7 transmembrane domains and an intracellular domain which couples to activation of adenyl cyclase. Melanocortin receptors belong to the rhodopsin sub-family of GPCR's. However, several features in the MC-3R are shared with all other receptors and are absent in most other GPCR's, including the EN motif in TM1, the lack of Cys in the loop between TM2 and TM3 or between TM4 and TM5, the MxxxxxxxY motif in TM5, and the DPxxY motif in TM7. Since all melanocortin receptors lack Cys residues in the extracellular loops that are present in other members of the rhodopsin sub-family, interhelical disulfide bond (e.g., between the Cys residues near the top of TM3 and TM5) may play the same function as interloop disulfide bond in most other GPCR's. Such known characteristics are useful in targeting specific host MC-3R mutations. A preferred deletion mutation may contain a deletion of anywhere from 1 nucleotide to deletion of the entire gene, including the open reading frame and associated cis-acting regulatory sequences associated with wild type MC-3R. A smaller deletion within the open reading frame is preferably not divisible by three, so as to result in a frameshift mutation resulting in a protein which most likely is non-functional. It is preferred that any such smaller deletion not divisible by three be targeted toward the 5' region of the open reading frame to increase the possibility of generating a non-functional truncated protein product. However, as noted above, it is preferable that the deletion mutation encompass most if not all of the MC-3R gene so as to ensure prevention of expression of a functional MC-3R protein.

The transgenic animals which are homozygous, heterozygous or hemizygous for a deficient MC-3R gene are useful for identifying compounds which modulate wild type MC-3R activity or expression in vivo and studying aspects of the regulation of body weight which may be imparted through activation or antagonism of the MC-3R receptor. The generation of MC-3R deficient transgenic non-human animals, including mice, aids in defining the in vivo function(s) of MC-3R. In addition, transgenic animals can be used as a strain for the insertion of human MC-3R genes and provides an animal model useful in the design and assessment of various approaches to modulating MC-3R activity and expression. An altered MC-3R gene should not fully encode the same MC-3R as native to the host animal, and its expression product can be altered to a minor or great degree, or absent altogether. However a more modestly modified MC-3R gene can also be useful and is within the scope of the present invention. The modified cells, embryos and/or non-human transgenic animal of the present invention can also be used as a source of cells for cell culture. These cells can be used for corresponding in vitro studies of MC-3R expression, activity and the modulation thereof. The non-human transgenic animals disclosed herein are useful for drug antagonist or agonist studies, for animal models of human diseases, and for testing of treatment of disorders or diseases associated with MC-3R. Transgenic animals lacking native MC-3R are useful in characterizing the in vivo function(s) of MC-3R. A transgenic animal carrying a non-native MC-3R in the absence of native MC-3R is useful for the establishment of a non-human model for diseases involving MC-3R, such as obesity, for studies of non-native MC-3R, to study modulators of the non-native gene and to distinguish between the activities of the non-native MC-3R in in vivo and in vitro systems.

In view of the teachings within this specification, it is within the purview of the artisan of ordinary skill to utilize antisense RNA transgenes, ribozymes or other modulators of RNA expression or other means of modulating MC-3R RNA production including promoter mutations, and mutations that affect transcription, to partially or totally knock out expression of the mouse MC-3R protein. The antisense transgene used herein would encode a polynucleotide which is at least partially complementary to all or a part of the host MC-3R gene and which will hybridize to a target sequence encoded by the host MC-3R gene, most specifically a mRNA transcript expressed from the host MC-3R gene. Any such oligonucleotide sequence should be at least about 15 to 30 nucleotides in length and preferably more than about 30 nucleotides, wherein this sequence is substantially complementary to the target host gene. The antisense transgene need not be a total complement, but instead should contain adequate sequence identity such that the expressed antisense RNA transgene will effective hybridize with the expressed mRNA from the host target gene so as to efficiently inhibit concomitant protein expression. These antisense polynucleotides may be produced by subcloning the sequence of interest into an appropriate gene expression vector and transferring this vector to pluripotent embryonic stem cells which may be used as described herein to generate another form of an MC-3R deficient non-human transgenic animal.

A type of target cell for transgene introduction is also the embryonic stem cell (ES). ES cells can be obtained from pre-implantation embryos cultured in vitro and fused with embryos (Evans et al., 1981, *Nature* 292: 154-156; Bradley et al., 1984, *Nature* 309: 255-258; Gossler et al., 1986, *Proc. Natl. Acad. Sci. USA* 83: 9065-9069; and Robertson et al., 1986, *Nature* 322: 445-448). Transgenes can be efficiently introduced into the ES cells by a variety of standard techniques such as DNA transfection, microinjection, or by retrovirus-mediated transduction. The resultant transformed ES cells can thereafter be combined with blastocysts from a non-human animal. The introduced ES cells thereafter colonize the embryo and contribute to the germ line of the resulting chimeric animal (Jaenisch, 1988, *Science* 240: 1468-1474). The use of gene-targeted ES cells in the generation of gene-targeted transgenic mice was described in 1987 (Thomas et al., *Cell* 51:503-512, (1987)) and is reviewed elsewhere (Frohman et al., *Cell* 56:145-147 (1989); Capecchi, *Trends in Genet.* 5:70-76 (1989); Baribault et al., *Mol. Biol. Med.* 6:481-492, (1989); Wagner, *EMBO J.* 9:3025-3032 (1990); Bradley et al., *Bio/Technology* 10:534-539 (1992)). See also, U.S. Pat. No. 5,464,764, issued to Cappecchi and Thomas on Nov. 7, 1995; U.S. Pat. No. 5,789,215, issued to Berns et al on Aug. 4, 1998, both of which are hereby incorporated by reference). Therefore, techniques are available in the art to generate the MC-4R deficient animal cells, non-human transgenic embryos, non-human transgenic animals and non-human transgenic littermates of the present invention. The methods for evaluating the targeted recombination events as well as the resulting knockout mice are also readily available and known in the art. Such methods include, but are not limited to DNA (Southern) hybridization to detect the targeted allele, polymerase chain reaction (PCR), polyacrylamide gel electrophoresis (PAGE), in situ hybridization and Western blots to detect DNA, RNA and protein.

Therefore, the MC-3R deficient animal cells, non-human transgenic embryos, non-human transgenic animals and non-human transgenic littermates of the present invention may be generated by any techniques known in the all, as sampled in the previous paragraph.

The generation of MC-3R knockout mouse has not been reported and it was not evident that a MC-3R knockout mouse would have any phenotype. The essence of the present invention relates to the demonstration that MC-3R knockout mice are obese, indicating the involvement of this receptor in the development of obesity, thus lending various assays described herein useful in selecting for modulators of MC-3R which effect body weight as well as related treatments for various body weight disorders. The MC-3R knockout mice of the present invention have increased fat mass (~45% at ~5 month of age; controls ~22% as determined by DEXA analysis). The finding that the MC-3R is involved in the regulation of body fat will allow testing of selected compounds (MC-3R agonist) for direct measurements of their efficiency to modulate (decrease) body fat, thus assessing their therapeutic potential for the treatment of obesity. As noted above, it had not been clear until now that the melanocortin-3 receptor is involved in development of obesity.

The MC-3R knock out targeting vector may be generated by methods known in the art. A mouse genomic DNA library was screened with a rat MC-3R probe. A 17 Kb mouse genomic clone was isolated and a gene targeting vector consisting of an 1.8 Kb 5' sequence (short arm) and an 8.5 kb 3' sequence (long arm) with the pgk-neo gene for positive selection and HSV-tk gene for negative selection was constructed and designated pAL10. This linearized construct was electroporated into AB2.1 cells and cultured with G418/FIAU for positive and negative selections. Twenty four positive clones were selected for expansion and microinjection into blastocysts to generate chimeric mice. The linearized pAL10 was also electroporated into AB2.2 cells, with 12 positive clones being selected for expansion and microinjection. In total, 13 chimeric mice (60-100% coat color chimerism) have been generated from injecting targeted ES clones into the blastocysts. Test breeding showed germline transmission (agouti pups) from three lines. Oligonucleotide primers have been utilized to identify knockout and wild-type mice generated in the breeding program. A batch of 54 pups from the heterozygous mating were genotyped with 9 pups being knock-outs and, 27 heterozygous and 18 wild type. Body composition was measured by dual energy x-ray absorptiometry (DEXA; QDR 4500, Hologic, Inc., Waltham, Mass.), providing a noninvasive method for quantification of whole body and bone mineral content (Kelly et al., 1998, *Theory and Practice Appl. Radiat. Isol.* 49: 511-513; Wolden-Hanson et al., 1999, *Journal of Gerontology: Biological Sciences* 54A: B:99-107).

Therefore, the present invention is shown to provide a model system consisting of transgenic animals, especially MC-3R$^{-/-}$ mice, cells and assays that are useful in the study of aspects of the etiology of obesity as related to modulation of the MC-3R. The various assays are also useful for screening and selecting for compounds that have an effect on body weight regulation, the further study of these compounds and the possible administration of selected compounds to humans in order to regulate disorders which include but are not limited to obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, male and female sexual dysfunction (including impotence, loss of libido and erectile dysfunction), fever, inflammation, immune modulation, rheumatoid arthritis, skin tanning, neuroprotective and cognitive enhancement including the treatment of Alzheimer's disease, anorexia, cachexia, cancer, pain, memory, neuronal regeneration and neuropathy, growth disorders relating to reduced GH, IGF1 function, treatment of reduced lean body mass as it occurs in the frail elderly, and other states that are characterized as resulting from GH deficiency, depression, anxiety, compulsion, neuroses, insomnia/sleep disorder, substance abuse, male and female sexual dysfunction (including impotence, loss of libido and erectile dysfunction), fever, inflammation, immunemodulation, rheumatoid arthritis, learning memory, modulation of cytokine release, skin tanning, acne and other skin disorders, neuroregeneration and neuroprotective and cognitive and memory enhancement including the treatment of disorders associated with depression and anxiety, and behavioral disorders such as depression and anxiety as well as addictive behavior, such as addictive behavior associated with the chronic use of drugs such as morphine and cocaine. While the preferred subject is a human, other mammals may be an effective host for a compound or compounds identified through the components of the present invention, including but not limited to other mammals, especially mammals of domesticated veterinary use such as canine and feline species, farm animals such as bovine, ovine, porcine, equine, caprine, rodents and additional undomesticated mammals. The finding that the MC-3R is involved in the regulation of body fat will allow testing of selected MC-3R agonists for direct measurements of their efficiency to modulate (decrease) body fat, thus assessing their therapeutic potential for the treatment of obesity. MC-3R knockout mice can be used to test melanocortin receptor subtype-specific compounds.

The present invention also relates to transgenic embryos, non-human transgenic embryos, non-human transgenic animals and non-human transgenic littermates which are either homozygous, heterozygous or hemizygous for deletion of the MC-3R gene in combination with a homozygous, heterozygous or hemizygous deletion at separate alleles which in their wild type form encode at least one additional melanocortin receptor, especially a melanocortin receptor shown to be involved in body weight regulation, such as MC-4R. Therefore, aspects of the invention relate to transgenic embryos, non-human transgenic embryos, non-human transgenic animals and non-human transgenic littermates which are MC-3R$^{-/+}$/MC-4R$^{-/-}$; MC-3R$^{-/+}$/MC-4R$^{-/+}$; MC-3R$^{-/-}$/MC-4R$^{-/+}$, as well as hemizygous alternatives in reference to the two separate alleles. An especially preferred aspect of the present invention relates to MC-3R$^{-/-}$/MC-4R$^{-/-}$ double knockout mice and related transgenic embryos, non-human transgenic embryos, non-human transgenic animals and non-human transgenic littermates, such as those disclosed in Example Section 3. These MC3-R$^{-/-}$ MC-4R$^{-/-}$ double knockout mice are more obese (heavier) than MC-4R$^{-/-}$ knockout mice, indicating a potential additive or synergistic effect of MC-3R and MC-4R knockouts on body mass. A preferred aspect of the present invention relates to an MC3-R$^{-/-}$MC-4R$^{-/-}$ knockout non-human animal, such as a mouse, which may provide an improved model for obesity, diabetes, and other applications as disclosed herein as pertaining to a MC3-R$^{-/-}$ knockout mouse. The MC3-R$^{-/-}$MC4R$^{-/-}$ double knockout mice may provide for an improved model for the study of diseases and disorders disclosed herein as related to a MC3-R$^{-/-}$ single knockout mouse. Data disclosed herein show that MC-3R$^{-/-}$ serves a non-redundant role, when compared to MC-4R, in the regulation of energy homeostasis. In addition, the data also shows that MC-3R and MC-4R may work synergistically, suggesting that MC-3R$^{-/-}$×MC-4R$^{-/-}$ mice may serve as a better model than MC4R–/– mice for the treatment of obesity and the other related disease. Therefore, the MC3-R$^{-/-}$MC-4R$^{-/-}$ double knockout mouse can be used to screen and select compounds (modulators such as agonists or antagonists of MC3-R and/or MC-4R involved in the regulation of food intake, body composition and energy metabolism, allowing for the assessment or the therapeutic potential of such a modulator as well as the specificity for either pathway for the treatment of obesity. In addition, the MC3-R$^{-/-}$ $^{MC}$-4R$^{-/-}$ double knockout mice of the present invention can be used to measure the impact of modulation of other pathways in this genetic background, determining potential interactions between pathways involved in the control of body weight. More specifically, the MC3-R$^{-/-}$ MC-4R$^{-/-}$ double knockout mice of the present invention can be used screen for and select compounds which are dual modulators of the MC-3R and MC-4R receptors, namely a dual agonist or dual antagonist of both the MC-3R and MC-4R receptor.

Any in vitro or in vivo cell- and/or membrane-based assay described herein (utilizing the respective MC-3R and MC-4R receptor protein) may be used in conjunction with any of the disclosed transgenic animals, including but not limited to a MC-3R$^{-/-}$ knockout mouse and/or a MC3-R$^{-/-}$ MC-4R$^{-/-}$ double knockout mouse to select for these dual modulators, or any other compound which may modulate MC-3R and/or MC-4R, which may provide for an improved compound(s) useful in the treatment of the various disorders and diseases disclosed herein, namely obesity and sexual dysfunction. These double knockout mice are also useful to select for modulators (again, agonists or antagonists of MC3-R and/or MC-4R) involved in the regulation of other processes associated with disorders noted herein, which include but are not limited to obesity (by reducing appetite, increasing metabolic rate, reducing fat intake or reducing carbohydrate craving), diabetes mellitus, hypertension, hyperlipidemia, osteoarthritis, cancer, gall bladder disease, sleep apnea, depression, male and female sexual dysfunction (including impotence, loss of libido and erectile dysfunction), fever, inflammation, immune modulation, rheumatoid arthritis, skin tanning, neuroprotective and cognitive enhancement including the treatment of Alzheimer's disease anorexia, cachexia, cancer, pain, memory, neuronal regeneration and neuropathy, growth disorders relating to reduced GH, IGF1 function, treatment of reduced lean body mass as it occurs in the frail elderly, and other states that are characterized as resulting from GH deficiency, cancer cachexia, disorders associated with depression and anxiety, and behavioral disorders such as depression and anxiety as well as addictive behavior, such as addictive behavior associated with the chronic use of drugs such as morphine and cocaine.

The present invention also relates to cell- and membrane-based methods of identifying selective agonists and/or antagonists of mammalian MC-3R which affect the regulation of body weight through disorders including but not limited to obesity, diabetes, anorexia and cachexia. Therefore, an object of the present invention provides for MC-3R-based assays to select for modulators of this receptor protein which affect regulation of body weight through the various known disorders associated with regulation of body weight. The MC-3R modulators may be used to treat these body weight disorders, such as utilizing a MC-3R agonist to treat obesity or a MC-3R antagonist to treat anorexia. These assays are preferably cell-based assays whereby a DNA molecule encoding MC-3R is transfected or transformed into a host cell and this recombinant host cell is allowed to grow for a time sufficient to express MC-3R prior to use in various assays described herein. Alternatively, any "non-recombinant" cell line which has been genetically modified to overexpress MC-3R may also be utilized to screen and/or select for modulators of MC-3R useful in the treatment of body weight disorders. In addition, substantially purified membrane fractions from (1) a host cell transfected with a DNA expression vector coding for MC-3R or (2) a cell line genetically manipulated to overexpress MC-3R may be utilized to screen and/or select for modulators useful in the treatment of body weight disorders. To this end, it is a further object to provide for membrane preparations from these recombinant or genetically modified host cells for use in assays to screen and/or select for modulators of MC-3R activity associated with the regulation of body weight. Therefore, the present invention relates to methods of treating body weight disorders through administration of modulators which directly affect the MC-3R, modulators identified initially through these cell- or membrane-based screens and/or through assays utilizing the transgenic animals of the present invention.

Any polynucleotide sequence which encodes a functional MC-3R may be utilized in the recombinant cell and membrane-based assays of the present invention. A preferred polynucleotide for use in constructing an appropriate DNA expression vector is a DNA molecule which comprises the open reading frame for human MC-3R as set forth in SEQ ID NO:3 (see also FIG. 3) and disclosed in U.S. Pat. No. 5,622,860, issued to Yamada and Gantz on Apr. 22, 1997 and U.S. Pat. No. 5,703,220, issued to Yamada and Gantz on Dec. 30, 1997), as follows:

(SEQ ID NO:3; FIG. 3)
ATGAGCATCC AAAAGAAGTA TCTGGAGGGA GATTTTGTCT

TTCCTGTGAG CAGCAGCAGC TTCCTACGGA CCCTGCTGGA

GCCCCAGCTG GGATCAGCCC TTCTGACAGC AATGAATGCT

TCGTGCTGCC TGCCCTCTGT TCAGCCAACA CTGCCTAATG

GCTCGGAGCA CCTCCAAGCC CCTTTCTTCA GCAACCAGAG

CAGCAGCGCC TTCTGTGAGC AGGTCTTCAT CAAGCCCGAG

ATTTTCCTGT CTCTGGGCAT CGTCAGTCTG CTGGAAAACA

```
                                       -continued
TCCTGGTTAT CCTGGCCGTG GTCAGGAACG GCAACCTGCA

CTCCCCGATG TACTTCTTTC TCTGCAGCCT GGCGGTGGCC

GACATGCTGG TAAGTGTGTC CAATGCCCTG GACACCATCA

TGATCGCCAT CGTCCACAGC GACTACCTGA CCTTCGAGGA

CCAGTTTATC CAGCACATGG ACAACATCTT CGACTCCATG

ATCTGCATCT CCCTGGTGGC CTCCATCTGC AACCTCCTGG

CCATCGCCGT CGACAGGTAC GTCACCATCT TTTACGCGCT

CCGCTACCAC AGCATCATGA CCCTGAGGAA GGCCCTCACC

TTGATCGTGG CCATCTGGGT CTGCTGCGGC GTCTGTGGCG

TGGTGTTCAT CGTCTACTCG GAGAGCAAAA TGGTCATTGT

GTGCCTCATC ACCATGTTCT TCGCCATGAT GCTCCTCATG

GGCACCCTCT ACGTGCACAT GTTCCTCTTT GCGCGGCTGC

ACGTCAAGCG CATAGCAGCA CTGCCACCTG CCGACGGGGT

GGCCCCACAG CAACACTCAT GCATGAAGGG GGCAGTCACC

ATCACCATTC TCCTGGGCGT GTTCATCTTC TGCTGGGCCC

CCTTCTTCCT CCACCTGGTC CTCATCATCA CCTGCCCCAC

CAACCCCTAC TGCATCTGCT ACACTGCCCA CTTCAACACC

TACCTGGTCC TCATCATGTG CAACTCCGTC ATCGACCCAC

TCATCTACGC TTTCCGGAGC CTGGAATTGC GCAACACCTT

TAGGGAGATT CTCTGTGGCT GCAACGGCAT GAACTTGGGA,
``` which encodes the entire open reading frame of the MC-3R protein, set forth as SEQ ID NO:4 (see also FIG. 4), as follows:

```
                                           (SEQ ID NO:4)
MSIQKKYLEG DFVFPVSSSS FLRTLLEPQL GSALLTAMNA

SCCLPSVQPT LPNGSEHLQA PFFSNQSSSA FCEQVFIKPE

IFLSLGIVSL LENILVILAV VRNGNLHSPM YFFLCSLAVA

DMLVSVSNAL ETIMIAIVHS DYLTFEDQFI QHMDNIFDSM

ICISLVASIC NLLAIAVDRY VTIFYALRYH SIMTVRKALT

LIVAIWVCCG VCGVVFIVYS ESKMVIVCLI TMFFAMMLLM

GTLYVHMFLF ARLHVKRIAA LPPADGVAPQ QHSCMKGAVT

ITILLGVFIF CWAPFFLHLV LIITCPTNPY CICYTAHFNT

YLVLIMCNSV IDPLIYAFRS LELRNTFREI LCGCNGMNLG.
```

The DNA molecule set forth as SEQ ID NO:3 or a biologically equivalent polynucleotide may be inserted into an appropriate vector and linked with other DNA molecules, i.e., DNA molecules to which the MC-3R are not naturally linked, to form "recombinant DNA molecules" expressing the receptor. These vectors may be comprised of DNA or RNA; for most cloning purposes DNA vectors are preferred. Typical vectors include plasmids, modified viruses, bacteriophage and cosmids, yeast artificial chromosomes and other forms of episomal or integrated DNA that can encode a MC-3R. It is well within the purview of the skilled artisan to determine an appropriate vector for a particular use.

A variety of mammalian expression vectors may be used to express recombinant MC-3R in mammalian cells. As noted above, expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses. Commercially available mammalian expression vectors which may be suitable for recombinant MC-3R expression, include but are not limited to, pcDNA3.neo (Invitrogen), pcDNA3.1 (Invitrogen), pCI-neo (Promega), pLITMUS28, pLU-MUS29, pLITMUS38 and pLITMUS39 (New England Bioloabs), pcDNAI, pcDNAIamp (Invitrogen), pcDNA3 (Invitrogen), pMCIneo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and 1ZD35 (ATCC 37565).

Also, a variety of bacterial expression vectors may be used to express recombinant MC-3R in bacterial cells. Commercially available bacterial expression vectors which may be suitable for recombinant MC-3R expression include, but are not limited to pCR2.1 (Invitrogen), pET11a (Novagen), lambda gt11 (Invitrogen), and pKK223-3 (Pharmacia).

In addition, a variety of fungal cell expression vectors may be used to express recombinant MC-3R in fungal cells. Commercially available fungal cell expression vectors which may be suitable for recombinant MC-3R expression include but are not limited to pYES2 (Invitrogen) and *Pichia* expression vector (Invitrogen).

Also, a variety of insect cell expression vectors may be used to express recombinant receptor in insect cells. Commercially available insect cell expression vectors which may be suitable for recombinant expression of MC-3R include but are not limited to pBlueBacm and pBlueBacHis2 (Invitrogen), and pAcG2T (Pharmingen).

Expression of MC-3R DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the MC-3R cDNA sequence(s) that yields optimal levels of MC-3R, cDNA molecules including but not limited to the following can be constructed: a cDNA fragment containing the full-length open reading frame for MC-3R as well as various constructs containing portions of the cDNA encoding only specific domains of the protein or rearranged domains of the protein. All constructs can be designed to contain none, all or portions of the 5' and/or 3' untranslated region of a MC-3R cDNA. The expression levels and activity of MC-3R can be determined following the introduction, both singly and in combination, of these constructs into appropriate host cells. Following determination of the MC-3R cDNA cassette yielding optimal expression in transient assays, this MC-3R cDNA construct is transferred to a variety of expression vectors (including recombinant viruses), including but not limited to those for mammalian cells, plant cells, insect cells, oocytes, bacteria, and yeast cells.

The host cells engineered to contain and/or express DNA sequences encoding the MC-3R can be cultured under suitable conditions to produce MC-3R or a biologically equivalent form. Recombinant host cells may be prokaryotic or eukaryotic, including but not limited to, bacteria such as E. coli, fungal cells such as yeast, mammalian cells including, but not limited to, cell lines of human, bovine, porcine, monkey and rodent origin, and insect cells including but not limited to Drosophila and silkworm derived cell lines. Therefore, an expression vector containing DNA encoding a MC-3R-like protein may be used for expression of MC-3R in a recombinant host cell. Recombinant host cells may be prokaryotic or eukaryotic, including but not limited to bacteria such as E. coli, fungal cells such as yeast, mammalian cells including but not limited to cell lines of human, bovine, porcine, monkey and rodent origin, and insect cells including but not limited to Drosophila- and silkworm-derived cell lines. For instance, one insect expression system utilizes Spodoptera frugiperda (Sf21) insect cells (Invitrogen) in tandem with a baculovirus expression vector (pAcG2T, Pharmingen). Also, mammalian species which may be suitable and which are commercially available, include but are not limited to, L cells L-M(TK$^-$) (ATCC CCL 1.3), L cells L-M (ATCC CCL 1.2), Saos-2 (ATCC HrTB-85), 293 (ATCC CRL 1573), Raji (ATCC CCL 86), CV-1 (ATCC CCL 70), COS-1 (ATCC CRL 1650), COS-7 (ATCC CRL 1651), CHO-K$^1$ (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171) and CPAE (ATCC CCL 209). The expression vector may be introduced into host cells via any one of a number of techniques including but not limited to transformation, transfection, protoplast fusion, and electroporation. The expression vector-containing cells are individually analyzed to determine whether they produce MC-3R protein. Identification of MC-3R expressing cells may be done by several means, including but not limited to immunological reactivity with anti-MC-3R antibodies, labeled ligand binding and the presence of host cell-associated MC-3R activity.

In one embodiment of the present invention, assays described herein can be carried out with cells that have been genetically modified to overexpress host MC-3R, preferably resulting in at least a 5-fold increase over expression in a chosen "wild-type" host cell. Such improvements of overexpression can be brought about by any means presently known in the art, including but not limited to introducing a promoter by homologous recombination while leaving the coding region intact, or by simply selecting for cells that for whatever biological reason express a higher level of the MC-3R.

In another and preferred embodiment of the present invention, assays described herein can be carried out with cells that have been transiently or stably transfected or transformed with an expression vector which directs expression of MC-3R. The expression vector may be introduced into host cells via any one of a number of techniques including but not limited to transformation, transfection, protoplast fusion, and electroporation. Transformation is meant to encompass a genetic change to the target cell resulting from an incorporation of DNA. Transfection is meant to include any method known in the art for introducing MC-3R into the test cells. For example, transfection includes calcium phosphate or calcium chloride mediated transfection, lipofection, infection with a retroviral construct containing MC-3R, and electroporation. The expression vector-containing cells are individually analyzed to determine whether they produce MC-3R protein. Identification of MC-3R expressing cells may be done by several means, including but not limited to immunological reactivity with anti-MC-3R antibodies, labeled ligand binding and the presence of host cell-associated MC-3R activity.

The specificity of binding of compounds showing affinity for MC-3R is shown by measuring the affinity of the compounds for recombinant cells expressing the cloned receptor or for membranes from these cells. Expression of the cloned receptor and screening for compounds that bind to MC-3R or that inhibit the binding of a known, radiolabeled ligand of MC-3R to these cells, or membranes prepared from these cells, provides an effective method for the rapid selection of compounds with high affinity for MC-3R which may be useful in the treatment of body weight disorders. Such ligands need not necessarily be radiolabeled but can also be nonisotopic compounds that can be used to displace bound radiolabeled compounds or that can be used as activators in functional assays. Compounds identified by the above method are likely to be agonists or antagonists of MC-3R and may be peptides, proteins, or non-proteinaceous organic molecules, all of which may be useful in the treatment of body weight disorders.

The present invention is directed to methods for screening for compounds which modulate the expression of DNA or RNA encoding a MC-3R protein as well as compounds which effect the function of the MC-3R protein and hence, body weight disorders. Methods for identifying agonists and antagonists of other receptors are well known in the art and can be adapted to identify agonists and antagonists of MC-3R. For example, Cascieri et al. (1992, Molec. Pharmacol. 41:1096-1099) describe a method for identifying substances that inhibit agonist binding to rat neurokinin receptors and thus are potential agonists or antagonists of neurokinin receptors. The method involves transfecting COS cells with expression vectors containing rat neurokinin receptors, allowing the transfected cells to grow for a time sufficient to allow the neurokinin receptors to be expressed, harvesting the transfected cells and resuspending the cells in assay buffer containing a known radioactively labeled agonist of the neurokinin receptors either in the presence or the absence of the substance, and then measuring the binding of the radioactively labeled known agonist of the neurokinin receptor to the neurokinin receptor. If the amount of binding of the known agonist is less in the presence of the substance than in the absence of the substance, then the substance is a potential agonist or antagonist of the neurokinin receptor. Where binding of the substance such as an agonist or antagonist to MC-3R is measured, such binding can be measured by employing a labeled substance or agonist. The substance or agonist can be labeled in any convenient manner known to the art, e.g., radioactively, fluorescently, enzymatically. When screening for a modulator that antagonizes the target receptor (such as MC-3R and/or MC-4R) a cell-based assay may rely on the inclusion of a known ligand in combination with the test compound so as to measure the functional ability of the test compound to antagonize receptor activity. As noted herein, these cell-based and membrane-based assays may be utilized to screen and select lead compounds which possess an ability to modulate both the MC-3R and MC-4R receptor. These dual modulators, as either agonists or antagonists of both receptors, arguably may provide for an improved compound for treating maladies associated with both receptors, such as disorders associated with the regulation of body weight, as described herein.

Therefore, the specificity of binding of compounds having affinity for MC-3R is shown by measuring the affinity of the compounds for recombinant cells expressing the cloned receptor or for membranes from these cells. Expression of the cloned receptor and screening for compounds that bind to MC-3R or that inhibit the binding of a known, radiolabeled ligand of MC-3R to these cells, or membranes prepared from these cells, provides an effective method for the rapid selection of compounds with high affinity for MC-3R. Such ligands need not necessarily be radiolabeled but can also be nonisotopic compounds that can be used to displace bound radiolabeled compounds or that can be used as activators in functional assays. Compounds identified by the above method are likely to be agonists or antagonists of MC-3R and may be peptides, proteins, or non-proteinaceous organic molecules which may be useful for human administration to treat various maladies, including but in no way limited to obesity (by reducing appetite, increasing metabolic rate, reducing fat intake or reducing carbohydrate craving), diabetes mellitus, hypertension, hyperlipidemia, osteoarthritis, cancer, gall bladder disease, sleep apnea, depression, male and female sexual dysfunction (including impotence, loss of libido and erectile dysfunction), fever, inflammation, immune modulation, rheumatoid arthritis, skin tanning, neuroprotective and cognitive enhancement including the treatment of Alzheimer's disease, anorexia, cachexia, cancer, pain, memory, neuronal regeneration and neuropathy, growth disorders relating to reduced GH, IGF1 function, treatment of reduced lean body mass as it occurs in the frail elderly, and other states that are characterized as resulting from GH deficiency, cancer cachexia, disorders associated with depression and anxiety, and behavioral disorders such as depression and anxiety as well as addictive behavior, such as addictive behavior associated with the chronic use of drugs such as morphine and cocaine. Compounds may modulate by increasing or attenuating the expression of DNA or RNA encoding MC-3R, or by acting as an agonist or antagonist of the MC-3R receptor protein. These compounds that modulate the expression of DNA or RNA encoding MC-3R or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample. Kits containing MC-3R, antibodies to MC-3R, or modified MC-3R may be prepared by known methods for such uses.

To this end, the present invention relates in part to methods of identifying a substance which modulates MC-3R receptor activity, which involves:

(a) combining a test substance in the presence and absence of a MC-3R receptor protein, including but not limited to the MC-3R proteins comprising the amino acid sequence as set forth in SEQ ID NO:2, and/or SEQ ID NO:4; and (b) measuring and comparing the effect of the test substance in the presence and absence of the MC-3R receptor protein.

In addition, several specific embodiments are disclosed herein to show the diverse type of screening or selection assay which the skilled artisan may utilize in tandem with an expression vector directing the expression of the MC-3R receptor protein. Methods for identifying agonists and antagonists of other receptors are well known in the art and can be adapted to identify agonists and antagonists of MC-3R. Therefore, these embodiments are presented as examples and not as limitations. To this end, the present invention includes assays by which MC-3R modulators (such as agonists, inverse agonists and antagonists) may be identified. Accordingly, the present invention includes a method for determining whether a substance is a potential agonist or antagonist of MC-3R useful in the treatment of body weight disorders, comprising:

(a) transfecting or transforming cells with an expression vector that directs expression of MC-3R in the cells, resulting in test cells;

(b) allowing the test cells to grow for a time sufficient to allow MC-3R to be expressed;

(c) exposing the cells to a labeled ligand of MC-3R in the presence and in the absence of the substance; and, (d) measuring the binding of the labeled ligand to MC-3R; where if the amount of binding of the labeled ligand is less in the presence of the substance than in the absence of the substance, then the substance is a potential agonist or antagonist of MC-3R.

The conditions under which step (c) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. The test cells may be harvested and resuspended in the presence of the substance and the labeled ligand. In a modification of the above-described method, step (c) is modified in that the cells are not harvested and resuspended but rather the radioactively labeled known agonist and the substance are contacted with the cells while the cells are attached to a substratum, e.g., tissue culture plates.

The present invention also includes a method for determining whether a substance is capable of binding to MC-3R or a mutant MC-3R that is no longer functional but nonetheless may be involved in ligand binding, i.e., whether the substance is a potential agonist, inverse agonist or an antagonist of MC-3R and hence useful in the treatment of body weight disorders, where the method comprises:

(a) transfecting or transforming cells with an expression vector that directs the expression of MC-3R in the cells, resulting in test cells;

(b) exposing the test cells to the substance;

(c) measuring the amount of binding of the substance to MC-3R;

(d) comparing the amount of binding of the substance to MC-3R in the test cells with the amount of binding of the substance to control cells that have not been transfected with MC-3R;

wherein if the amount of binding of the substance is greater in the test cells as compared to the control cells, the substance is capable of binding to MC-3R. Determining whether the substance is actually an agonist or antagonist can then be accomplished by the use of functional assays such as, e.g., the assay involving the use of promiscuous G-proteins described below.

The conditions under which step (b) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. The test cells are harvested and resuspended in the presence of the substance.

Chen et al. (1995, *Analytical Biochemistry* 226: 349-354) describe a colorimetric assay which utilizes a recombinant cell transfected with an expression vector encoding a G-protein coupled receptor with a second expression vector containing a promoter with a cAMP responsive element fused to the LacZ gene. Activity of the overexpressed G-protein coupled receptor is measured as the expression and OD measurement of B-Gal. Therefore, another aspect of this portion of the invention includes a non-radioactive method for determining whether a substance is a potential agonist or antagonist of MC-3R that comprises:

(a) transfecting or transforming cells with an expression vector encoding MC-3R, resulting in test cells;

(b) transfecting or transforming the test cells of step (a) with an expression vector which comprises a cAMP-inducible promoter fused to a colorimetric gene such a LacZ;

(c) allowing the transfected cells to grow for a time sufficient to allow MC-3R to be expressed;

(d) harvesting the transfected cells and resuspending the cells in the presence of a known agonist of MC-3R and/or in both the presence and absence of the test compound;

(e) measuring the binding of the known agonist and test compound to overexpressed MC-3R by a colorimetric assay which measures expression off the cAMP-inducible promoter and comparing expression levels in the presence of the known agonist as well as in the presence and absence of the unknown substance so as to determine whether the unknown substance acts as either a potential agonist or antagonist of MC-3R.

Additional methods of identifying MC-3R agonists or antagonists for use in treating body weight disorders include but are by no means limited to the following:

I. (a) transfecting or transforming cells with a first expression vector which directs expression of MC-3R and a second expression vector which directs the expression of a promiscuous G-protein, resulting in test cells;

(b) exposing the test cells to a substance that is a suspected agonist of MC-3R;

(c) measuring the level of inositol phosphates in the cells; where an increase in the level of inositol phosphates in the cells as compared to the level of inositol phosphates in the cells in the absence of the suspected agonist indicates that the substance is an agonist of MC-3R.

II. (a) transfecting or transforming cells with a first expression vector of claim 3 which directs expression of MC-3R and a second expression vector which directs the expression of a promiscuous G-protein, resulting in test cells;

(b) exposing the test cells to a substance that is an agonist of MC-3R;

(c) subsequently or concurrently to step (b), exposing the test cells to a substance that is a suspected antagonist of MC-3R;

(d) measuring the level of inositol phosphates in the cells; where a decrease in the level of inositol phosphates in the cells in the presence of the suspected antagonist as compared to the level of inositol phosphates in the cells in the absence of the suspected antagonist indicates that the substance is an antagonist of MC-3R.

III. The method of II wherein the first and second expression vectors of step (a) are replaced with a single expression vector which expresses a chimeric MC-3R protein fused at its C-terminus to a promiscuous G-protein.

The above-described methods can be modified in that, rather than exposing the test cells to the substance, membranes can be prepared from the test cells and those membranes can be exposed to the substance. Such a modification utilizing membranes rather than cells is well known in the art and is described in, e.g., Hess et al., 1992, *Biochem. Biophys. Res. Comm.* 184:260-268. Accordingly, another embodiment of the present invention includes a method for determining whether a substance binds and/or is a potential agonist or antagonist of MC-3R wherein membrane preparations from the test cells are utilized in place of the test cells. Such methods comprise the following and may utilized the physiological conditions as noted above:

(a) transfecting or transforming cells with an expression vector that directs the expression of MC-3R in the cells, resulting in test cells;

(b) preparing membranes containing MC-3R from the test cells and exposing the membranes to a ligand of MC-3R under conditions such that the ligand binds to the MC-3R in the membranes;

(c) subsequently or concurrently to step (b), exposing the membranes from the test cells to a substance;

(d) measuring the amount of binding of the ligand to the MC-3R in the membranes in the presence and the absence of the substance;

(e) comparing the amount of binding of the ligand to MC-3R in the membranes in the presence and the absence of the substance where a decrease in the amount of binding of the ligand to MC-3R in the membranes in the presence of the substance indicates that the substance is capable of binding to MC-3R.

The present invention also relates to a method for determining whether a substance is capable of binding to MC-3R comprising:

(a) transfecting or transforming cells with an expression vector that directs the expression of MC-3R in the cells, resulting in test cells;

(b) preparing membranes containing MC-3R from the test cells and exposing the membranes from the test cells to the substance;

(c) measuring the amount of binding of the substance to the MC-3R in the membranes from the test cells;

(d) comparing the amount of binding of the substance to MC-3R in the membranes from the test cells with the amount of binding of the substance to membranes from control cells that have not been transfected with MC-3R, where if the amount of binding of the substance to MC-3R in the membranes from the test cells is greater than the amount of binding of the substance to the membranes from the control cells, then the substance is capable of binding to MC-3R.

A preferred embodiment of the present invention is determining various ligand binding affinities using $^{125}$I-labeled NDP-α-MSH as the labeled ligand in the presence of varying concentration of unlabeled ligands. The activation of the second messenger pathway may be determined by measuring the intracellular cAMP elicited by agonist at various concentration.

It will be within the scope of the invention to submit screened compounds which show an in vitro modulation effect on MC-3R to in vivo analysis, preferably by administering the compound of interest to either a transgenic or wild-type animal as described herein to measure in vivo effects of the compound on the MC-3R receptor and to further measure biological and physiological effects of compound administration on the non-human animal. These in vivo studies may be done either alone or in combination with a known MC-3R ligand, such as but not limited to α-MSH, the agouti protein or the agouti like protein. For example, the MC-3R KO and wild-type mice can be used for in vivo testing of candidate compounds for their effects on several different parameters such as food intake, body weight, body composition, glucose, insulin, leptin and cholesterol levels, sexual function, memory, learning, nerve regeneration, pain. In order to facilitate such measurement relating to body weight and diabetes both knockout and wild-type mice can be made DIO (diet-induced obesity) first before being subjected to compound testing. Therefore, the comparison of the effects on wild-type, knock-out and heterozygote mice is an essential component of the evaluation of the selectivity of said compounds.

It is also an essential part of the present invention to measure sensitivity to other melanocortin or other pathways that may have been up or down regulated and the measure changes in sensitivity of compounds that modulate these pathways. To this end, testing of compounds that affect MC-4R, or other melanocortin receptors, NPY receptors, galanin receptors, MCH receptors, Insulin receptors, Orexin receptors, receptors belonging to the bombesin family of receptors (BRS-3, neuromedin receptors, gastrin releasing peptide receptors), motilin receptors, neuromedin U receptors, adrenergic receptors, leptin receptors, modulators of STATs and SOCs transcription factors, phoshpodiesterase enzymes and others are within the scope of uses for the non-human transgenic animals of the present invention, including but not limited to transgenic mice homozygous, heterozygous or hemizygous for an altered native MC-3R gene and transgenic mice homozygous, heterozygous or hemizygous for the double knock-out of the MC-3R and MC-4R native genes, as described herein and exemplified in Example 3. To this end, a preferred aspect of the present invention relates to the selection of compounds which are shown to modulate either the MC-3R and/or MC-4R receptor, which may be initially identified through the in vitro cell and/or membrane based assays by targeting the MC-3R and/or the MC-4R. Of course, such an MC-4R based assay may be utilized as described herein for MC-3R, as is well known in the art (see, e.g. U.S. Pat. No. 5,932,779, issued Aug. 3, 1999 to Lee et al.; Huszar et al., 1997, *Cell* 88: 131-141). Any such compound may be further studied by administering to a transgenic mouse which has been altered in the MC-4R and/or MC-3R gene(s) and measuring biological characteristics such as disclosed herein for the MC-3R and MC-3R/MC-4R altered mice of the present invention.

Pharmaceutically useful compositions comprising modulators of MC-3R may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, modified MC-3R, or either MC-3R agonists or antagonists.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The following examples are presented by the way of illustration and, because various other embodiments will be apparent to those in the art, the following is not to be construed as a limitation on the scope of the invention.

EXAMPLE 1

Construction of MC-3R Targeting Vector

Figure 6:
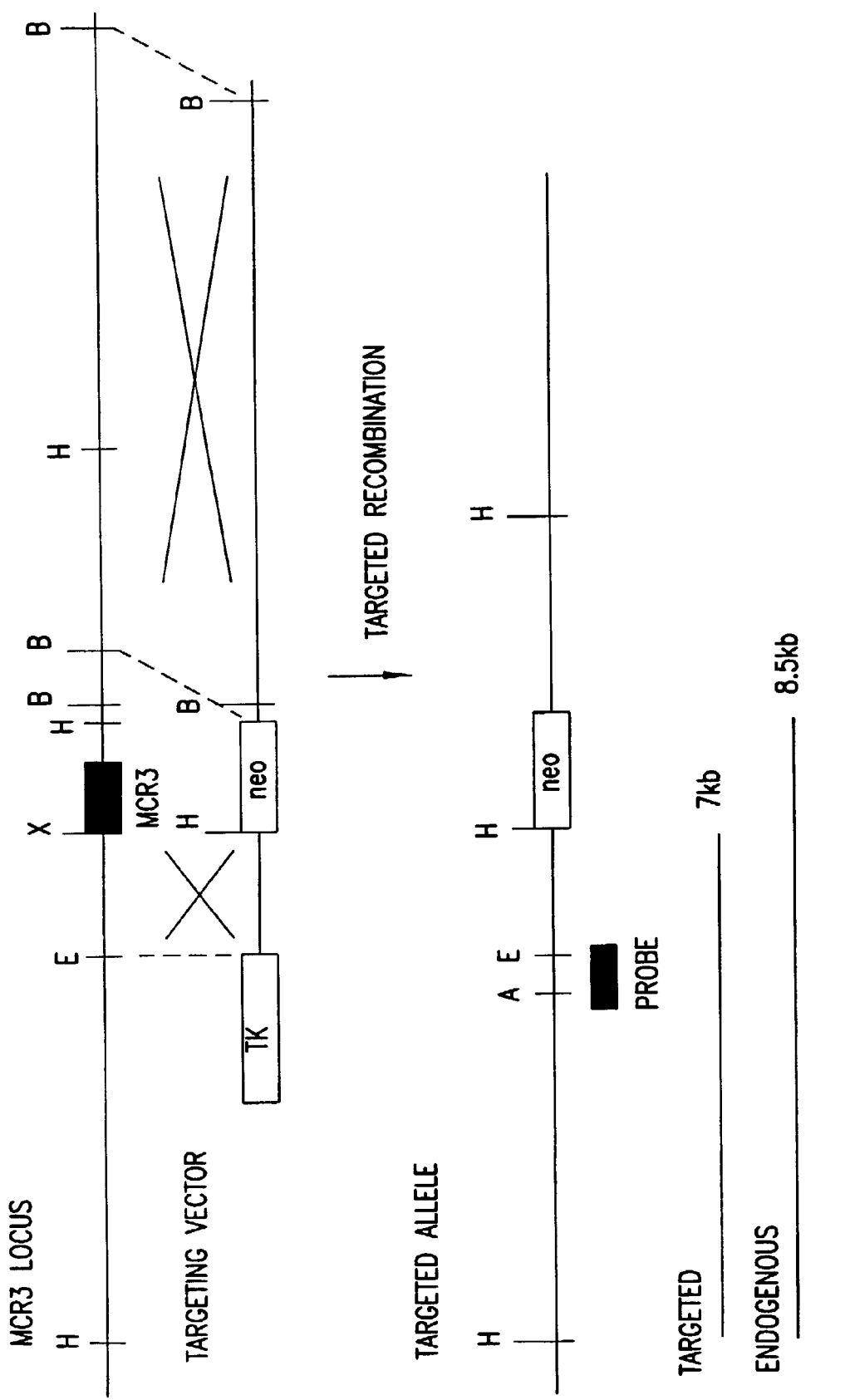
FIG. 6 shows the strategy utilizing the targeting gene vector, pAL10, for homologous recombination with mouse genomic sequences encoding MC-3R.

To isolate genomic DNA containing murine MC3-R gene, a mouse129$_{sjv}$, lambda genomic library (Lambda FIX II Library, Stratagene, La Jolla, Calif.) was screened using a 1 Kb rat MC-3R PCR product as a probe. This probe corresponds to the full length rat MC-3R coding region. A 17 Kb Sal I mouse genomic clone was isolated and subcloned into pBluescriptII KS(−) and is designated pAL-1. Digestion with several restriction enzymes which cleave in the coding region indicates this 17 Kb SalI restriction fragment contains MC-3R coding sequence with 3 Kb of the 5' flanking region and 13 Kb of the 3' flanking region. The vector pAL-1 was digested with SalI/XbaI and this 5' 3.0 Kb fragment was subcloned into SalI/XbaI digested pBluescriptII KS(−) and designated pAL-2. The vector pAL-1 was also digested with BamHI and the resulting 8.5 Kb fragment representing the 3' arm was subcloned into BamHI-digested pBluescriptII KS(−) vector to generate SacII and ClaI sites for subsequent directional cloning. The resulting clone was designated pAL-5. An EcoRI-XbaI fragment representing the 5' arm was removed from pAL-2 and ligated with pGEM-9Zf to generate a 3' HindIII site, resulting in pAL-6. The herpes simplex virus thymidine kinase (tk) gene (as a negative selection marker in the targeting vector) was also digested with XbaI and HindIII and cloned into pSP72 to generate a KpnI (5') and a PvuII (3') site for further cloning. This clone was designated pAL7. The pKO scrambler vector 918 (purchased from Lexicon Genetics, also distributed by Stratagene) was used to serve as the backbone for generating the targeting vector. An 1.8 kb EcoRI-HindIII fragment was removed from pAL6 and a 1.7 Kb HindIII-SacII fragment was removed from PGK-Neo (neomycin phosphotransferase gene under the control of the phosphoglycerokinase promoter [pPGKneobpA, obtained from Dr. Alan Bradely; also see e.g., Tybulewicz et al., 1991, *Cell* 65:1153-1163). Both fragments were ligated into Eco RI/Sac II digested-pKO V918 by three-parts ligation. The resulting clone is termed pAL8. To subclone the thymidine kinase (tk) gene into the targeting vector, a 2.0 KpnI-PvuII fragment was removed from pAL7 and was ligated into pAL8 (digested by HpaI and KpnI), resulting in pAL-9. In order to insert the 3' (long) arm into this vector, pAL9 and pAL5 digestion with SacII and ClaI was necessary. However, ClaI could not digest the pAL9 vector due to DNA methylation by dam$^+$*E. Coli* strain(DH5a) and there was another unexpected SacII site residing in the 3' end of TK gene. To overcome this first problem, the pAL9 plasmid was transformed into dam$^-$/dcm$^{-1}$ *E. Coli* strain(DM1). Partial restriction digestion was utilized to avoid cutting the unexpected SacII site in pAL9. After subcloning the 8.5 Kb SacII-ClaI fragment from pAL5 into pAL9, the MC-3R targeting vector was designated as pAL10, Several restriction enzymes such as BamHI, EcoRI, HindIII, NotI, SacII, SalI and XbaI were used to confirm the identity of this targeting vector. An approximately 500 bp ApaI-EcoRI fragment outside the targeting vector in the 5' sequence was tested as a probe and found suitable for screening the targeted ES cell clones and gene knockout mice described in Example Section 2. The schematic diagram for the generation of pAL10 is shown in FIG. 5 and the overall targeting strategy for deleting murine MC-3R genomic sequences is shown in FIG. 6.

EXAMPLE 2

Generation of MC-3R Knockout Mice

Figure 7A:
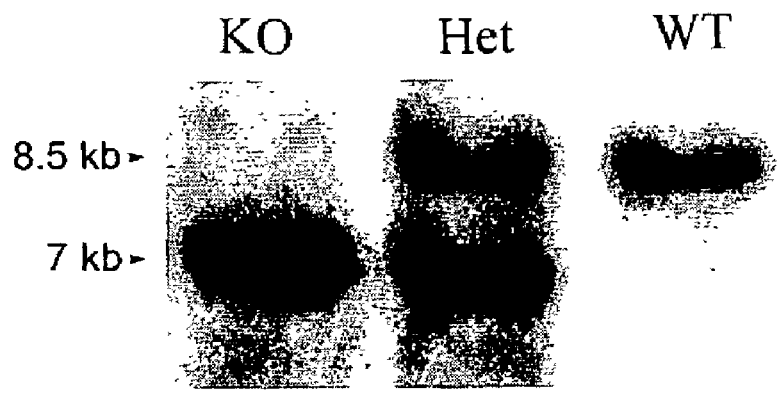
FIGS. 7A and 7B shows Southern hybridization (FIG. 7A) and PCR analysis (FIG. 7B) of homozygous and heterozygous MC-3R transgenic mice and wild-type mice generated in the breeding program.
Figure 7B:
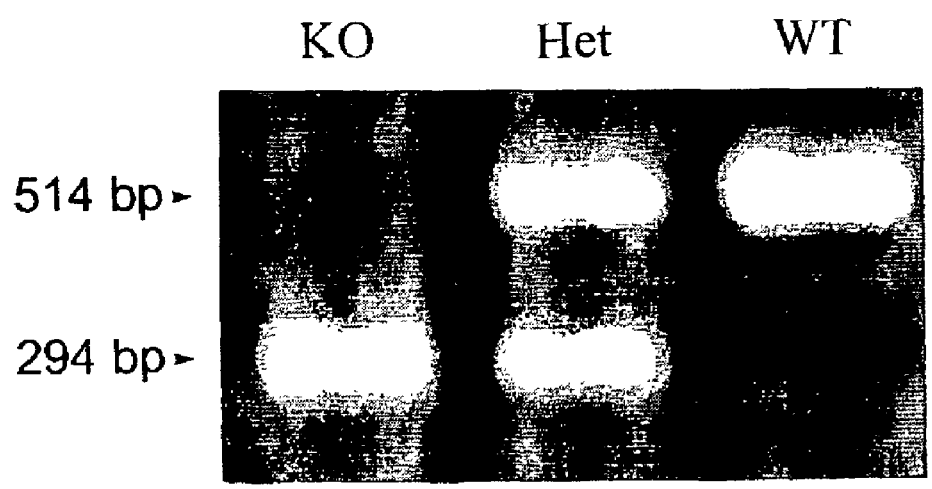

Animal care and maintenance—All animal protocols used herein were approved by the Merck Research Laboratories Institutional Animal Care and Use Committee in Rahway, N.J. Mice were group—or individually—housed in microisolation cages (Labproducts™) in a barrier animal facility with an air shower entrance or in an SPF animal facility (for high fat diet or MTII studies). Mice were maintained on either Teklad 7012 (regular mouse chow) or Teklad 97070 (high fat diet) (Harlan Teklad, Madison, Wis.) with ad libitum access to water. Electroporation was performed with 1×10$^7$ AB2.1 cells and 25 µg of linearized pAL10 under standard conditions using Bio-Rad Gene Pulser. These cells were cultured with G418/FIAU for positive and negative selections. About 800 resistant clones were selected from AB2.1 cells. Southern blot analysis revealed very high targeting efficiency (about one in five). Twenty four clones were selected for expansion and microinjection into blastocysts to generate chimeric mice. Clones 3D8, 4C10 and 4E4 produced good chimeras. Electroporation of linearized pAL10 was also performed in AB2.2 cells. AB2.1 ES cells were derived from line 129sv mouse (e.g., see Zheng, et al., 1995, *Cell* 81: 525-531; Zheng, et al., 1995, *Immunity* 3: 9-19; Wang, et al., 1997, *Nature* 387: 288-291; Von Koch, et al., 1997, *Neurobiology of Aging* 18: 661-669). AB2.2 ES cells were also derived from line 129sv mouse (available from Lexicon Genetics). About 800 resistant clones were selected for analysis. Southern blot results showed the targeting efficiency was about 1 in 13. Twelve clones were selected for expansion and microinjection. Clones 3A8, 3F5, 4G5 produced good chimeras. Thirteen chimeric mice (60-100% coat color chimerism) have been generated from injecting targeted ES clones into C57BU6J blastocysts. Three chimeras derived from three independent ES clones demonstrated germline transmission of the mutant allele. Test breeding showed germline transmission (agouti pups) from three lines. To facilitate the identification of knockout and wild-type mice generated in the breeding program, 3 primers were designed to distinguish the knockout allele from wild-type allele by PCR (FIG. 7B). The primers pairs will yield a 514 bp fragment for the wild-type MC-3R (+/+) mice, 294 bp and a 514 bp fragments for the MC-3R (−/+) heterozygous mice and a 294 bp fragment for the MC-3R knockout (−/−) mice. These PCR results were confirmed by the Southern blot analysis of the tail samples (FIG. 7A). An approximately 500 bp ApaI-EcoRI fragment located outside of the targeting vector on the 5' side was used as a probe to for screen the for correctly targeted ES cell clones and subsequent mutant mice. Targeted disruption of the MC-3R coding sequence with the PGK-neo cassette introduced an additional HindIII site. Consequently, this probe detected an ~8.5 Kb HindIII fragment from WT ES cells, whereas a smaller 7 Kb band was detected from ES cells containing the targeted MC-3R allele.

By using this strategy, a batch of 54 pups from the heterozygous mating were genotyped, as follows: nine were homologous knock outs, 27 were heterozygous and 18 were wild type. Heterozygous breeding pairs may be generated in order to produce sufficient number of progeny of similar age for various studies. Additional strategies using KO×KO and WT×VWT to mass-produce knock out and wild type mice may also be employed.

PCR Analysis of the Knockout Mice—To facilitate the identification of knockout and wild-type mice generated, 3 oligonucleotides were designed to distinguish the knockout allele from wild-type allele by PCR. The synthetic oligonucleotides 5'-GATGAGAGAAGACTG-GAGAGAGAGGGTC-3' (SEQ ID NO: 5) and 5'-GAA-GAAGTACATGGGAGAGTGCAGGTT-3'(SEQ ID NO:6) result in a 514 bp PCR product by the wild-type allele and 5'-GATGAGAGAAGACTGGAGGA GAGGGTC-3' (SEQ ID NO:7) and 5'-TACCGGTGGATGTGGAATGTGTGC-3'

(SEQ ID NO:8) result in a 294 bp PCR product by the mutant allele. The results are shown in FIG. 7B.

Figure 9:
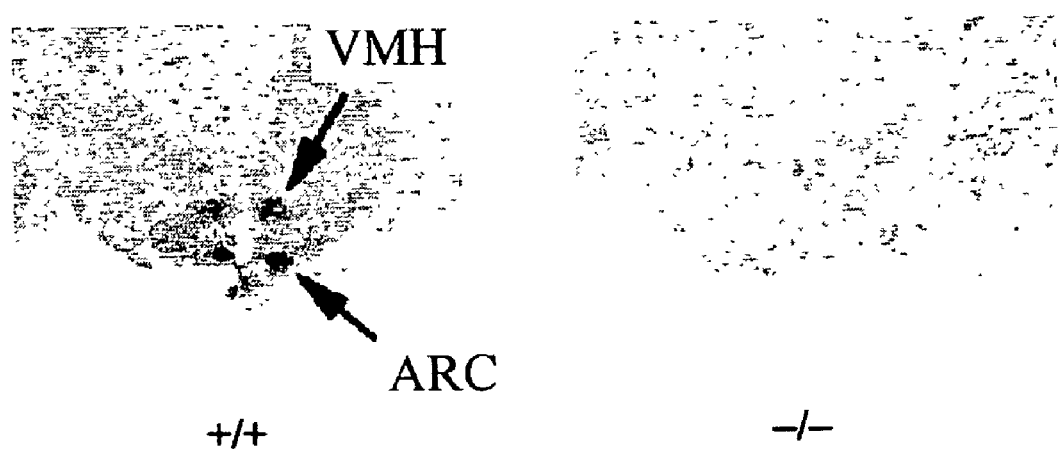
FIG. 9 shows absence of MC-3R mRNA expression in the hypothalamic arcuate (ARC) and ventromedial (VMH) nuclei of a MC-3R$^{-/-}$ mouse brain. In situ hybridization was performed on 14 μm coronal brain sections from wild-type (+/+) and MC-3R$^{-/-}$ (-/-)female mice.

In situ hybridization—MC3-R KO and age/sex matched wild-type control mice were killed by decapitation, and brains were quickly removed and frozen in −40° C. isopentane, and stored at −80° C. until use. Coronal brain sections (14 μM) were cut at −17° C. with a cryostat microtome, and thaw-mounted onto baked microslides. Following fixation in ice-cold 4% phosphate-buffered paraformaldehyde, the tissue sections were stored in 95% ethanol at 4° C. until use. The hybridization probes consist of an equal molar mixture of three non-overlapping, antisense oligonucleotides against the coding region of MC3-R. Their sequences are Oligo 282:5'-AGCCAGGATCACCAGGATGTTCCATCA-GACTGACGATGC CCAG-3'(SEQ ID NO:9); Oligo 345: 5'-TGCCCATGAGGAGCACCATGGCGA AGAACATG-GTGATGAGGCACA-3'(SEQ ID NO: 10); Oligo 346: 5'-ATGATGAGGACCAGGTGGAGGAAGAAAG-GCGCCCAGCAGAAGATG-3' (SEQ ID NO:11). The probes were terminally labeled with [α-$^{33}$P]dATP and terminal transferase, and hybridization and washing conditions were as described in detail in Guan, et al., 1997, *Brain Res Mol Brain Res* 48(1):23-9, 1997. MC-3R$^{-/-}$ mice. MC-3R$^{-/-}$ mice lacked detectable expression of MC-3R$^{-/-}$, whereas MC-3R$^{-/-}$ mRNA was readily detected in the hypothalamus of WT mice (FIG. 9).

Figure 8:
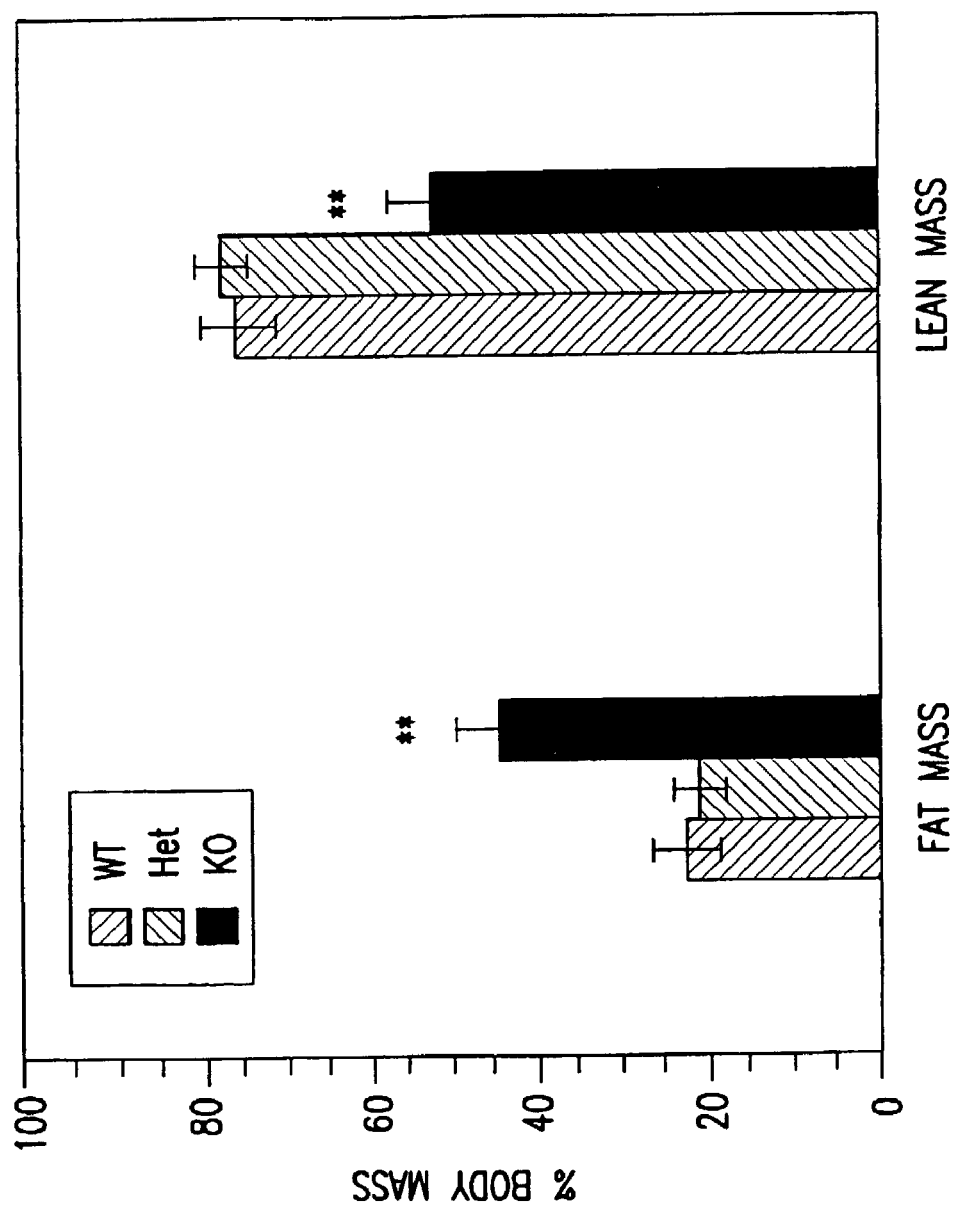
FIG. 8 shows the comparison of body composition of MC-3R knockout (N=8), heterozygous (N=7) and wild-type (N=5) mice. A group of male and female mice between 5 and 6 months old were subjected to DEXA scan to determine body composition. ** indicates P<0.01 when comparing knockout with wild-type mice.

Bodyfat determination by DEXA scan—Body composition was measured by dual energy x-ray absorptiometry (DEXA; QDR 4500, Hologic, Inc., Waltham, Mass.), providing a noninvasive method for quantification of whole body and bone mineral content (Kelly et al., 1998: Wolden-Hanson et al., 1999). This software is optimized for rats, but precision and sensitivity studies performed in mice demonstrated that this software can also be used to analyze whole body composition in mice (% CV obtained on repeated measurements on the same animal was below 1%). The QDR 4500 provides a noninvasive method for quantification of whole body and bone mineral content. The system is based on the differential attenuation of low and high energy x-rays by the tissues in the scan area. Energy is attenuated in proportion to tissue density, and this information is used by the detector and associated software, in conjunction with tissue calibration phantoms, to assess body composition. Fat mass consists primarily of adipose tissue, but lean mass includes organs, tendons, cartilage, blood, and body water in addition to skeletal muscle. 5.5 months old male mice were anesthetized with ketamine/xylazine for Dexascan analysis. The results are shown in FIG. 8, which contains data from both male and female mice). FIG. 8 shows that MC-3R knockout mice have increased fatmass (~45% at ~5 month of age; controls 22% as determined by DEXA analysis). As noted herein, the finding that the MC-3R is involved in the regulation of body fat will allow testing of selected compounds (MC-3R agonist) for direct measurements of their efficiency to modulate (decrease) body fat, thus assessing their therapeutic potential for the treatment of obesity. The finding that the MC-3R is involved in the regulation of body fat will allow testing of selected MC-3R agonists for direct measurements of their efficiency to modulate (decrease) body fat in a DIO model, thus assessing their therapeutic potential for the treatment of obesity. The MC-3R knockout mice described herein can be used to test melanocortin receptor subtype-specific compounds.

Biochemical Biochemical analysis of adipose tissue—The two inguinal white (WAT) and the two interscapular brown (BAT) fat pads were removed from 28-30-week old male MC-3R$^{-/-}$ and WT mice and weighed (WAT: MC-3R$^{-/-}$, 1.21±0.12 g vs WT, 0.55±0.06, P<0.0005, n=8; BAT:: MC-3R$^{-/-}$, 0.23±0.02 g vs WT, 0.15±0.01, P<0.006, n=8). Total nucleic acid was isolated by SDS/proteinase K digestion followed by phenol/chloroform extraction and isopropanol precipitation. DNA was dissolved and total content determined by absorbance at 260 nm. DNA content was determined by fluorescence of Hoechst 33258. RNA content was calculated from TNA minus DNA.

Food intake measurements—MC-3R$^{-/-}$, MC-3R$^{+/-}$, and WT mice were separated into individual microisolator cages at approximately one month of age. For studies involving regular mouse chow (Teklad 7012; 5% fat, 19% protein, and 5% of fiber; 3.75 grams/Kcal and 14.8% Kcal. from fat), pellet food was provided in wire cage tops containing food hoppers and food was weighed weekly. For studies involving a high fat diet (Teklad 97070; 33.5% fat, 27.4% protein, and 26.5% carbohydrates; 60% calories from fat), ground food was provided in a glass jar located in the cage and the jar containing the food was weighed either daily or weekly.

Peripheral MTII administration—For seven consecutive days, individually-housed 23-25-week-old male MC-3R$^{-/-}$ (n=9) and WT (n=9) mice received an intraperitoneal (ip) injection of a sterile 0.9% NaCl vehicle solution approximately 30 min before the onset of the dark phase of the light cycle. At the same time on the eighth consecutive day of the study, mice received an ip injection of MTII at a dose of 10 mg/kg delivered in vehicle. Body and food (Teklad 7012) weights were measured and recorded daily approximately 15 min prior to injection.

Plasma leptin, insulin, glucose and corticosterone measurements—Mice were fasted for 4 h priors to withdrawal of blood for leptin, insulin, glucose, triglyceride, and cholesterol measurements. Blood for leptin measurements was collected by heart puncture, whereas blood for the measurement of all other factors except corticosterone was collected from the retroorbital sinus. Prior to the collection of blood for plasma corticosterone and total T4 measurements, mice had ad libitum access to food and water. To prevent stress-mediated elevation of corticosterone levels, mice were immediately decapitated and trunk blood was collected into heparinized tubes. Plasma leptin and insulin were measured by RIA from Linco (Linco, St. Louis, Mo.), plasma corticosterone was measured by RIA from ICN (ICN, Biomedicals, Inc., Costa Mesa, Calif.), and plasma total T4 was measured by RIA from Diagnostic Products Co. (Diagnostic Products Co., Los Angeles, Calif.). Plasma glucose analyses were performed on a Boehringer Mannheim Hitachi 911 automated clinical chemistry analyzer (Boehringer Mannheim Corp., Indianapolis, Ind.).

Body temperature measurements—Body temperatures of individually-housed 25-27-week-old male and female MC-3R$^{-/-}$ (n=10-11) and WT (n=10-11) littermate mice were measured with a BAT-10 type T thermocouple thermometer and a RET-3 rectal probe for mice (Physitemp Instruments, Inc., Clifton, N.J.) during the mid-portion of the light phase of the light cycle.

Indirect calorimetry—Metabolic rate was measured by indirect calorimetry using a 16-chamber open-circuit Oxymax system (Columbus Instruments, Columbus, Ohio). Female 27-29-week-qld MC-3R$^{-/-}$ (29.5±2.0 g body weight; n=10) and WT (26.3±0.4 g body weight; n=10) littermate mice were maintained at 21 to 24° C. in a 12 hour light-dark cycle with food and water available ad libitum. Animals were individually-housed in specially built plexiglas cages (20 cm×10.5 cm×12 cm) through which room air was passed at a flow rate of 0.53 liter/min. Exhaust air from each chamber was sampled at 15 minute intervals for a period of 75 seconds. Sample air was sequentially passed through $O_2$ and $CO_2$ analyzers (Columbus Instruments) for determination of $O_2$ and $CO_2$ content. Metabolic rate (kcal/hr) was calculated from the following equation: $(3.815+1.232 \times RER) \times vO_2$ where RER is the respiratory exchange ratio [volume of $CO_2$ produced (ml/kg body weight/hour) per volume of $O_2$ consumed (ml/kg body weight/hour)] and $vO_2$ is the volume of $O_2$ consumed per hour.

Assessment of locomotor activity and fine movements—Locomotor activity and fine movements of individually-housed 21-23 week-old male and female MC-3R$^{-/-}$; n=10-11) and WT (n=10) littermate mice were evaluated with a cage rack Photobeam Activity System (San Diego Instruments, San Diego, Calif.). Mice were individually-housed in transparent plexiglass cages (40×20×20 cm) for several weeks prior to evaluation. Two consecutive photobeam breaks occurring in adjacent photobeams were scored as an ambulatory movement and two or more consecutive photobeam breaks occurring in the same photobeam, with no other photobeams being interrupted, were scored as fine movements. The total number of ambulatory movements in a given part of the light cycle was multiplied by the distance between two adjacent photobeams (0.053975 m) to yield the total distance traveled during that given part of the light cycle.

Figure 10A:
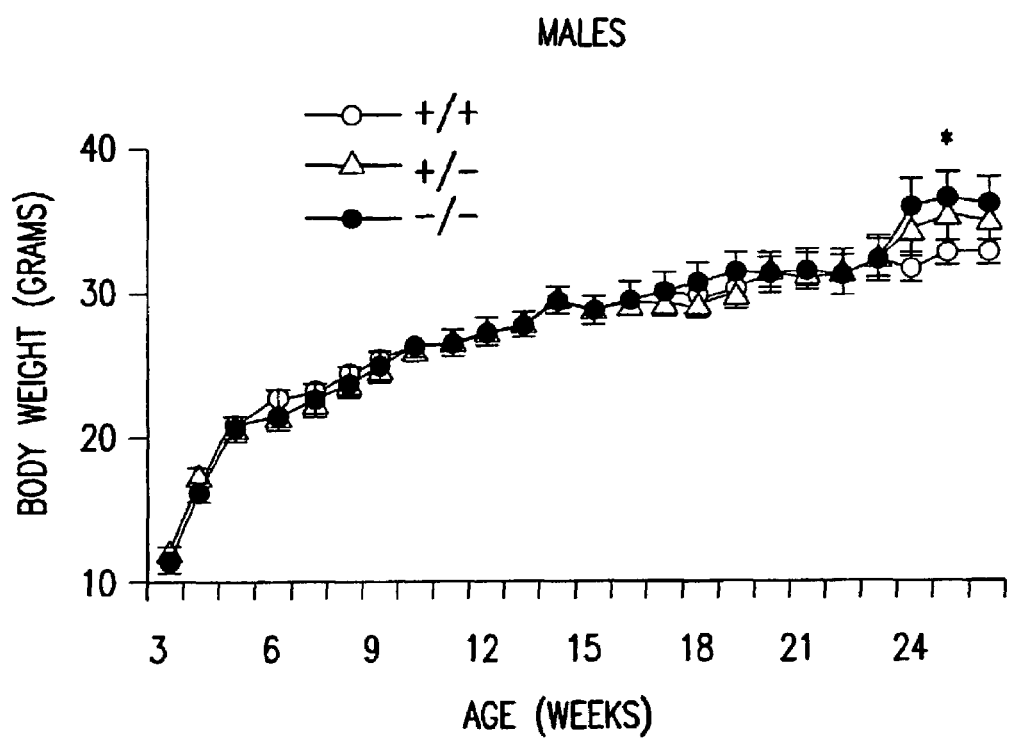
FIG. 10 A-D shown Growth curves (A,B) and body composition (C,D) of wild-type (+/+), heterozygous mutant (+/-), and homozygous mutant (-/-) littermate mice. Body weights of group-housed mice (males, n=11-37; females, n=11-31) were measured weekly. Body composition, including fat and lean body mass, was determined by DEXAscan of group-housed 15-17- and 26-27-week-old male (n=8-12) and female (n=8-13) F2 progeny. All values are mean ±s.e.m. Statistics were performed with a two-tailed unpaired Student's t-test. All P-values are from comparison between MC-3R$^{-/-}$ and wild-type mice. * P<0.05, ** P<0.01.
Figure 10B:
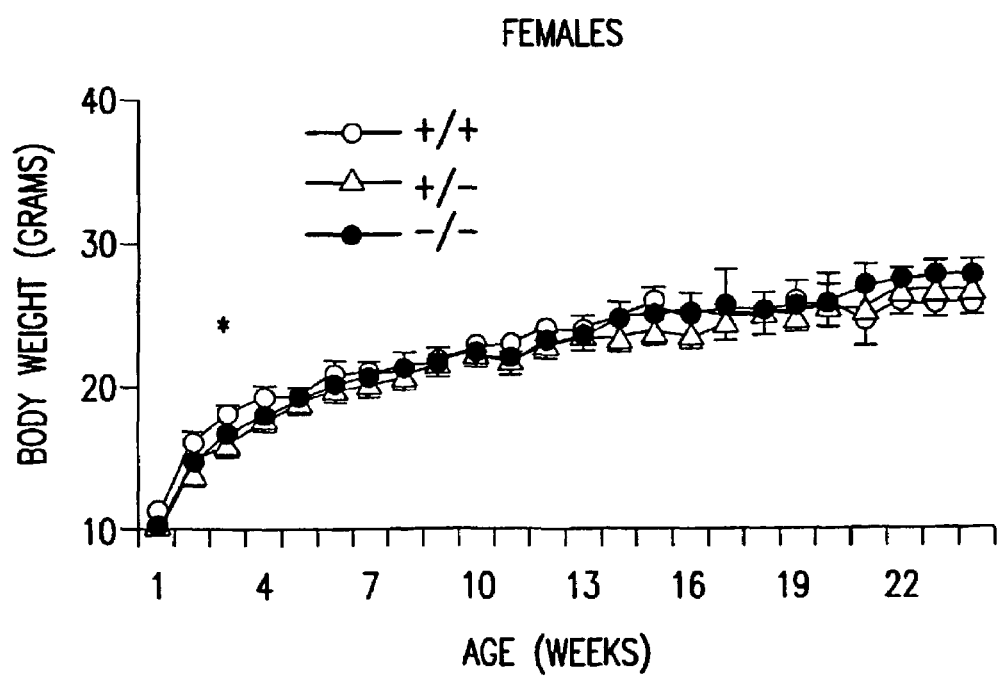
Figure 10C:
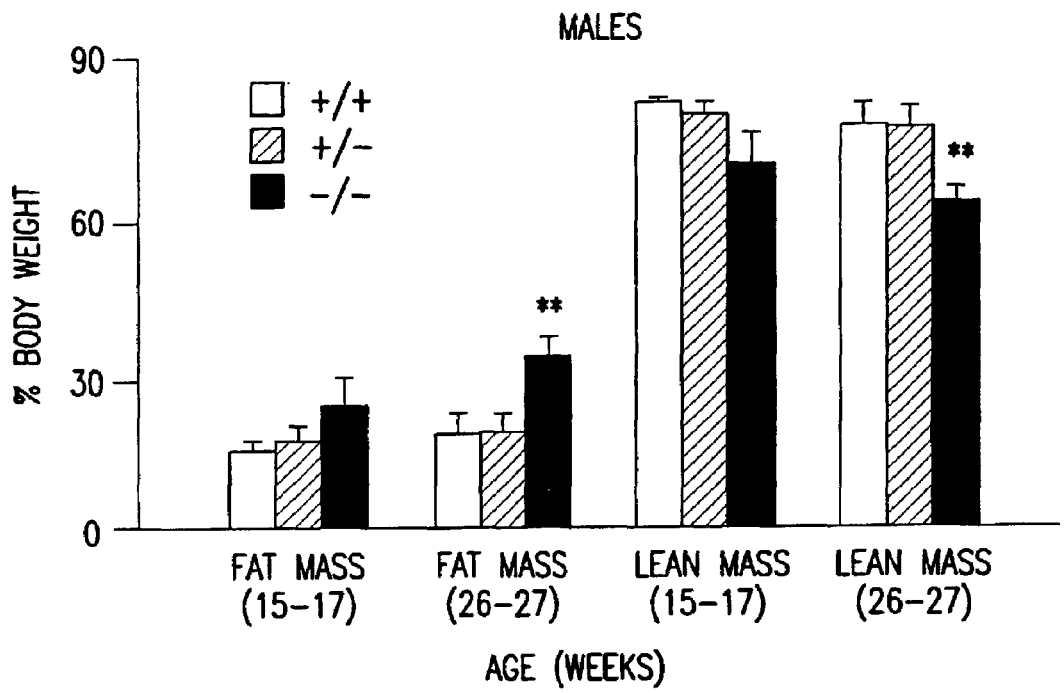
Figure 10D:
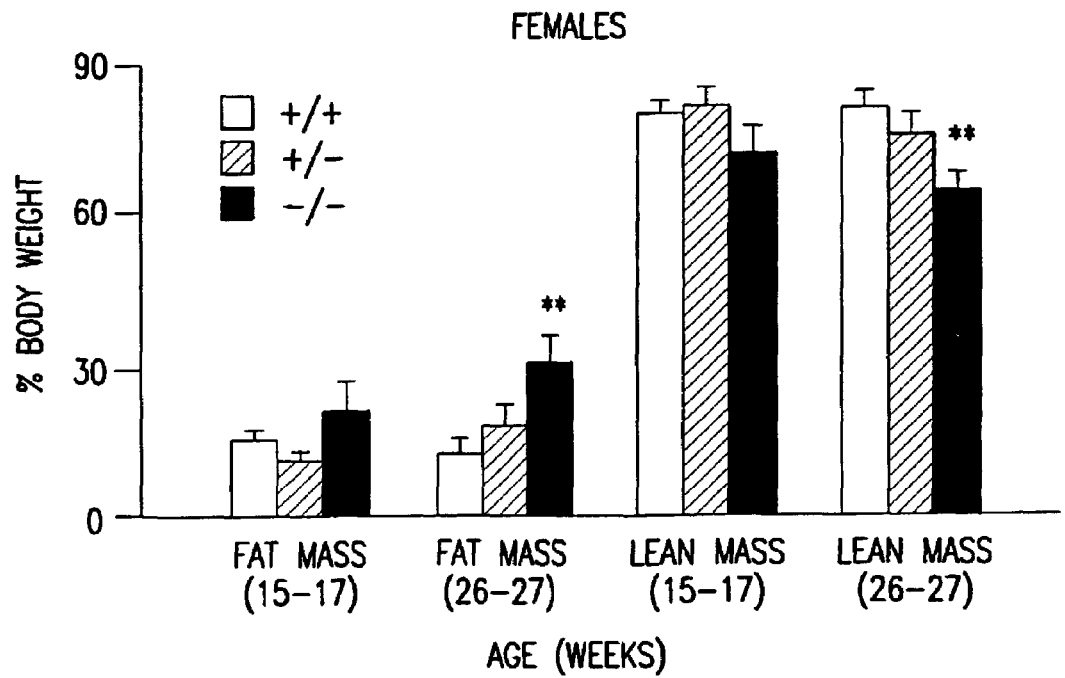
Figure 11A:
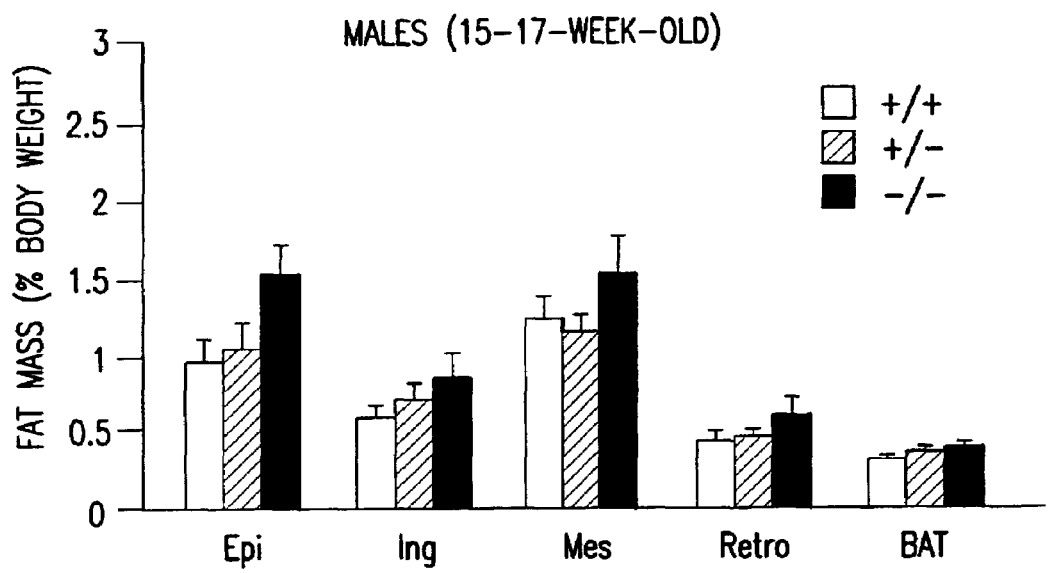
FIG. 11A-H shows adipose tissue mass in wild-type (+/+), heterozygous mutant (+/-), and homozygous mutant (-/-) littermate mice (A-D). All mice are the same mice evaluated in FIG. 10 C-D. Fat pads: epididymal (Epi), ovarian (Ova), inguinal (Ing), mesenteric (Mes), retroperitoneal (Retro), and interscapular brown adipose tissue (BAT). All values are mean ±s.e.m. Statistics were performed with a two-tailed unpaired Student's t-test. All P-values are from comparison between MC-3R$^{-/-}$ and wild-type mice. * P<0.05, ** P<0.01. Morphology of BAT (FIG. 11E-F) and WAT [white adipose tissue] (FIGS. 11G,H) in 4-month-old wild-type (FIGS. 11E,G) and MC-3R$^{-/-}$ (FIGS. 11F,H) mice. Tissues were fixed in 10% buffered formaldehyde and embedded in paraffin. Eight μm sections were cut and stained with standard H & E procedures. Magnification at 40×.
Figure 11B:
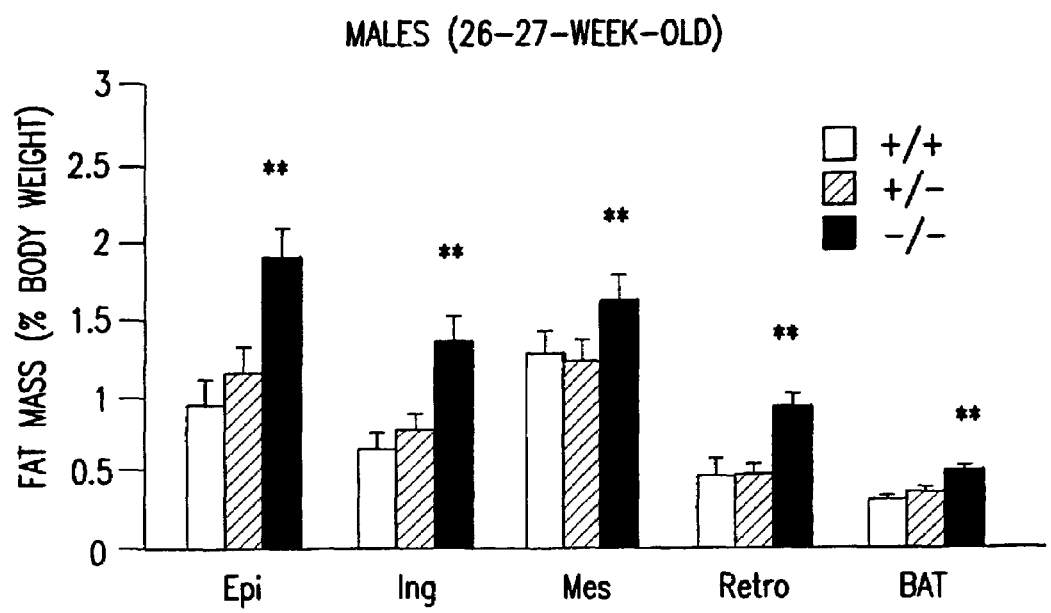
Figure 11C:
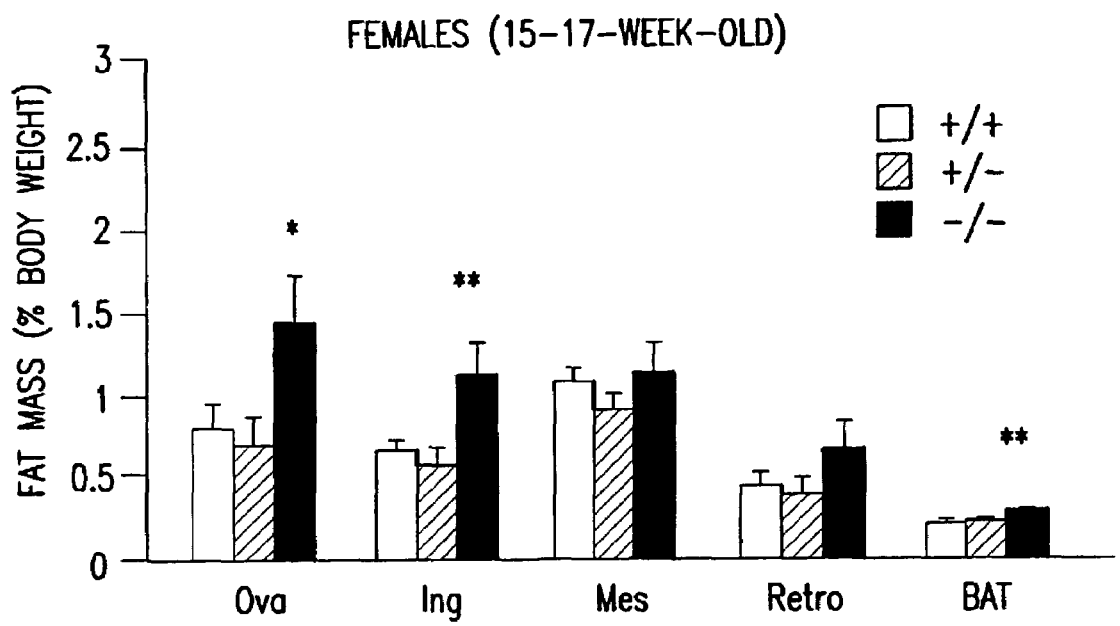
Figure 11D:
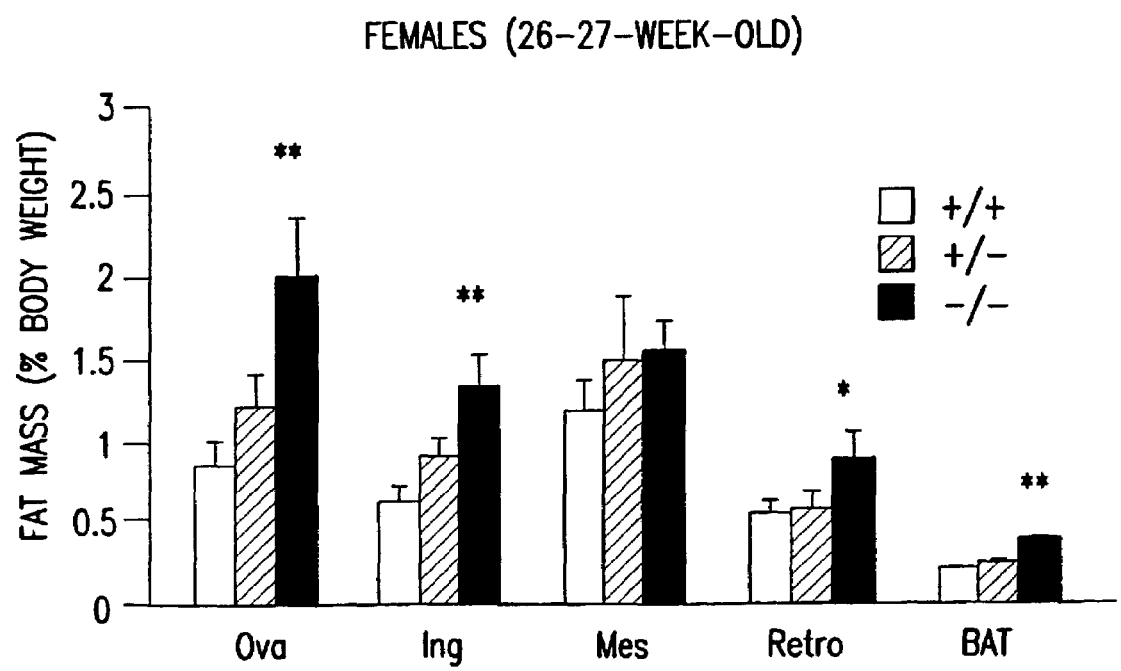
Figure 11E:
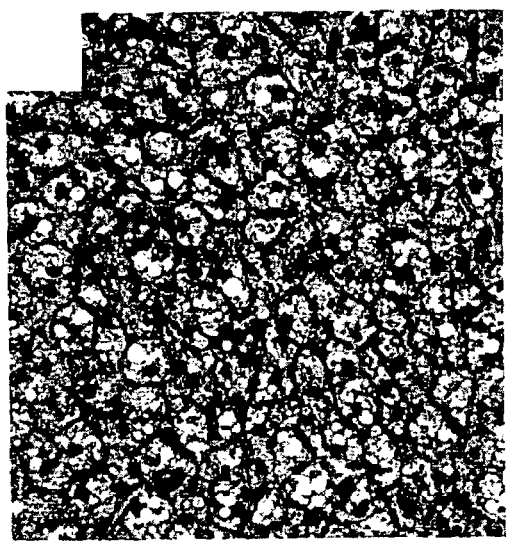
Figure 11F:
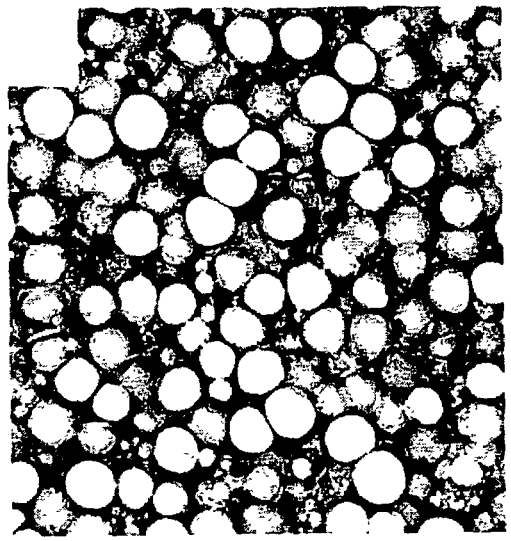
Figure 11G:
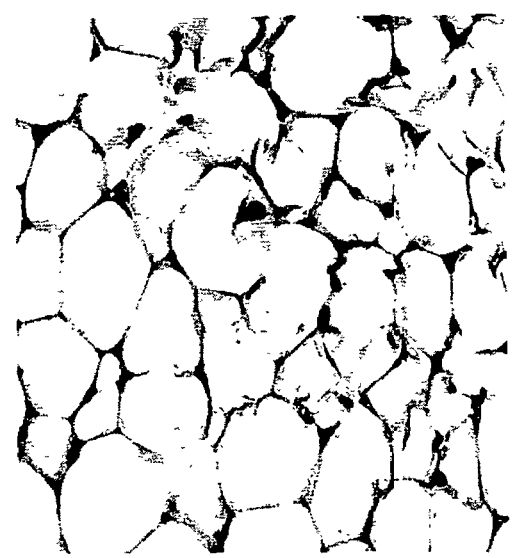
Figure 11H:
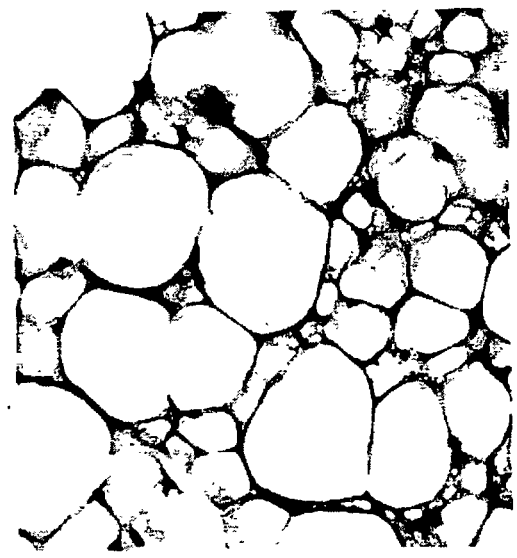

Heterozygous and homozygous mutant mice of both sexes were born at the expected frequency and were viable and fertile through adulthood (approximately 300 MC-3R$^{-/-}$ mice produced). Gross and histological examination of brains and other organs of mutant mice did not reveal any overt abnormalities. The growth of mutant male mice was normal until approximately 25 weeks of age, at which time heterozygous and homozygous mutant male mice became slightly, but significantly heavier than WT littermates (FIG. 10A). Five week-old female MC-3R$^{-/-}$ mice were slightly, but significantly lighter than WT littermates; however, by 7 weeks of age their body weights normalized and by 26 weeks of age they began to display a trend towards increased body weights relative to WT littermates (FIG. 10B). The growth curve of heterozygous mutant female mice did not deviate from those of WT female mice.

Dual energy x-ray absorptiometry analysis (DEXAscan) of male and female mice of all three genotypes at 4 and 6 months of age determined whole body composition. At 6 months of age, MC-3R$^{-/-}$ mice exhibited significantly elevated fat mass and significantly reduced lean body mass (FIGS. 10 C,D). By this age, fat mass of MC-3R$^{-/-}$ mice was approximately double that of WT littermate mice and lean body mass was reduced by approximately 15-20%. Normal body composition was observed in heterozygous mutant mice of both sexes. The body composition of F2 progeny generated from two additional ES cell clones was measured. By 6 to 8 months of age, homozygous mutant mice derived from these two ES cell clones also exhibited significantly increased fat mass and significantly reduced lean body mass relative to WT littermates, indicating the observed phenotype was not due to clonal variation. These differences in body composition have opposing effects on body weight and underlie the subtle differences observed in the growth curves of the mutant mice. These data demonstrate the involvement of MC-3R in the regulation of body composition and suggest that in the absence of MC-3R, nutrients are preferentially partitioned into fat mass at the expense of lean body mass.

To further characterize the observed increase in fat mass, several distinct fat pads were isolated and weighed. Consistent with the DEXAscan analysis, several fat depots isolated from 4- and 6-month-old female MC-3R$^{-/-}$ mice were significantly heavier than those of WT mice (FIG. 11A-D). Differences in fat depot weights of males did not reach statistical significance until 6 months of age. By 6 months of age, all fat depots examined, with the exception of the female mesenteric fat pads, were significantly heavier than those of WT mice. Histological evaluation of inguinal white adipose tissue (WAT) and interscapular brown adipose tissue (BAT) revealed an increase in the size of adipocytes from MC-3R$^{-/-}$ mice (FIGS. 11E-H). Additionally, BAT from MC-3R$^{-/-}$ mice showed a reduction in the number of typical mitochondrial-rich multilocular brown adipocytes and a dramatic increase in the presence of unilocular cells. Consistent with the enlarged appearance of white adipocytes, area measurements of white adipocytes from WT and MC-3R$^{-/-}$ mice demonstrated an approximately 20-30% increase in the size of adipocytes from mutant mice. The DNA content of this WAT depot from MC-3R$^{-/-}$ mice was similar to that of WT mice (MC-3R$^{-/-}$, 207.04±5.82 µg vs. WT, 205.09±5.63 µg; n=8) and the RNA to DNA ratio was normal. In contrast, the DNA content of BAT from MC-3R$^{-/-}$ mice was significantly increased (P<0.01; MC-3R$^{-/-}$, 151.18±7.31 µg vs. WT, 121.88±5.85 µg; n=8), yet the RNA to DNA ratio was unchanged. These data demonstrate that the increase in WAT fat mass observed in MC-3R$^{-/-}$ mice is predominantly due to fat cell hypertrophy and suggest that the absence of MC-3R$^{-/-}$ results in alterations in fat cell metabolism. The approximate 24% increase in BAT DNA content suggests the presence of brown adipocyte hyperplasia or white adipocyte infiltration into the BAT depot. This phenotype is consistent with the hypertrophic appearance of fat in mutant mice that ectopically express the natural antagonists of MC-3R and MC-4R, agouti or Agouti related protein (Agrp).

To further investigate the reductions in lean body mass observed in MC-3R$^{-/-}$ mice, liver IGF-I mRNA levels were evaluated as a measure of growth axis activity. Although slight differences in the levels of liver IGF-I expression were detected between MC-3R$^{-/-}$ and WT mice, these differences were very small and did not correlate with the reduction in lean mass. It appears that at a gross level the hypothalamic-pituitary axis is normal with regards to downstream control of IGF-I gene expression.

Lean body mass is primarily composed of skeletal muscle, blood, and bone. DEXAscan analysis demonstrated that MC-3R$^{-/-}$ mice possess normal bone mineral content, yet the average length of femur bones isolated from both 15-17- and 26-27-week-old female MC-3R$^{-/-}$ mice was significantly shorter than that of age matched WT littermate mice. The nose to anus length of the younger group of MC-3R$^{-/-}$ female mice was also significantly shorter than that of WT littermate mice, suggesting that in the absence of MC-3R growth is stunted. Although male MC-3R$^{-/-}$ mice displayed similar trends in bone and body lengths, these differences did not reach statistical significance.

Figure 12A:
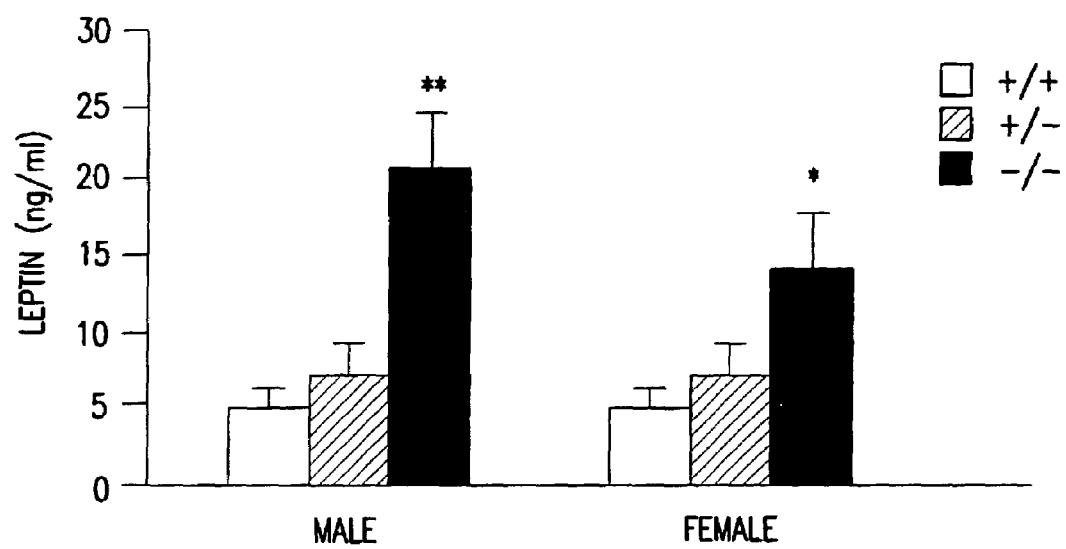
FIGS. 12A-D show four plasma leptin (A), insulin (B), glucose (C), and corticosterone (D) levels of wild-type (+/+), heterozygous mutant [MC-3R$^{-/+}$](+/-), and homozygous mutant [MC-3R$^{-/-}$](-/-) littermate mice. Plasma leptin, insulin, and glucose levels were measured from the same 6-month-old mice (males, n=8-12; females, n=8-13) evaluated in FIGS. 3B,D. Plasma corticosterone levels were measured from 3.5-4-month-old mice (males, n=8-10; females, n=8). All values are mean ±s.e.m. Statistics were performed with a two-tailed unpaired Student's t-test. All P-values are from comparison between MC-3R$^{-/-}$ and wild-type mice unless indicated otherwise. * P<0.05, ** P<0.01.
Figure 12B:
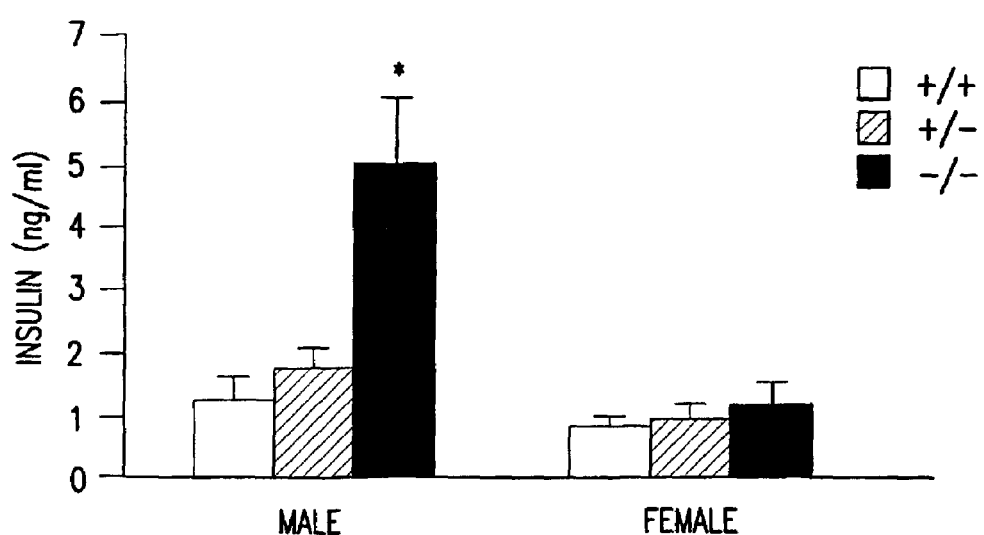
Figure 12C:
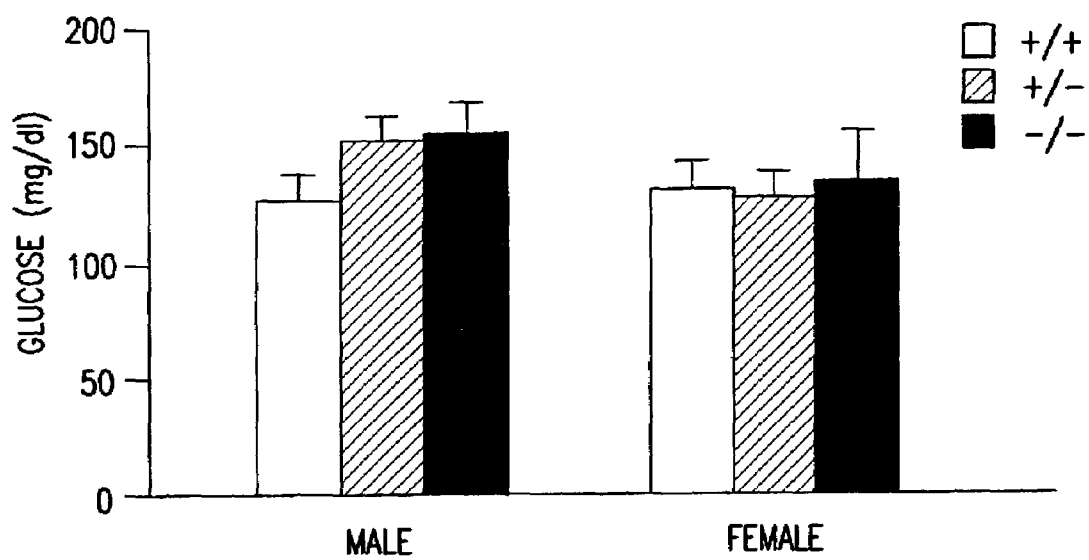
Figure 12D:
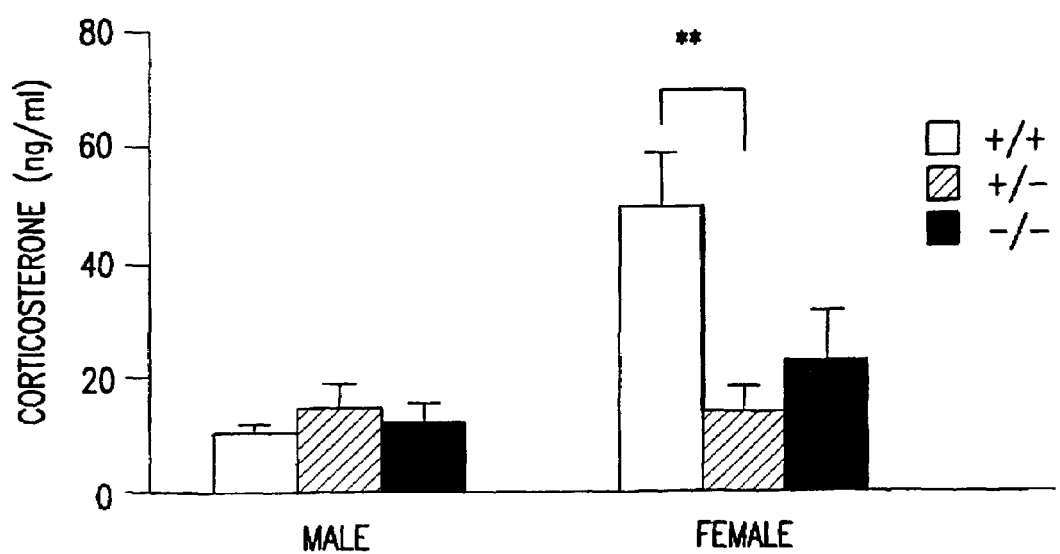

To determine if MC-3R-deficiency results in endocrine abnormalities, plasma levels of several hormones were evaluated. Six-month-old MC-3R$^{-/-}$ mice were significantly hyperleptinemic (FIG. 12A) and developed mild hyperinsulinemia which reached statistical significance in male mutant mice only (FIG. 12B). These endocrine abnormalities are likely secondary to the increased fat mass. Despite the increased insulin levels observed in mutant male mice, plasma glucose levels were maintained within a normal range (FIG. 12C). At 6 months of age plasma triglyceride and cholesterol levels were also within the normal range in male and female MC-3R$^{-/-}$ mice. Plasma corticosterone levels in MC-3R$^{-/-}$ mice were also not significantly different from those of WT mice at 3.5-4 months of age; however, female MC-3R$^{-/-}$ mice exhibited a trend towards reduced corticosterone levels (FIG. 12D).

Figure 13B:
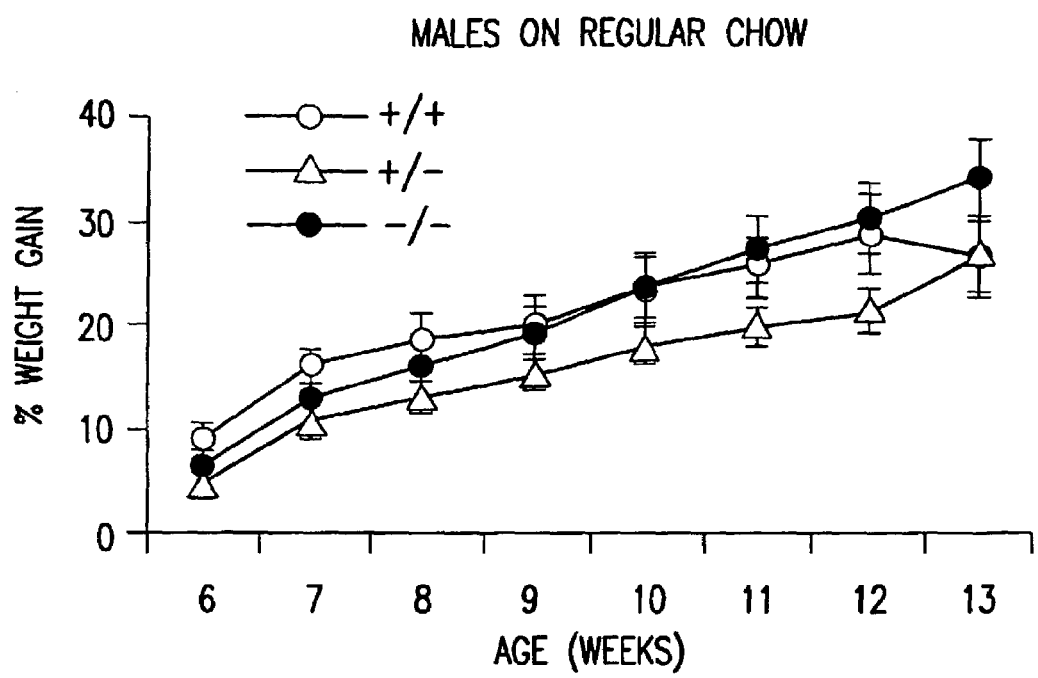
Figure 13C:
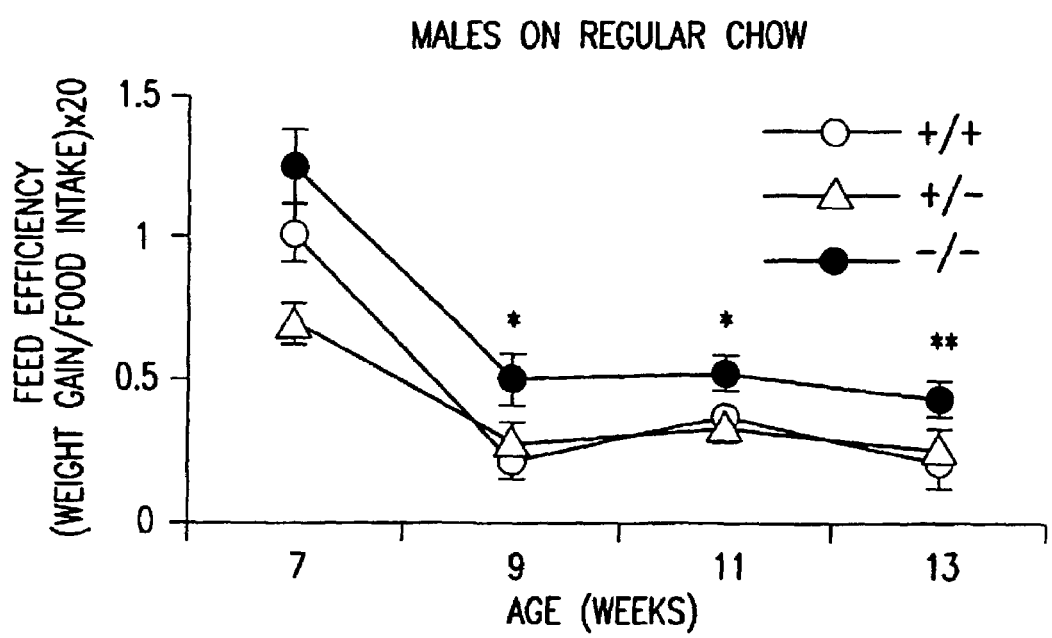
Figure 13D:
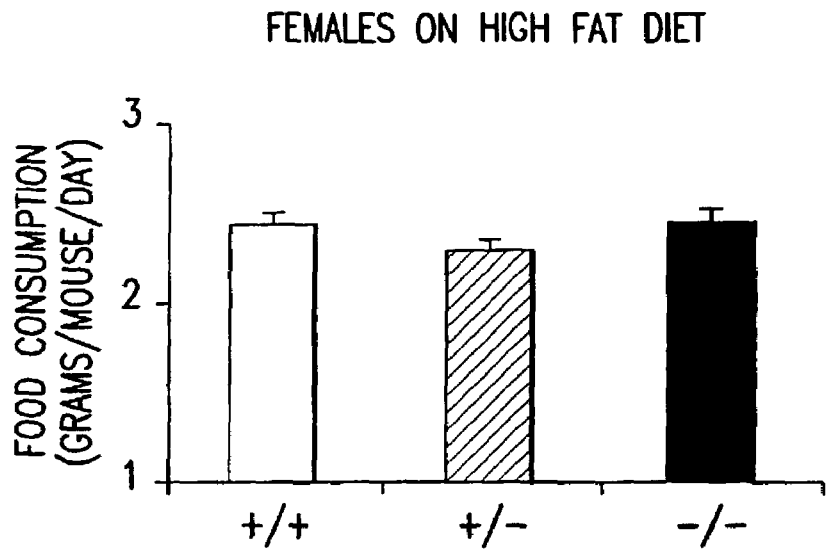
Figure 13E:
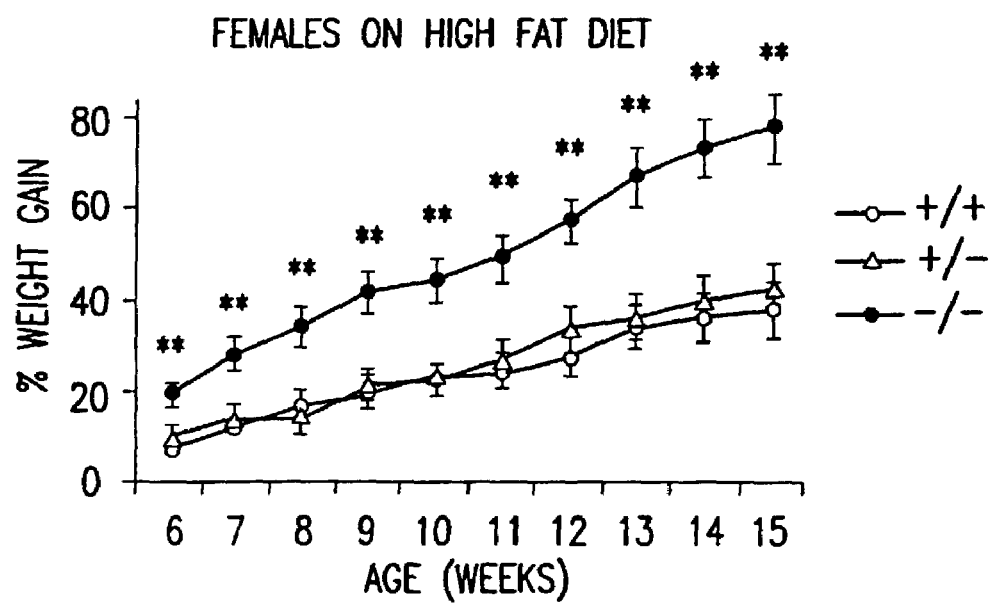
Figure 13F:
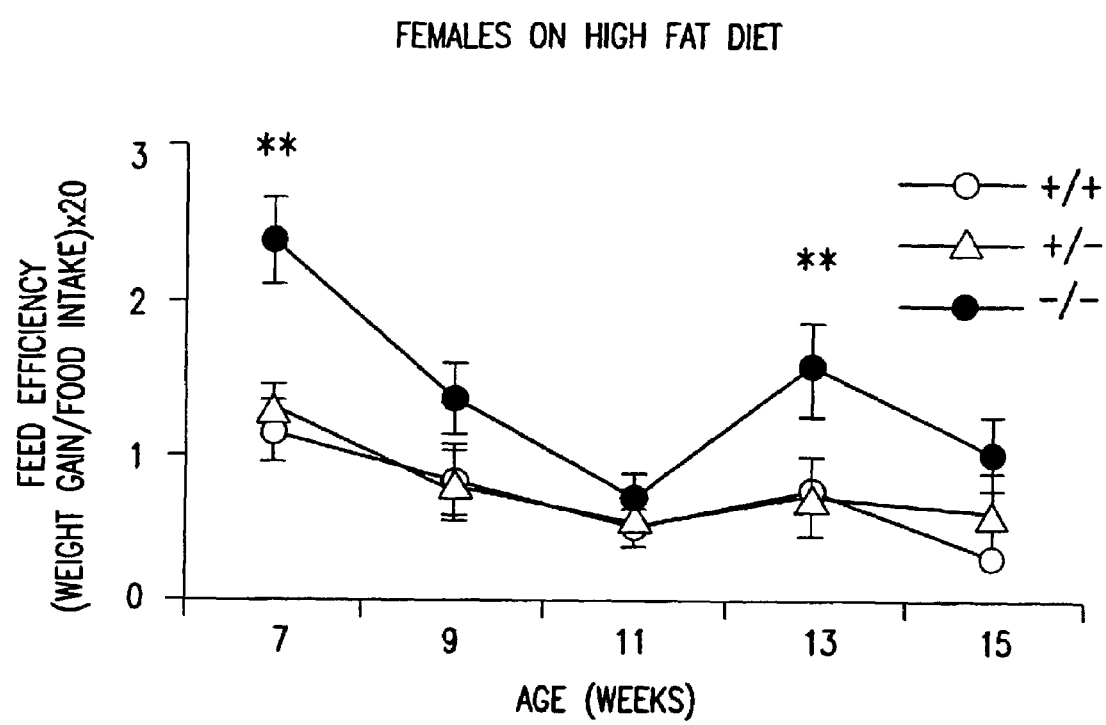

Alterations in food intake can lead to differences in body composition and it has been shown that MC-4R$^{-/-}$ mice and mice ectopically expressing agouti or Agrp are significantly hyperphagic. In contrast, male MC-3R$^{-/-}$ mice maintained on a regular chow diet are significantly hypophagic (FIG. 13A) and display normal weight gain (FIG. 13B). Consequently, they exhibit significantly greater feed efficiency, gaining more body weight per gram of food consumed than WT mice (FIG. 13C). Heterozygous mutant male mice also displayed significantly reduced average daily food intake relative to wild-type littermate mice. Female MC-3R$^{-/-}$ mice maintained on regular chow did not exhibit significant hypophagia, but did display significantly greater feed efficiency than WT mice at 10 weeks of age (data not shown). When female mice were exposed to a high fat diet, MC-3R$^{-/-}$ mice consumed normal amounts of food (FIG. 13D), yet gained significantly more body weight than either WT or heterozygous mutant mice (FIGS. 13C,E), resulting in significantly greater feed efficiency (FIGS. 13C,F). These data demonstrate that MC-3R-deficiency results in increased feed efficiency and that hyperphagia is not the primary cause of the increased fat mass observed in MC-3R$^{-/-}$ mice. Furthermore, these data suggest that reduced food intake may contribute to the observed decrease in lean body mass.

Both central and systemic administration of a non-selective melanocortin agonist, MTII inhibit food intake. To determine if MC-3R is required for the anorectic actions of MTII, the response of male MC-3R$^{-/-}$ and WT mice to peripherally administered MTII was evaluated. A single intraperitoneal injection of MTII at a dose of 10 mg/kg reduced food consumption over a 24-h period significantly (P<0.05) and to a similar extent in both WT and MC-3R$^{-/-}$ mice (WT, 11.1±4.3% reduction vs. MC-3R$^{-/-}$, 16.9±7.0% reduction; P=0.49; n=9) relative to a 2-day vehicle treatment baseline. These data demonstrate that MC-3R is not required for the anorectic actions of MTII and imply that α-MSH primarily inhibits food intake through modulation of MC-4R. Similar conclusions have been drawn from pharmacological studies with MTII involving MC-4R$^{-/-}$ mice.

Figure 14A:
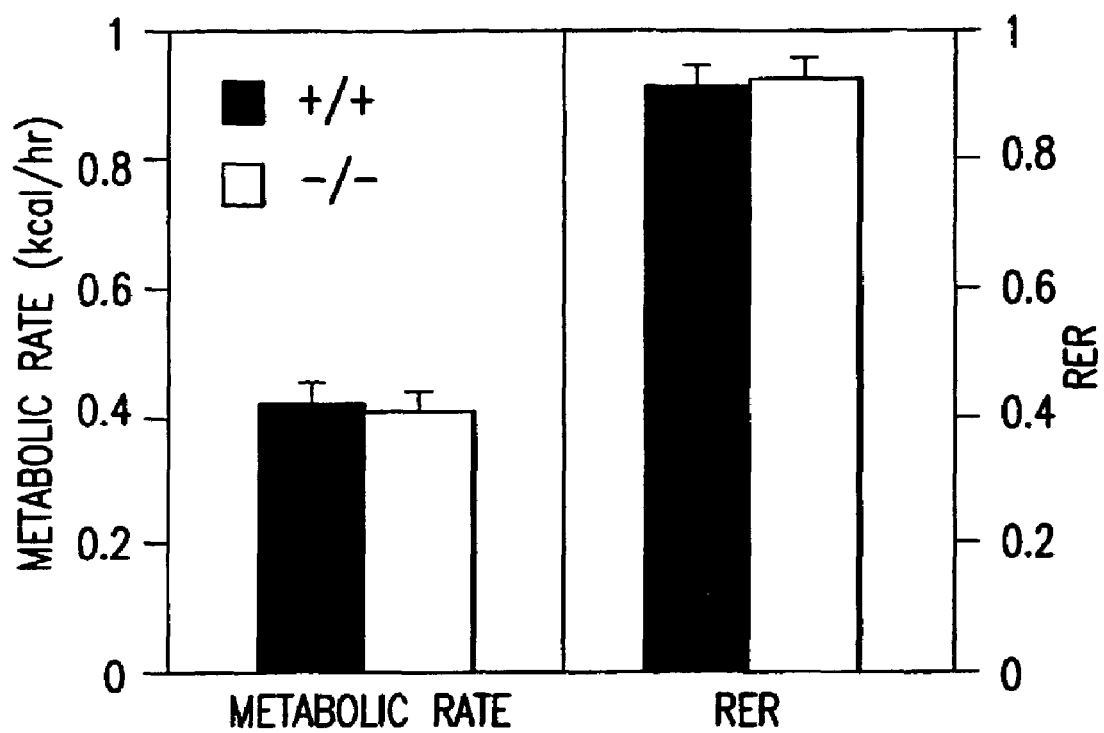
FIGS. 14A-E shows metabolic rate (A), locomotor activity (B,D), and fine movements (C,E) of individually-housed MC-3R$^{-/-}$ and wild-type mice. Metabolic rate and respiratory exchange ratio (RER) were measured in female MC-3R$^{-/-}$ (-/-, n=10) and wild-type (+/+, n=10) littermate mice for 24 h by indirect calorimetry and reported as an hourly average. Locomotor activity of male and female MC-3R$^{-/-}$ (-/-, n=11 per sex) and wild-type (+/+, n=11 per sex) littermate mice was measured during a 12 h light and 12 h dark cycle and reported as distance traveled in meters. Fine movements of mice were also measured at the same time and reported as the number of photobeam breaks. All values are mean ±s.e.m. Statistics were performed with a two-tailed unpaired Student's t-test. All P-values are from comparison between MC-3R-/- and wild-type mice. * P<0.05.
Figure 14B:
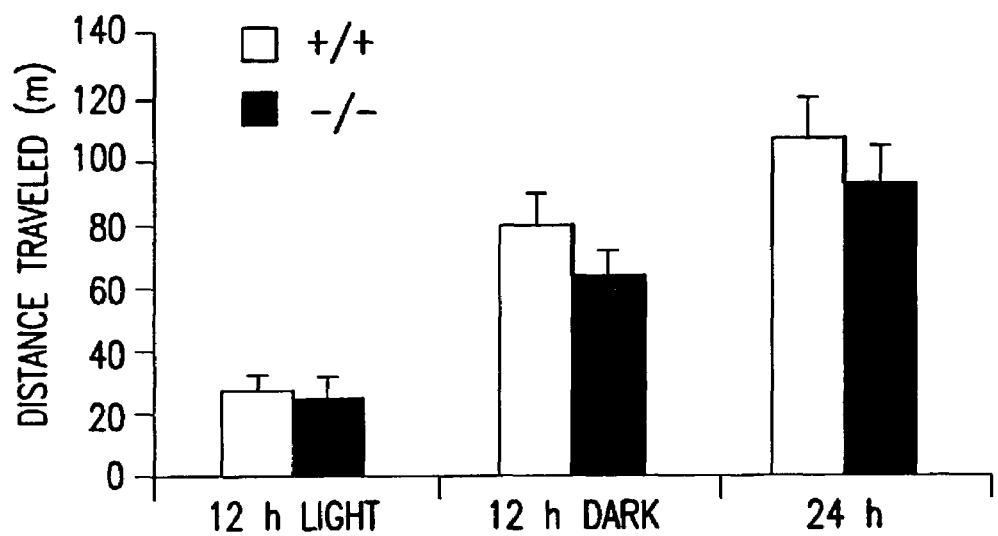
Figure 14C:
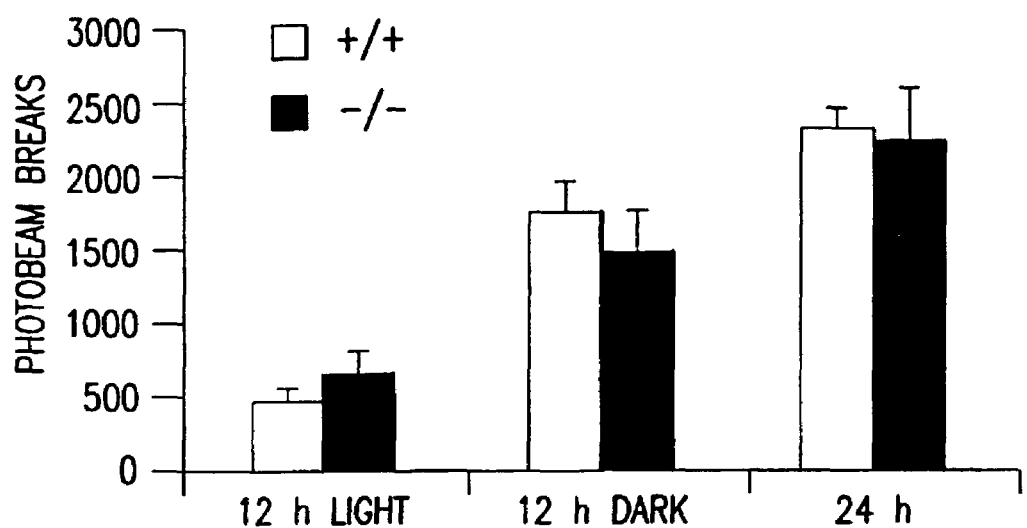
Figure 14D:
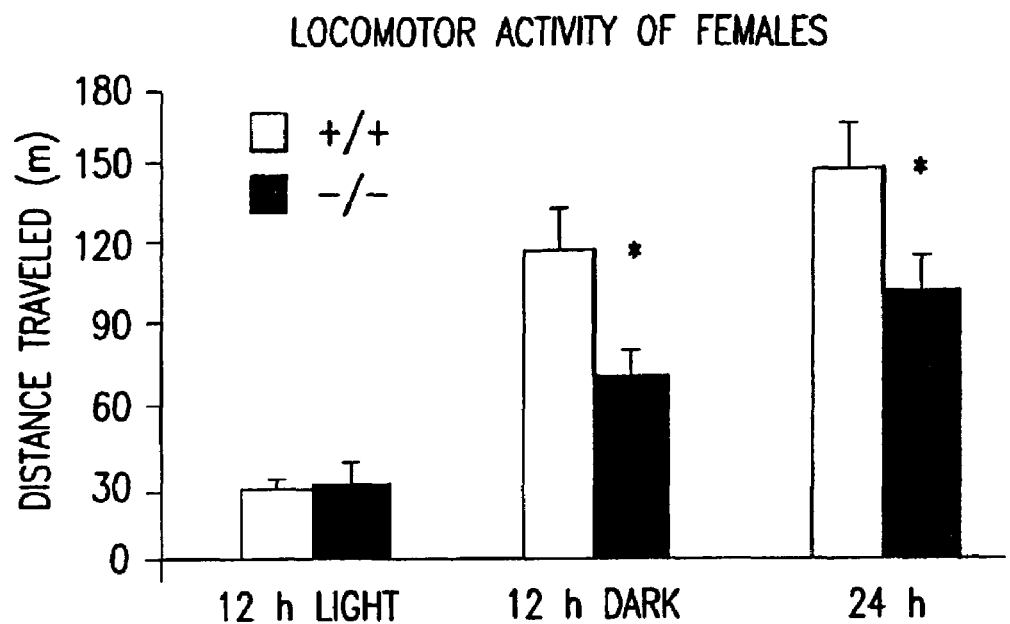
Figure 14E:
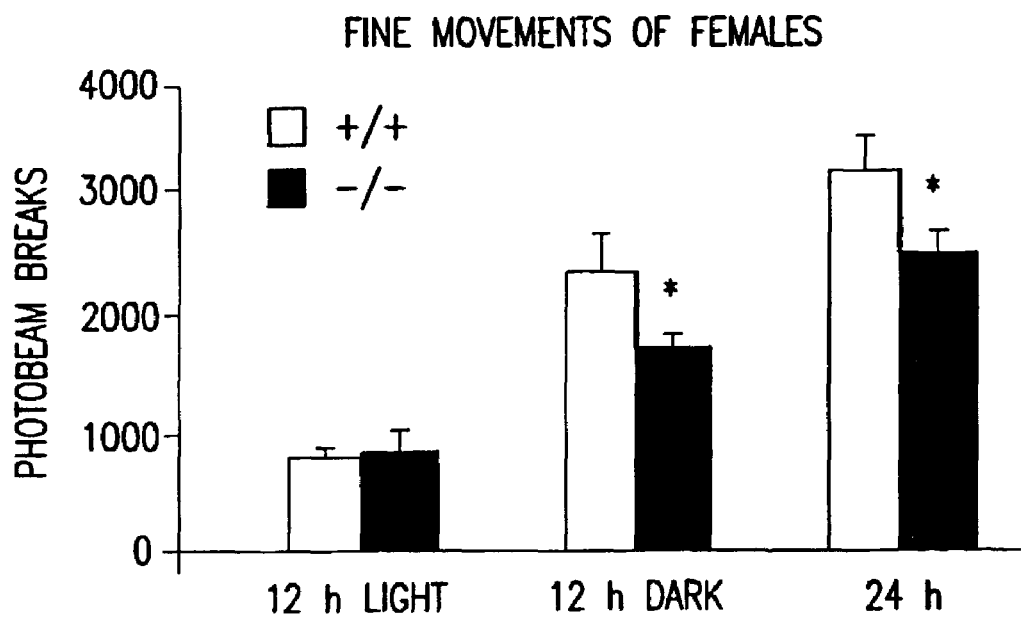

Deficits in metabolic rate and ambulatory activity can also result in alterations in body composition. Body temperatures of both male and female MC-3R$^{-/-}$ mice were normal (male: WT, 36.88±0.07° C. vs. MC-3Rw, 36.77±0.12° C.; female: WT, 37.37±0.19° C. vs. MC-3R$^{-/-}$, 37.37±0.15° C.; n=10-11), suggesting that the absence of MC-3R does not result in large changes in metabolic rate. Indirect calorimetry was employed to further evaluate metabolic rate. Female MC-3R$^{-/-}$ mice exhibited normal metabolic rates and respiratory exchange ratios relative to WT littermate mice when evaluated for 24 h with ad libitum access to food and water (FIG. 14A). The ambulatory activity of 5-6-month-old male and female mice was evaluated. Male MC-3R$^{-/-}$ mice exhibited a trend towards reduced levels of locomotor activity and fine movements during the dark cycle (FIGS. 14A,B,C) and with female MC-3R$^{-/-}$ mice these reductions reached statistical significance (FIGS. 14D,E). These data suggest that reductions in ambulatory activity may contribute to the increased fat mass observed in female MC-3R$^{-/-}$ mice; however, it is not clear whether these deficits in ambulatory activity are directly related to the absence of MC-3R or secondary to changes in body composition.

In situ hybridization was employed to determine if the absence of MC-3R results in altered patterns of neuropeptide expression in the brain (see Bagnol et al., 1999, *J. Neurosci.* 19:RC261-7). MC-3R is co-expressed with POMC in hypothalamic neurons located in the arcuate nucleus, suggesting that it might be an autoreceptor for α-MSH. However, a significant change in arcuate POMC mRNA could not be detected in either 1- or 3-month-old male MC-3R$^{-/-}$ mice. Neuropeptide Y (NPY) is a potent orexigenic peptide abundantly expressed in the hypothalamus. A small, but significant (P<0.05; WT, 1315±101 nCi/g tissue vs. MC-3R$^{-/-}$4, 1099±101 nCi/g tissue; n=5) 16% reduction in NPY mRNA in the arcuate nucleus was detected in 1-month-old male MC-3R$^{-/-}$ mice, but by 3 months of age NPY mRNA levels had returned to normal. A reduction in NPY expression in the arcuate nucleus could potentially contribute to the hypophagia observed in male MC-3R$^{-/-}$ mice.

These data show that MC-3R serves a unique role, which is not redundant when compared to MC-4R, in the regulation of energy homeostasis. Since MC-3R is widely expressed in distinct tissues, including brain, adipose tissue, heart, skeletal muscle, kidney, stomach, duodenum, placenta, and pancreas, direct effects of the loss of MC-3R expression in these tissues may contribute to the phenotypes observed. Recently, a locus encoding MC-3R on human chromosome 20q has been linked to the regulation of body mass index, subcutaneous fat, fat mass, and fasting insulin levels. Therefore, these findings show that MC-3R modulation may prove beneficial for the treatment of obesity.

EXAMPLE 3

MC-3R/MC-4R Knockout Mice

In order to generate MC-4R and MC-3R double knockout mice, MC-3R heterozygous males were crossed with MC-4R KO females to generate MC-3R$^{-/+}$, MC4R$^{-/+}$ mice. Eleven out of 28 male pups were identified as such and 7 were bred with MC-4R KO females to generate MC-3R$^{-/+}$, MC-4R$^{-/-}$ mice. Several litters produced 7 male and 6 Female of MC-3R$^{-/+}$, MC-4R$^{-/-}$ mice. These mice are crossed to produce MC-3R$^{-/-}$, MC-4R$^{-/-}$ double knockout mice.

Figure 15:
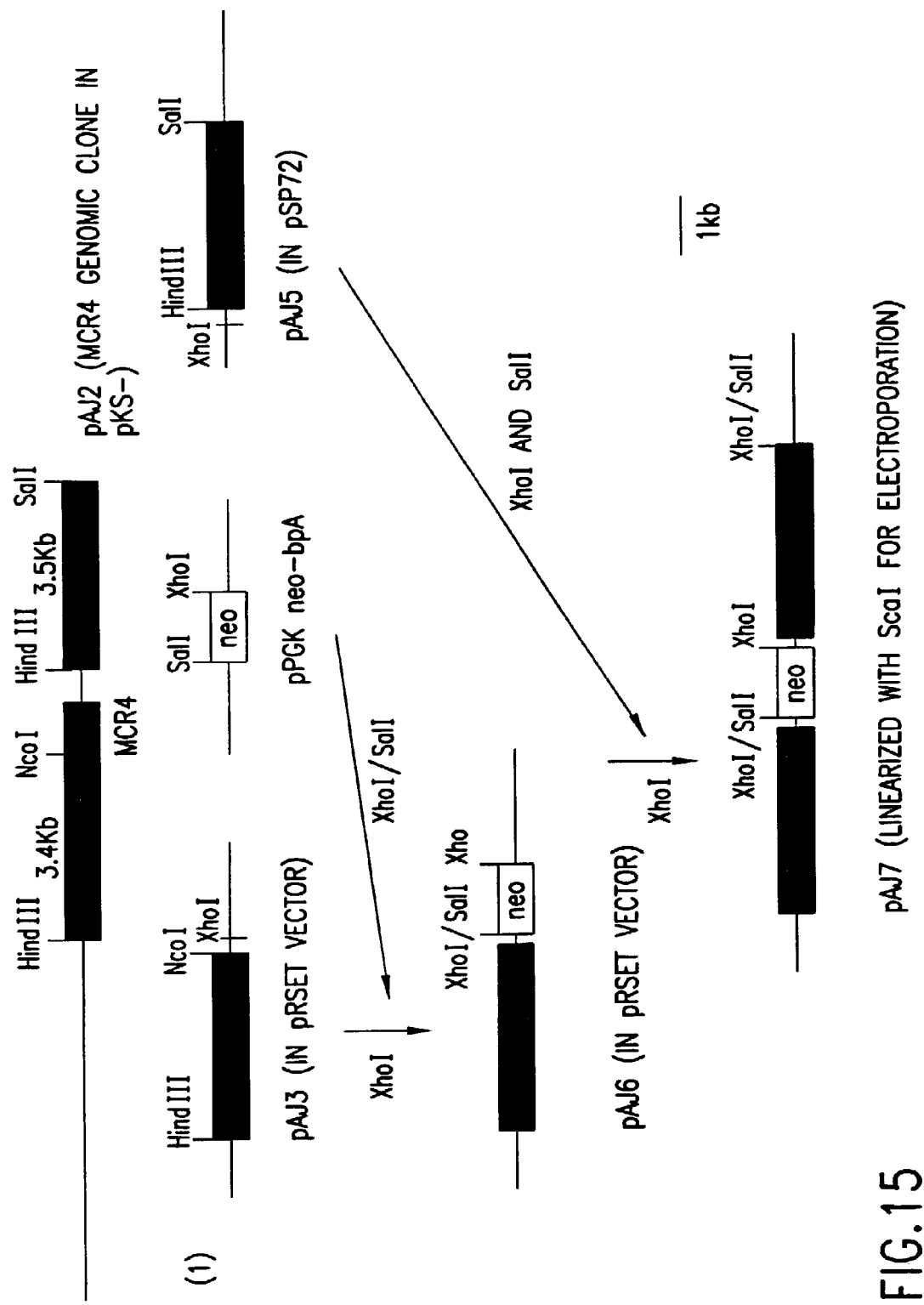
FIG. 15 shows a schematic description of the strategy utilized in construction of the targeting gene vector, pAJ7.
Figure 16:
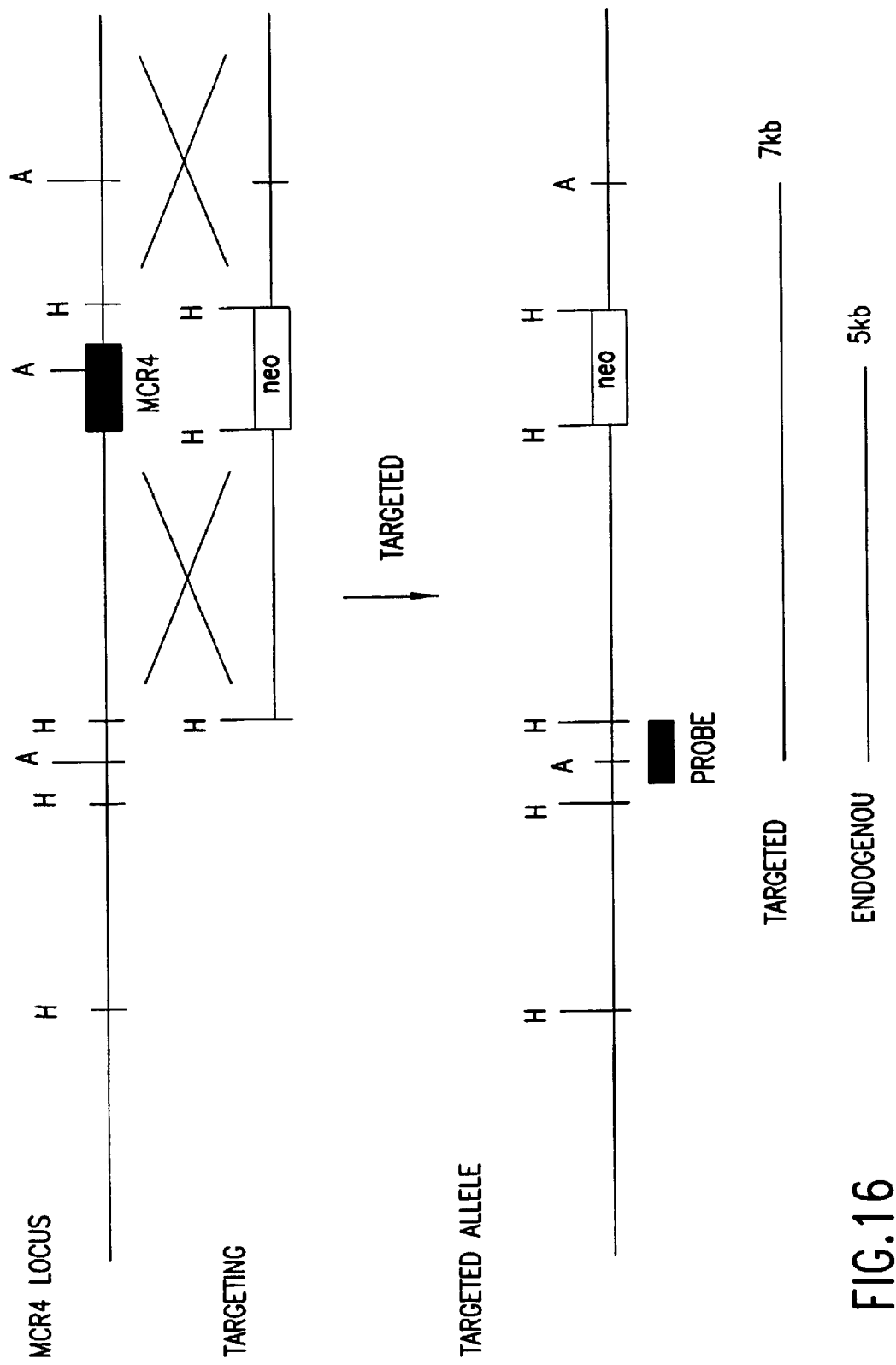
FIG. 16 shows the strategy utilizing the targeting gene vector, pAJ7, for homologous recombination with mouse genomic sequences encoding MC-4R.

The MC-4R transgenic mice used initiate generation of MC-3R$^{-/-}$, MC-4R$^{-/-}$ double knockout mice are described in detail in U.S. Provisional Application Serial No. 165,074, filed Nov. 12, 1999 and PCT International Application No. PCT/US00/31061, hereby incorporated by reference. The generation of MC-4R$^{-/-}$ knockout mice are also described in Huszar et al., 1997, *Cell* 88: 131-141 and U.S. Pat. No. 5,932,779, issued Aug. 3, 1999 to Lee et al). Briefly, genomic DNA containing the murine MC-4R gene was isolated from a mouse 129$_{sjv}$ lambda genomic library (Lambda FIX II Library, Stratagene, La Jolla, Calif.) and screened using a 1-Kilobasepair (Kb) rat MC-4R cDNA clone as a probe. One of four clones was mapped in detail by restriction enzyme digestion. The clone consisted of the 29-kilobase pair (Kb) lambda vector and a 15 Kb genomic insert encoding the 1 Kb MC-4R coding sequence, between 10 Kb of 5' and 4 Kb of 3' flanking sequences. An approximately 1.5 Kb fragment extending from an NcoI site located approximately 20 basepair (bp) downstream of the MC4R translation initiation codon to the HindIII site situated approximately 0.5 Kb downstream of the ATG stop codon of the MC-4R coding sequence was replaced with a PGK-neo cassette (neomycin phosphotransferase gene under the control of the phosphoglycerokinase promoter [pPGKneobpA, obtained from Dr. Alan Bradely; also see e.g., Tybulewicz et al., 1991, *Cell* 65:1153-1163). The targeting vector was constructed in pSP72 (Promega) consisting of a 5' 3.4 Kb HindIII to NcoI fragment, the 1.6 Kb PGK-neo fragment and a 3' 3.5 kb HindIII to SalI fragment. A complete schematic diagram for constructing pAJ7 is shown in FIG. 15 while the strategy for recombination with mouse genomic sequences is shown in FIG. 16. The gene targeting vector pAJ7 was linearized at a unique ScaI site and electroporated into the AB2.2 embryonic stem cells (Lexicon Genetics) under standard condition using a Gene Pulser (Bio-Rad). Selection of the G418-resistant clones was performed as previously described (Von Koch et al., 1997). To facilitate the identification of a large number of knockout and wild type mice, 3 oligonucleotides were designed to distinguish the knockout allele from the wild-type allele by PCR. The synthetic oligonucleotides 5'-CTAACCATAAGAAATCAGCAGC-CCG-3'(SEQ ID NO:12) and 5'-AGGGAAGTATACATGC-CATGGTGGT-3' (SEQ ID NO: 13) result in 500 bp PCR product by wild type allele. Of course, these oligos may also be utilized to obtain a wild type PCR probe for identifying the 29 Kb/15 Kb mouse genomic sequence which contains the wild type murine MC-4R gene as used herein. Also, oligonucleotides 5'-CTAACCATAAGAAATCAGCAGC-CCG-3' (SEQ ID NO:14) and 5'-TACCGGTGGATGTG-GAATGTGTGC-3' (SEQ ID NO:15) result in 650 bp product derived from the mutant allele.

Targeted ES clones were identified by Southern blotting analysis, using a 700-bp NcoI-HindIII fragment located 5' outside of the targeting vector as a probe. Of the 600 clones selected, 3 showed a 7 Kb targeted ApaI restriction enzyme fragment in addition to the expected 5 Kb wild-type fragment (the ApaI site in the MC-4R coding region was eliminated during the homologous recombination event). These positive clones were microinjected into C57Bl/6J blastocysts to generate chimeric mice. Two male chimeras showed germline transmission of the targeted allele to their offspring. F1 heterozygotes were interbred to produce homozygous knockout, heterozygous, and wild type F2 progeny. These F2 littermate mice were used to measure the body weight starting at 5-week of age. F2 homozygous knockout mice and wild type littermate mice were also used to produce F3 hybrids. For metabolic rate studies, F3 hybrids were used. Since the knock out mice become obese with increasing age, we hypothesized that the homozygous mice might have reduced fertility and therefore would not be suitable for efficient mass-production of knockout mice. However, the litter size of homozygous breeding pairs appeared normal when compared to that of heterozygous breeding pairs. The knockout males of different ages (2 to 4.5 months old) were also evaluated for reproductive performance by mating with young SW females in estrous. Results indicated a normal plug rate (production of vaginal plugs overnight) and litter size for males between 2 and 4.5 months old.

Figure 17:
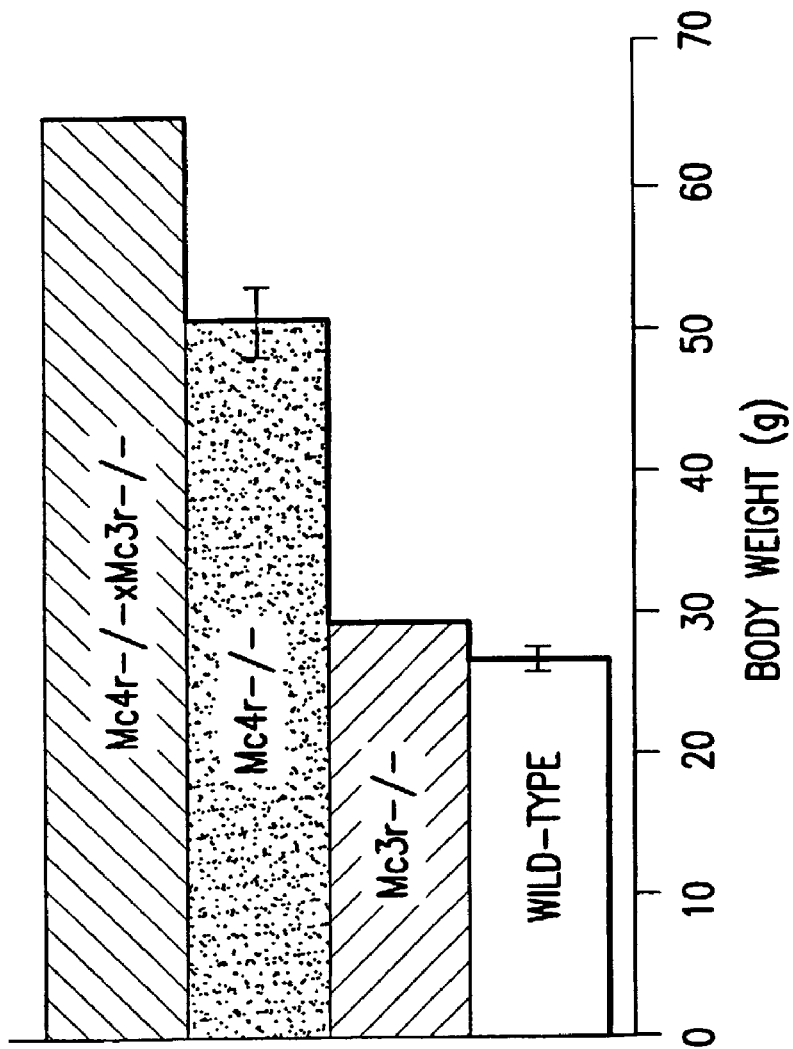
FIG. 17 shows the effects of deleting MC-3R and MC-4R genes on body weight in female mice at age 26 weeks.
Figure 18A:
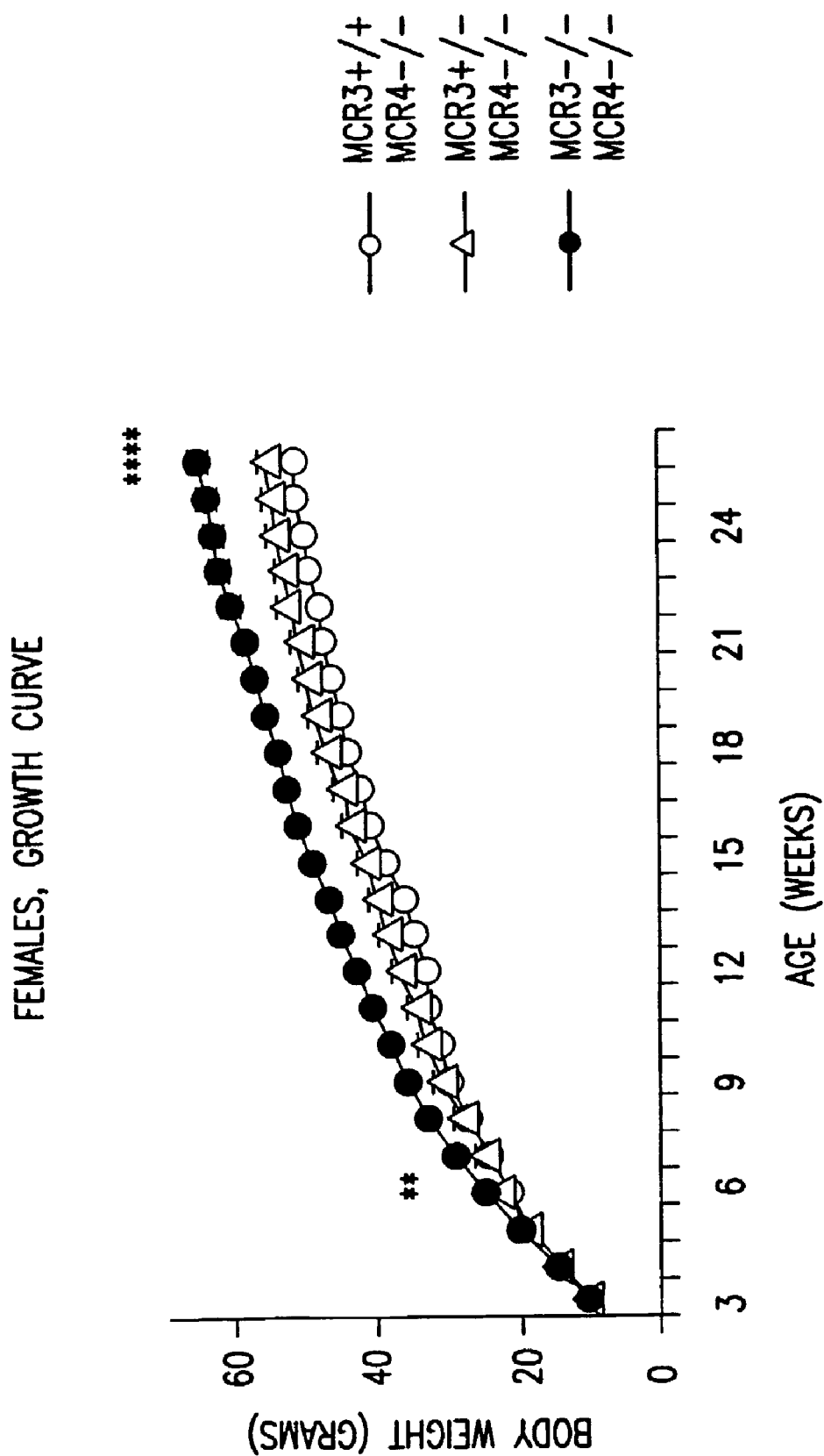
FIGS. 18A-B shows that the female (FIG. 18A) MC-3R$^{-/-}$/MC-4R$^{-/-}$ double knockout mice are significantly heavier (p<0.01) than MC4R$^{-/-}$ mice at six-week-olds. By twenty-six-week-old female MC-3R$^{-/-}$×MC-4R$^{-/-}$ mice are significantly heavier (~27%) than littermates lacking only MC-4R (MC-3R$^{-/-}$×MC-4R$^{-/-}$, 64.58±1.92 g vs. MC-4R$^{-/-}$, 50.77±1.48 g; n=10-18; P<0.0001) and male MC-3R$^{-/-}$×MC-4R$^{-/-}$ mice (FIG. 18B) of comparable age are also significantly heavier (~13%) than MC-4R$^{-/-}$ littermates (MC-3R$^{-/-}$×MC-4R$^{-/-}$/62.57±1.86 g vs. MC-4R$^{-/-}$, 55.60±1.70 g; n=9-13; P<0.05).
Figure 18B:
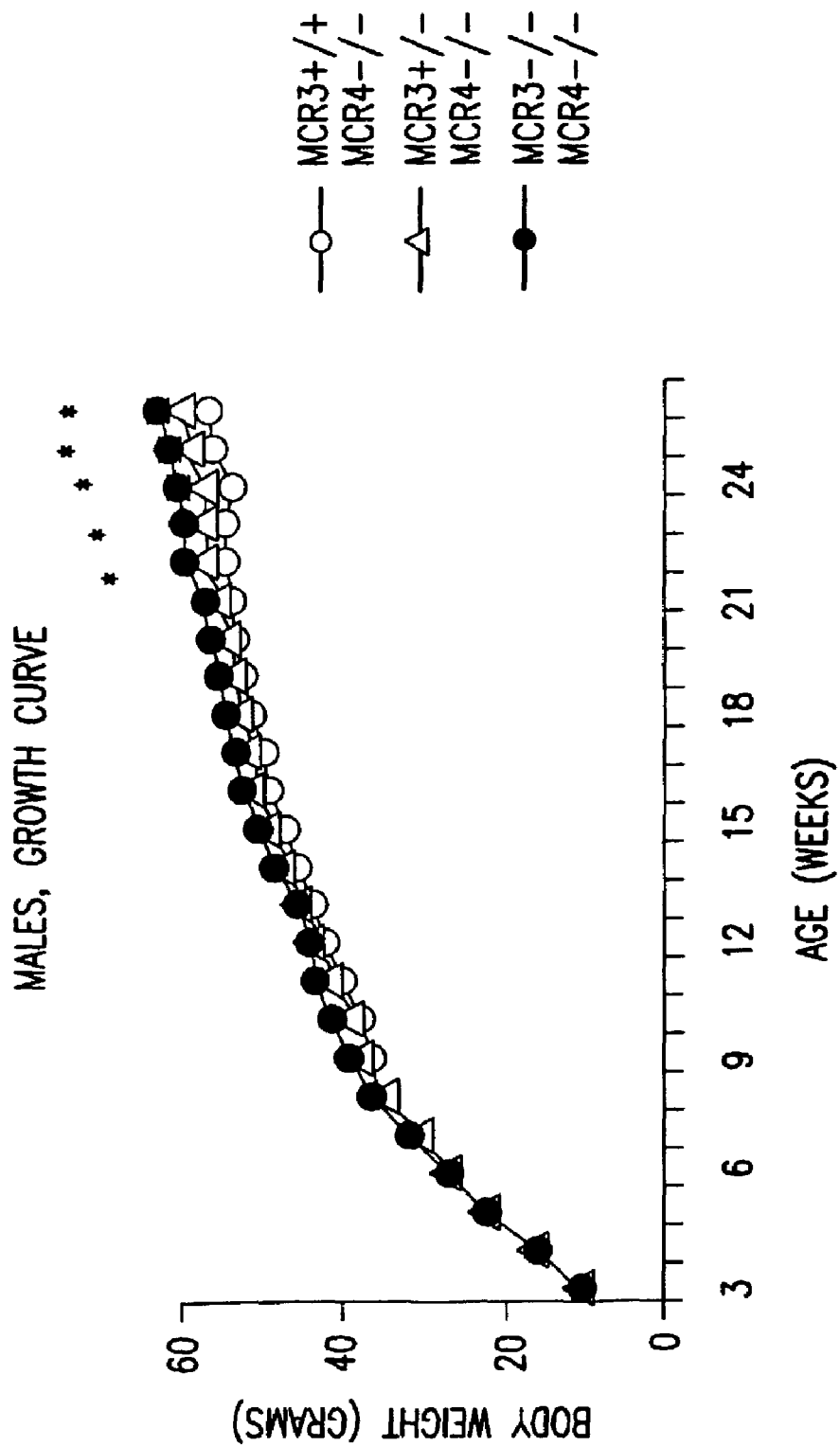
Figure 19A:
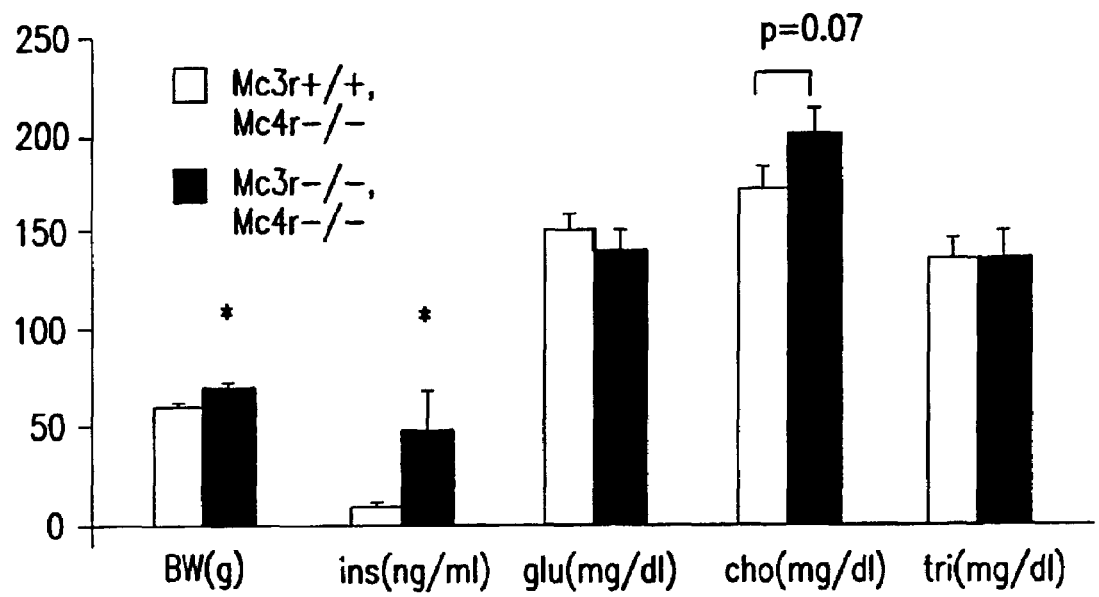
FIGS. 19A-B show that the plasma insulin level of 9-month-old male (FIG. 19A) and female (FIG. 19B) MC-3R$^{-/-}$×MC-4R$^{-/-}$ mice is statistically higher than littermates lacking only MC-4R (male: MC-3R$^{-/-}$×MC-4R$^{-/-}$, 50.72±17.92 ng/ml vs. 8.88±1.83 ng/ml; n=11-13; P<0.05 and female: MC-3R$^{-/-}$×MC-4R$^{-/-}$, 8.59±1.63 ng/ml vs. 1.65±0.53 ng/ml; n=10-14; P<0.01). The glucose level are similar between MC-3R$^{-/-}$×MC-4R$^{-/-}$ and MC-4R$^{-/-}$ mice, as shown in FIGS. 19A and 19B. BW=body weight; ins=insulin; glu=glucose; cho=cholesterol; and tri=triglycerides.
Figure 19B:
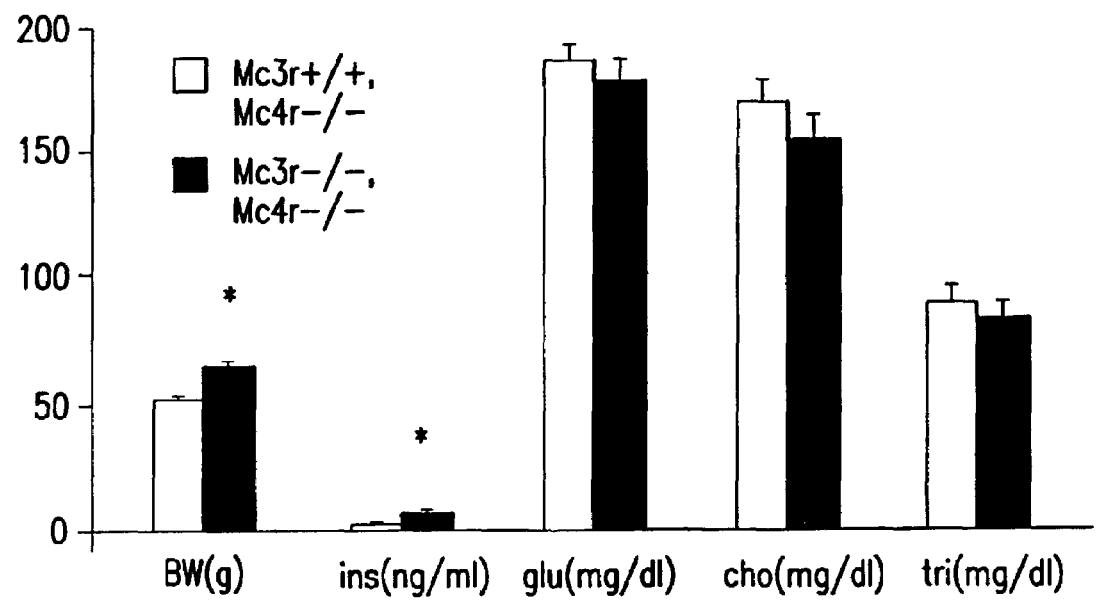
Figure 20A:
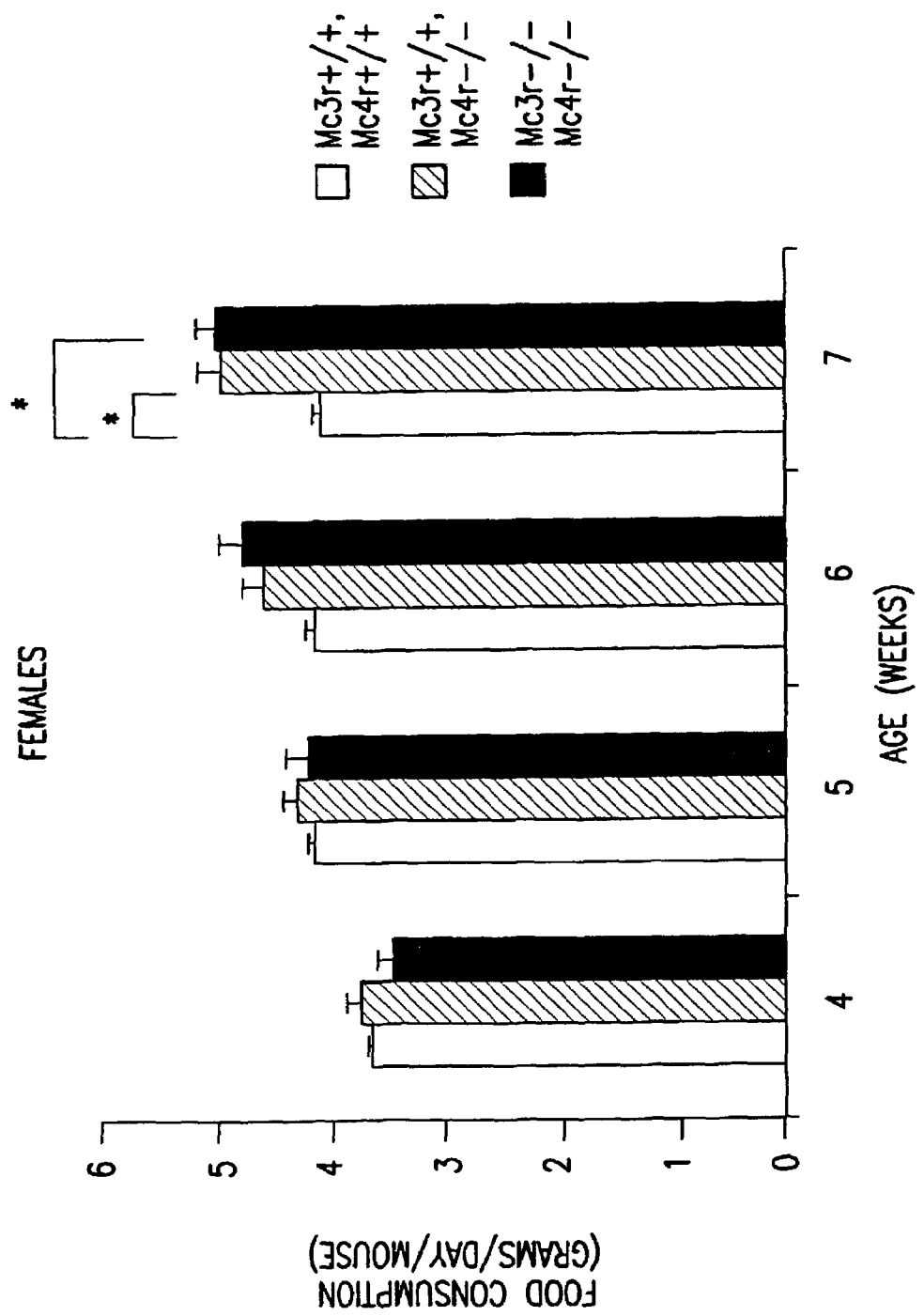
FIG. 20 A-B show that the MC-3R$^{-/-}$×MC-4R$^{-/-}$ mice consume similar amounts of food as MC-4R$^{-/-}$ mice and both were significantly hyperphagic in comparison to wild type (WT) mice by 7-weeks old (FIG. 20A). However, the female MC-3R$^{-/-}$×MC-4R$^{-/-}$ mice displayed significantly greater feed efficiency than female MC-4R$^{-/-}$ and wild type (WT) mice at 5-6 weeks of age (FIG. 20B). Male MC-3R$^{-/-}$×MC-4R$^{-/-}$ mice showed similar trend but did not reach statistical significance in feed efficiency.
Figure 20B:
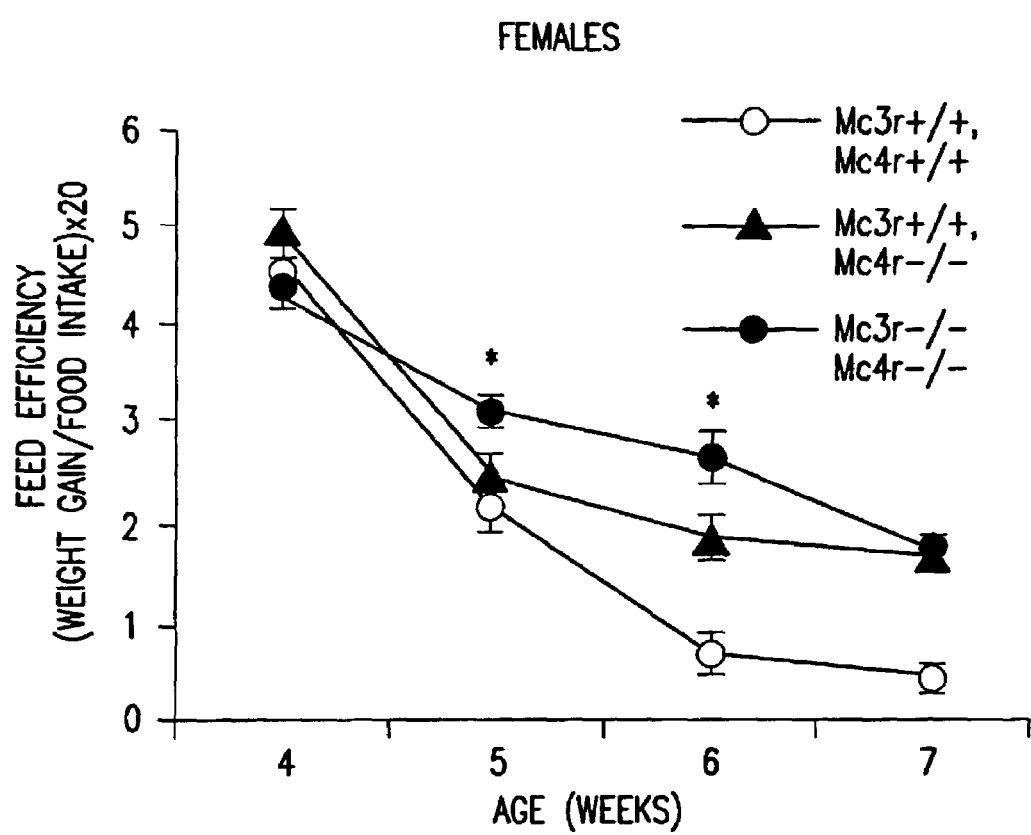

Significant differences are noteworthy when comparing the MC-3R$^{-/-}$ and MC-4R$^{-/-}$ mice. In contrast to MC-3R$^{-/-}$ mice, MC-4R$^{-/-}$ mice are hyperphagic, exhibit significant hyperinsulinemia and alterations in metabolic rate, and maintain normal levels of lean body mass. Further support for the notion that the phenotypes of the MC-3R$^{-/-}$ and MC-4R$^{-/-}$ mice are not redundant comes from body weight analysis of mice lacking both MC-3R$^{-/-}$ and MC-4R (MC-3R$^{-/-}$×MC-4R$^{-/-}$ mice, as described in this Example and shown in FIGS. 17 (at 26 weeks) and 18A-B(up to 26 weeks). At 26 weeks of age, female MC-3R$^{-/-}$×MC-4R— mice are significantly heavier ($\int$27%; P<0.0001) than littermate mice lacking only MC-4R (MC-3R$^{-/-}$×MC-4R4$^{-/-}$, 64.58±1.92 g vs. MC-4R4$^{-/-}$, 50.77±1.48 g; n=10-18) and male MC-3R$^{-/-}$×MC4R$^{-/-}$ mice are also significantly heavier (~13%; P<0.05) than littermate MC-4R$^{-/-}$ mice (MC-3R$^{-/-}$×MC4R$^{-/-}$, 62.57±1.86 g vs. MC-4R-1-, 55.60±1.70 g; n=9-13). To this end, FIGS. 18A-B shows that the female (FIG. 18A) double knockout mice are significantly heavier (p<0.01) than MC-4R$^{-/-}$ mice at six-week-olds. As noted above, by twenty-six-weeks female MC-3R$^{-/-}$×MC-4R$^{-/-}$ mice are significantly heavier (~27%) than littermates lacking only MC-4R (MC-3R$^{-/-}$×MC-4R$^{-/-}$, 64.58±1.92 g vs. MC-4R$^{-/-}$, 50.77±1.48 g; n=10-18; P<0.0001) and male MC-3R$^{-/-}$×MC4$^{-/-}$ mice (FIG. 18B) of comparable age are also significantly heavier (~13%) than MC-4R$^{-/-}$ littermates (MC-3R$^{-/-}$×MC-4R$^{-/-}$, 62.57±1.86 g vs. MC-4R$^{-/-}$, 55.60±1.70 g; n=9-13; P<0.05). FIGS. 19A-B show that the plasma insulin level of 9-month-old female (FIG. 19A) and male (FIG. 19B) MC-3R$^{-/-}$×MC-4R$^{-/-}$ mice is statistically higher than littermates lacking only MC-4R (male: MC-3R$^{-/-}$×MC-4R$^{-/-}$, 50.72: 17.92 ng/ml vs. 8.88±1.93 ng/ml; n=11-13; P<0.05 and female: MC-3R$^{-/-}$×MC-4R$^{-/-}$, 8.59±1.63 ng/ml vs. 1.65±0.53 ng/ml; n=10-14; P<0.01). The glucose level are similar between MC-3R$^{-/-}$×MC4R$^{-/-}$ and MC4R$^{-/-}$ mice, as shown in FIGS. 19A and 19B. In addition, FIG. 20 A-B show that the MC-3R$^{-/-}$×MC4R$^{-/-}$ mice consume similar amounts of food as MC-4R-/- mice and both showed significantly hyperphagic than WT mice by 7-week old (FIGS. 20A-B). However, the female MC-3R$^{-/-}$×MC-4R$^{-/-}$ mice displayed significantly greater feed efficiency than female MC-4R$^{-/-}$ and WT mice at 5-6 weeks of age (FIG. 20B). Male MC-3$^{-/-}$×MC-4R$^{-/-}$ mice showed similar trend but did not reach statistical significance in feed efficiency. These data show that MC-3R serves a non-redundant role, when compared to MC-4R$^{-/-}$ in the regulation of energy homeostasis. In addition, the data also shows that MC-3R and MC-4R may work synergistically, suggesting that MC-3R$^{-/-}$×MC-4R$^{-/-}$ mice may serve as a better model than MC4R$^{-/-}$ mice for the treatment of obesity and the other related disease.

What is claimed is:

1. A transgenic mouse whose somatic cells and germ cells are homozygous for an altered melanocortin-3 receptor (MC-3R) gene and homozygous for an altered melanocortin-4 receptor (MC-4R) gene, wherein the mouse lacks functional MC-3R and MC-4R proteins, and further wherein the mouse exhibits an increased body weight compared to a non-transgenic mouse.

2. A cell line derived from a transgenic mouse of claim 1, wherein the cell lacks functional MC-3R protein and functional MC4R protein.

3. The mouse of claim 1, wherein the mouse is fertile and transmits the altered MC-3R gene and MC-4R gene to its offspring.

* * * * *

SEQUENCE LISTING

<160> NUMBER OF SEQ ID NOS: 15

<210> SEQ ID NO 1
<211> LENGTH: 1675
<212> TYPE: DNA
<213> ORGANISM: Mus musculus (house mouse)

<400> SEQUENCE: 1

```
tctagactgg acagcatcca caagagaagc acctagaagg agaattttcc ccagcagctt      60
gctcaggacc ctgcaggagc cgcagctggg actggacctg ctgttaacca tgaactcttc     120
ctgctgcctg tcttctgttt ctccgatgct gcctaacctc tctgagcacc ctgcagcccc     180
```

-continued

```
tcctgccagc aaccggagcg gcagtgggtt ctgtgagcag gtcttcatca agccggaggt      240
cttcctggct ctgggcatcg tcagtctgat ggaaaacatc ctggtgatcc tggctgtggt      300
caggaatggc aacctgcact ctcccatgta cttcttcctg tgcagcctgg ctgcagccga      360
catgctggtg agcctgtcca actccctgga gaccatcatg atcgccgtga tcaacagcga      420
ctccctgacc ttggaggacc agtttatcca gcacatggat aatatcttcg actctatgat      480
ttgcatctcc ctggtggcct ccatctgcaa cctcctggcc attgccatcg acaggtacgt      540
caccatcttc tatgcccttc ggtaccacag catcatgaca gttaggaaag ccctcacctt      600
gatcggggtc atctgggtct gctgcggcat ctgcggcgtg atgttcatca tctactccga      660
gagcaagatg gtcatcgtgt gtctcatcac catgttcttc gccatggtgc tcctcatggg      720
caccctatat atccacatgt tcctcttcgc caggctccac gtccagcgca tcgcagtgct      780
gccccctgct ggcgtggtgg ccccacagca gcactcctgc atgaaggggg ctgtcaccat      840
cactatcctg ctgggtgttt tcatcttctg ctgggcgcct ttcttcctcc acctggtcct      900
catcatcacc tgccccacca atccctactg catctgctac acggcccatt caacaccta       960 cctggttctc atcatgtgca actccgtcat cgaccccctc atctacgcct ccgcagcct      1020 ggagctgcgc aacacgttca aggagattct ctgcggctgc aacagcatga acttgggcta     1080
ggatgcccgt ggaggtgttc cacatccagc aagagacaa aaacaacgct cagacgggac     1140
gtaaaagggt gttaggagct ggaactgtgc ttggcttcgt ctgtaagctc gtggcccttt     1200
gcagacggga cacggcgtag gatgggctgt ctgtgaggat ctgtgtgtgg gtaagtcagt     1260
ttgatctagc acatagcctg gaagaatcag gcaaagcagc cctgagtgtc atctgtgttc     1320
attgctaggc acccagggtt tgtggcccct gcctgcttat tggctttgta ccagtaactg     1380
tgcttcaagc caaccagacc ggagggctct cgtgagcaga aagagtgctt agacttccgg     1440
caagcatcct ggctcacagc ggccactcc tgaccactac cgggagagct ttgcacatat     1500
tctgtgggag attgagtgaa gccctgaaaa caatgtgata tttgctgctc ccttccagaa     1560
cttacatctg tgccagcctc cccgaacccc tgcacagaga catgacccccc ttctccctgt    1620 gccgttgtca tggttgttat tattgttgga gttttgttcg ttaaaatcta agctt           1675
```

<210> SEQ ID NO 2
<211> LENGTH: 323
<212> TYPE: PRT
<213> ORGANISM: Mus musculus (house mouse)

<400> SEQUENCE: 2

```
Met Asn Ser Ser Cys Cys Leu Ser Ser Val Ser Pro Met Leu Pro Asn
 1               5                  10                  15

Leu Ser Glu His Pro Ala Ala Pro Ala Ser Asn Arg Ser Gly Ser
            20                  25                  30

Gly Phe Cys Glu Gln Val Phe Ile Lys Pro Glu Val Phe Leu Ala Leu
        35                  40                  45

Gly Ile Val Ser Leu Met Glu Asn Ile Leu Val Ile Leu Ala Val Val
    50                  55                  60

Arg Asn Gly Asn Leu His Ser Pro Met Tyr Phe Phe Leu Cys Ser Leu
65                  70                  75                  80

Ala Ala Ala Asp Met Leu Val Ser Leu Ser Asn Ser Leu Glu Thr Ile
                85                  90                  95

Met Ile Ala Val Ile Asn Ser Asp Ser Leu Thr Leu Glu Asp Gln Phe
            100                 105                 110
```

-continued

```
Ile Gln His Met Asp Asn Ile Phe Asp Ser Met Ile Cys Ile Ser Leu
        115                 120                 125

Val Ala Ser Ile Cys Asn Leu Leu Ala Ile Ala Ile Asp Arg Tyr Val
130                 135                 140

Thr Ile Phe Tyr Ala Leu Arg Tyr His Ser Ile Met Thr Val Arg Lys
145                 150                 155                 160

Ala Leu Thr Leu Ile Gly Val Ile Trp Val Cys Cys Gly Ile Cys Gly
                165                 170                 175

Val Met Phe Ile Ile Tyr Ser Glu Ser Lys Met Val Ile Val Cys Leu
            180                 185                 190

Ile Thr Met Phe Phe Ala Met Val Leu Leu Met Gly Thr Leu Tyr Ile
        195                 200                 205

His Met Phe Leu Phe Ala Arg Leu His Val Gln Arg Ile Ala Val Leu
210                 215                 220

Pro Pro Ala Gly Val Val Ala Pro Gln Gln His Ser Cys Met Lys Gly
225                 230                 235                 240

Ala Val Thr Ile Thr Ile Leu Leu Gly Val Phe Ile Phe Cys Trp Ala
                245                 250                 255

Pro Phe Phe Leu His Leu Val Leu Ile Ile Thr Cys Pro Thr Asn Pro
            260                 265                 270

Tyr Cys Ile Cys Tyr Thr Ala His Phe Asn Thr Tyr Leu Val Leu Ile
        275                 280                 285

Met Cys Asn Ser Val Ile Asp Pro Leu Ile Tyr Ala Phe Arg Ser Leu
290                 295                 300

Glu Leu Arg Asn Thr Phe Lys Glu Ile Leu Cys Gly Cys Asn Ser Met
305                 310                 315                 320

Asn Leu Gly

<210> SEQ ID NO 3
<211> LENGTH: 1080
<212> TYPE: DNA
<213> ORGANISM: Homo sapien

<400> SEQUENCE: 3
atgagcatcc aaaagaagta tctggaggga gattttgtct ttcctgtgag cagcagcagc      60
ttcctacgga ccctgctgga gccccagctc ggatcagccc ttctgacagc aatgaatgct     120
tcgtgctgcc tgccctctgt tcagccaaca ctgcctaatg gctcggagca cctccaagcc     180
cctttcttca gcaaccagag cagcagcgcc ttctgtgagc aggtcttcat caagcccgag     240
attttcctgt ctctgggcat cgtcagtctg ctggaaaaca tcctggttat cctggccgtg     300
gtcaggaacg gcaacctgca ctccccgatg tacttctttc tctgcagcct ggcggtggcc     360
gacatgctgg taagtgtgtc caatgccctg agaccatca tgatcgccat cgtccacagc      420
gactacctga ccttcgagga ccagtttatc agcacatgg acaacatctt cgactccatg      480
atctgcatct ccctggtggc ctccatctgc aacctcctgg ccatcgccgt cgacaggtac     540
gtcaccatct tttacgcgct ccgctaccac agcatcatga ccgtgaggaa ggccctcacc     600
ttgatcgtgg ccatctgggt ctgctgcggc gtctgtggcg tggtgttcat cgtctactcg     660
gagagcaaaa tggtcattgt gtgcctcatc accatgttct tcgccatgat gctcctcatg     720
ggcaccctct acgtgcacat gttcctcttt gcgcggctgc acgtcaagcg catagcagca     780
ctgccacctg ccgacggggt ggccccacag caacactcat gcatgaaggg ggcagtcacc     840
atcaccattc tcctgggcgt gttcatcttc tgctgggccc ccttcttcct ccacctggtc     900
```

```
ctcatcatca cctgccccac caacccctac tgcatctgct acactgccca cttcaacacc    960
tacctggtcc tcatcatgtg caactccgtc atcgacccac tcatctacgc tttccggagc   1020
ctggaattgc gcaacacctt tagggagatt ctctgtggct gcaacggcat gaacttggga   1080
```

<210> SEQ ID NO 4
<211> LENGTH: 360
<212> TYPE: PRT
<213> ORGANISM: Homo sapien
<400> SEQUENCE: 4

```
Met Ser Ile Gln Lys Lys Tyr Leu Glu Gly Asp Phe Val Phe Pro Val
 1               5                  10                  15

Ser Ser Ser Ser Phe Leu Arg Thr Leu Leu Glu Pro Gln Leu Gly Ser
                20                  25                  30

Ala Leu Leu Thr Ala Met Asn Ala Ser Cys Cys Leu Pro Ser Val Gln
            35                  40                  45

Pro Thr Leu Pro Asn Gly Ser Glu His Leu Gln Ala Pro Phe Phe Ser
        50                  55                  60

Asn Gln Ser Ser Ser Ala Phe Cys Glu Gln Val Phe Ile Lys Pro Glu
65                  70                  75                  80

Ile Phe Leu Ser Leu Gly Ile Val Ser Leu Leu Glu Asn Ile Leu Val
                85                  90                  95

Ile Leu Ala Val Val Arg Asn Gly Asn Leu His Ser Pro Met Tyr Phe
            100                 105                 110

Phe Leu Cys Ser Leu Ala Val Ala Asp Met Leu Val Ser Val Ser Asn
        115                 120                 125

Ala Leu Glu Thr Ile Met Ile Ala Ile Val His Ser Asp Tyr Leu Thr
    130                 135                 140

Phe Glu Asp Gln Phe Ile Gln His Met Asp Asn Ile Phe Asp Ser Met
145                 150                 155                 160

Ile Cys Ile Ser Leu Val Ala Ser Ile Cys Asn Leu Leu Ala Ile Ala
                165                 170                 175

Val Asp Arg Tyr Val Thr Ile Phe Tyr Ala Leu Arg Tyr His Ser Ile
            180                 185                 190

Met Thr Val Arg Lys Ala Leu Thr Leu Ile Val Ala Ile Trp Val Cys
        195                 200                 205

Cys Gly Val Cys Gly Val Val Phe Ile Val Tyr Ser Glu Ser Lys Met
    210                 215                 220

Val Ile Val Cys Leu Ile Thr Met Phe Phe Ala Met Met Leu Leu Met
225                 230                 235                 240

Gly Thr Leu Tyr Val His Met Phe Leu Phe Ala Arg Leu His Val Lys
                245                 250                 255

Arg Ile Ala Ala Leu Pro Pro Ala Asp Gly Val Ala Pro Gln Gln His
            260                 265                 270

Ser Cys Met Lys Gly Ala Val Thr Ile Thr Ile Leu Leu Gly Val Phe
        275                 280                 285

Ile Phe Cys Trp Ala Pro Phe Phe Leu His Leu Val Leu Ile Ile Thr
    290                 295                 300

Cys Pro Thr Asn Pro Tyr Cys Ile Cys Tyr Thr Ala His Phe Asn Thr
305                 310                 315                 320

Tyr Leu Val Leu Ile Met Cys Asn Ser Val Ile Asp Pro Leu Ile Tyr
                325                 330                 335
```

```
Ala Phe Arg Ser Leu Glu Leu Arg Asn Thr Phe Arg Glu Ile Leu Cys
             340                 345                 350
Gly Cys Asn Gly Met Asn Leu Gly
    355                 360
```

<210> SEQ ID NO 5
<211> LENGTH: 28
<212> TYPE: DNA
<213> ORGANISM: Artificial Sequence
<220> FEATURE:
<223> OTHER INFORMATION: oligonucleotide

<400> SEQUENCE: 5
gatgagagaa gactggagag agagggtc                                        28

<210> SEQ ID NO 6
<211> LENGTH: 27
<212> TYPE: DNA
<213> ORGANISM: Artificial Sequence
<220> FEATURE:
<223> OTHER INFORMATION: oligonucleotide

<400> SEQUENCE: 6
gaagaagtac atgggagagt gcaggtt                                         27

<210> SEQ ID NO 7
<211> LENGTH: 27
<212> TYPE: DNA
<213> ORGANISM: Artificial Sequence
<220> FEATURE:
<223> OTHER INFORMATION: oligonucleotide

<400> SEQUENCE: 7
gatgagagaa gactggagga gagggtc                                         27

<210> SEQ ID NO 8
<211> LENGTH: 24
<212> TYPE: DNA
<213> ORGANISM: Artificial Sequence
<220> FEATURE:
<223> OTHER INFORMATION: oligonucleotide

<400> SEQUENCE: 8
taccggtgga tgtggaatgt gtgc                                            24

<210> SEQ ID NO 9
<211> LENGTH: 45
<212> TYPE: DNA
<213> ORGANISM: Artificial Sequence
<220> FEATURE:
<223> OTHER INFORMATION: oligonucleotide

<400> SEQUENCE: 9
agccaggatc accaggatgt tttccatcag actgacgatg cccag                     45

<210> SEQ ID NO 10
<211> LENGTH: 45
<212> TYPE: DNA
<213> ORGANISM: Artificial Sequence
<220> FEATURE:
<223> OTHER INFORMATION: oligonucleotide

<400> SEQUENCE: 10
tgcccatgag gagcaccatg gcgaagaaca tggtgatgag gcaca                     45

-continued

```
<210> SEQ ID NO 11
<211> LENGTH: 45
<212> TYPE: DNA
<213> ORGANISM: Artificial Sequence
<220> FEATURE:
<223> OTHER INFORMATION: oligonucleotide

<400> SEQUENCE: 11
atgatgagga ccaggtggag gaagaaaggc gcccagcaga agatg            45

<210> SEQ ID NO 12
<211> LENGTH: 25
<212> TYPE: DNA
<213> ORGANISM: Artificial Sequence
<220> FEATURE:
<223> OTHER INFORMATION: oligonucleotide

<400> SEQUENCE: 12
ctaaccataa gaaatcagca gcccg                                  25

<210> SEQ ID NO 13
<211> LENGTH: 25
<212> TYPE: DNA
<213> ORGANISM: Artificial Sequence
<220> FEATURE:
<223> OTHER INFORMATION: oligonucleotide

<400> SEQUENCE: 13
agggaagtat acatgccatg gtggt                                  25

<210> SEQ ID NO 14
<211> LENGTH: 25
<212> TYPE: DNA
<213> ORGANISM: Artificial Sequence
<220> FEATURE:
<223> OTHER INFORMATION: oligonucleotide

<400> SEQUENCE: 14
ctaaccataa gaaatcagca gcccg                                  25

<210> SEQ ID NO 15
<211> LENGTH: 24
<212> TYPE: DNA
<213> ORGANISM: Artificial Sequence
<220> FEATURE:
<223> OTHER INFORMATION: oligonucleotide

<400> SEQUENCE: 15
taccggtgga tgtggaatgt gtgc                                   24
```